(12) United States Patent
Horikiri et al.

(10) Patent No.: US 9,005,778 B2
(45) Date of Patent: Apr. 14, 2015

(54) ORGANIC COMPOUND AND ORGANIC LIGHT-EMITTING DEVICE INCLUDING THE SAME

(75) Inventors: Tomonari Horikiri, Chiba (JP); Hiroyuki Tomono, Numazu (JP); Jun Kamatani, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 303 days.

(21) Appl. No.: 13/643,972

(22) PCT Filed: Apr. 19, 2011

(86) PCT No.: PCT/JP2011/060007
§ 371 (c)(1),
(2), (4) Date: Oct. 26, 2012

(87) PCT Pub. No.: WO2011/136155
PCT Pub. Date: Nov. 3, 2011

(65) Prior Publication Data
US 2013/0038515 A1    Feb. 14, 2013

(30) Foreign Application Priority Data

Apr. 30, 2010    (JP) .................................. 2010-105625

(51) Int. Cl.
*H01L 51/54* (2006.01)
*C07C 13/62* (2006.01)
(Continued)

(52) U.S. Cl.
CPC ............ *C07D 213/127* (2013.01); *C07C 13/62* (2013.01); *C07C 25/22* (2013.01); *C07C 49/792* (2013.01); *C07C 211/61* (2013.01); *C07F 7/0809* (2013.01); *C07F 9/5022* (2013.01); *H01L 51/0057* (2013.01); *H01L 51/006* (2013.01); *H01L 51/0067* (2013.01); *C09K 11/06* (2013.01); *H05B 33/10* (2013.01); *C07C 2101/14* (2013.01); *C07C 2102/42* (2013.01); *C07C 2103/18* (2013.01); *C07C 2103/24* (2013.01); *C07C 2103/40* (2013.01); *C07C 2103/52* (2013.01); *C07C 2103/54* (2013.01);
(Continued)

(58) Field of Classification Search
CPC   C07C 13/62; C07C 2101/14; C07C 2102/42; C07C 2103/18; C07C 2103/24; C07C 2103/40; C07C 2103/52; C07C 2103/54; C07C 211/61; C07C 25/22; C07C 49/792; C07D 213/127; C07F 7/0809; C07F 9/5022; C09K 2211/1007; C09K 2211/1011; C09K 2211/1029; C09K 2211/1059; C09K 2211/1092; H01L 51/0057; H01L 51/0058; H01L 51/0059; H01L 51/006; H01L 51/0067; H01L 51/5012; H05B 33/10
See application file for complete search history.

(56) References Cited

U.S. PATENT DOCUMENTS

| 2002/0168544 | A1* | 11/2002 | Fukuoka et al. | ............... 428/690 |
| 2003/0027016 | A1 | 2/2003 | Ara | |
| 2004/0076853 | A1* | 4/2004 | Jarikov | ........................ 428/690 |

FOREIGN PATENT DOCUMENTS

| CN | 101541713 A | 9/2009 |
| JP | 9-241629 A | 9/1997 |

(Continued)

*Primary Examiner* — Dawn L. Garrett
(74) *Attorney, Agent, or Firm* — Canon U.S.A. Inc., IP Division

(57) ABSTRACT

There is provided a novel organic compound suitably used for a blue light-emitting device and an organic light-emitting device including the novel organic compound. The organic compound is an acephenanthryleno[4,5-k]benzo[e]acephenanthrylene derivative.

12 Claims, 1 Drawing Sheet

(51) Int. Cl.

| | |
|---|---|
| *G09G 3/32* | (2006.01) |
| *C07D 213/16* | (2006.01) |
| *C07D 251/24* | (2006.01) |
| *C07C 211/61* | (2006.01) |
| *C07D 215/06* | (2006.01) |
| *C07D 221/06* | (2006.01) |
| *C07D 401/10* | (2006.01) |
| *C07D 213/127* | (2006.01) |
| *C07C 25/22* | (2006.01) |
| *C07C 49/792* | (2006.01) |
| *C07F 7/08* | (2006.01) |
| *C07F 9/50* | (2006.01) |
| *H01L 51/00* | (2006.01) |
| *C09K 11/06* | (2006.01) |
| *H05B 33/10* | (2006.01) |
| *H01L 51/50* | (2006.01) |

(52) U.S. Cl.
CPC ......... *H01L 51/0058* (2013.01); *H01L 51/0059* (2013.01); *H01L 51/5012* (2013.01); *C09K 2211/1007* (2013.01); *C09K 2211/1011* (2013.01); *C09K 2211/1029* (2013.01); *C09K 2211/1059* (2013.01); *C09K 2211/1092* (2013.01); *Y10S 428/917* (2013.01)

(56) References Cited

FOREIGN PATENT DOCUMENTS

| | | |
|---|---|---|
| JP | 2003238516 A | 8/2003 |
| WO | 2008/120806 A1 | 10/2008 |
| WO | 2010/071223 A1 | 6/2010 |
| WO | 2010/123153 A1 | 10/2010 |

* cited by examiner

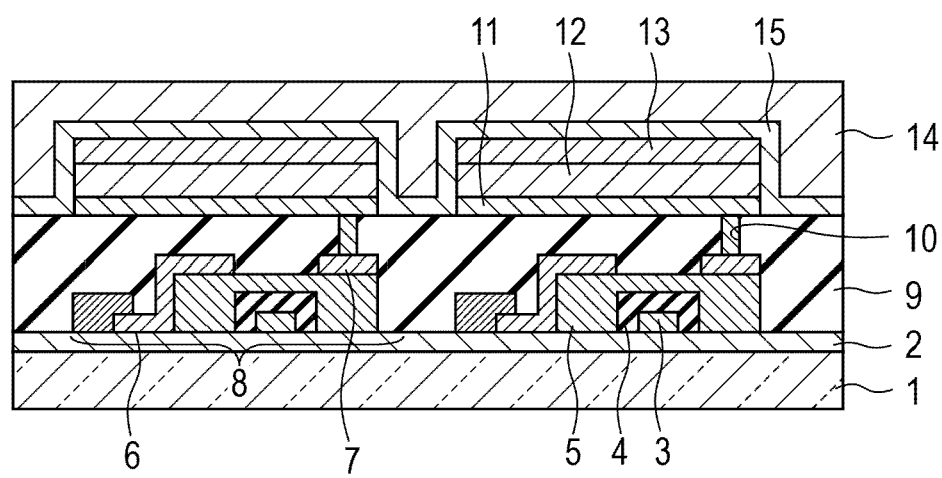

ORGANIC COMPOUND AND ORGANIC LIGHT-EMITTING DEVICE INCLUDING THE SAME

TECHNICAL FIELD

The present invention relates to a novel organic compound and an organic light-emitting device including the novel organic compound.

BACKGROUND ART

Organic light-emitting devices include a pair of electrodes and an organic compound layer disposed between the pair of electrodes. By injecting electrons and holes from the pair of electrodes, excitons of an organic compound contained in the organic compound layer are generated and light is emitted when the excitons return to the ground state.

Organic light-emitting devices are also referred to as organic electroluminescent (EL) devices.

In recent years, organic light-emitting devices have been remarkably advancing, and there can be provided a light-emitting device that can achieve high luminance at low voltage, a wider range of emission wavelengths, rapid response, and reduction in thickness and weight. Novel luminescent organic compounds have been created so far.

PTL 1 discloses IK-12 shown below as an example of an organic compound that constitutes a light-emitting layer, which is the organic compound layer. This compound has benzo[k]fluoranthene.

[Chem. 1]

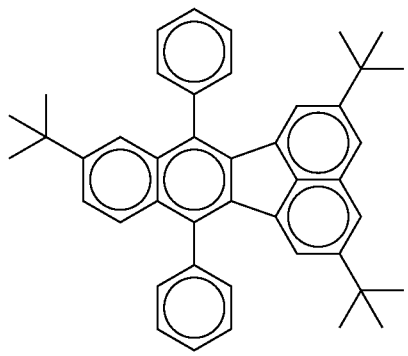

(IK-12)

Benzo[k]fluoranthene is shown below as a basic skeleton. This is a fused ring compound whose ring has a conjugated structure.

[Chem. 2]

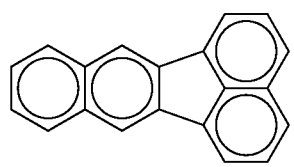

CITATION LIST

Patent Literature

PTL 1 Japanese Patent Laid-Open No. 9-241629 (no corresponding foreign publication)

SUMMARY OF INVENTION

The IK-12 disclosed in PTL 1 has benzo[k]fluoranthene and also has substituents. As a result, blue light emission can be achieved. However, if a substituent such as a tert-butyl group is introduced, the stability of the compound may be impaired. Accordingly, the present invention provides a novel organic compound that achieves blue light emission by itself and has high stability by newly creating a basic skeleton itself.

The present invention provides an organic compound represented by general formula (1) or (3) below.

[Chem. 3]

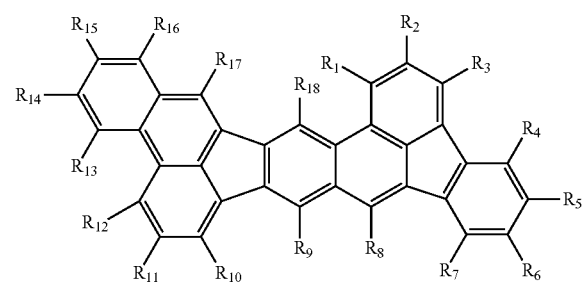

(1)

In the general formula (1), $R_1$ to $R_{18}$ are each independently selected from a hydrogen atom, a halogen atom, an alkyl group, an alkoxy group, an amino group, an aryl group, and a heterocyclic group.

[Chem. 4]

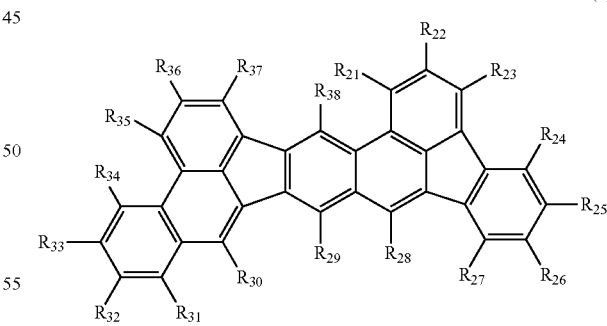

(3)

In the general formula (3), $R_{21}$ to $R_{38}$ are each independently selected from a hydrogen atom, a halogen atom, an alkyl group, an alkoxy group, an amino group, an aryl group, and a heterocyclic group.

According to the present invention, there can be provided an organic compound that achieves blue light emission with a basic skeleton alone and has high stability. There can also be provided an organic light-emitting device including the organic compound.

BRIEF DESCRIPTION OF DRAWINGS

FIG. 1 is a schematic sectional view showing an organic light-emitting device and a switching device connected to the organic light-emitting device.

DESCRIPTION OF EMBODIMENT

The present invention provides an organic compound represented by general formula (1) below.

[Chem. 5]

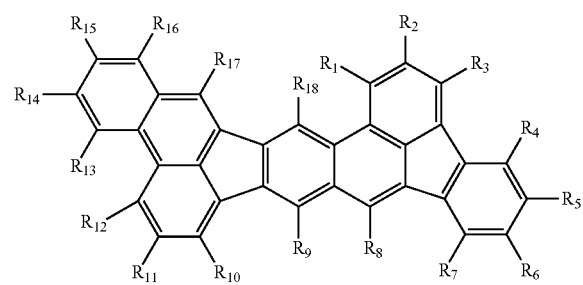

In the general formula (1), $R_1$ to $R_{18}$ are each independently selected from a hydrogen atom, a halogen atom, an alkyl group, an alkoxy group, an amino group, an aryl group, and a heterocyclic group.

Examples of the alkyl group in the general formula (1) include a methyl group, an ethyl group, an n-propyl group, an isopropyl group, an n-butyl group, an isobutyl group, a sec-butyl group, a tert-butyl group, an octyl group, a 1-adamantyl group, and a 2-adamantyl group.

Examples of the alkoxy group in the general formula (1) include a methoxy group, an ethoxy group, a propoxy group, a 2-ethyl-octyloxy group, a phenoxy group, a 4-tert-butylphenoxy group, a benzyloxy group, and a thienyloxy group.

Examples of the amino group in the general formula (1) include an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphthylamino group, an N,N-difluorenylamino group, an N-phenyl-N-tolylamino group, an N,N-ditolylamino group, an N-methyl-N-phenylamino group, an N,N-dianisolylamino group, an N-mesityl-N-phenylamino group, an N,N-dimesitylamino group, an N-phenyl-N-(4-tert-butylphenyl)amino group, and an N-phenyl-N-(4-trifluoromethylphenyl)amino group.

Examples of the aryl group in the general formula (1) include a phenyl group, a naphthyl group, an indenyl group, a biphenyl group, a terphenyl group, and a fluorenyl group.

Examples of the heterocyclic group in the general formula (1) include a pyridyl group, an oxazolyl group, an oxadiazolyl group, a thiazolyl group, a thiadiazolyl group, a carbazolyl group, an acridinyl group, and a phenanthrolyl group.

The above-mentioned substituents, that is, the alkyl group, the alkoxy group, the amino group, the aryl group, and the heterocyclic group, which are $R_1$ to $R_{18}$ in the general formula (1), may have a substituent. Examples of the substituent include alkyl groups such as a methyl group, an ethyl group, and a propyl group; aralkyl groups such as a benzyl group; aryl groups such as a phenyl group and a biphenyl group; heterocyclic groups such as a pyridyl group and a pyrrolyl group; amino groups such as a dimethylamino group, a diethylamino group, a dibenzylamino group, a diphenylamino group, and a ditolylamino group; alkoxyl groups such as a methoxyl group, an ethoxyl group, a propoxyl group, and a phenoxyl group; cyano groups; and halogen atoms such as fluorine, chlorine, bromine, and iodine.

The inventors of the present invention have paid attention to the basic skeleton itself. Specifically, the inventors have attempted to provide a compound in which a molecule having only a basic skeleton has a peak emission wavelength within a desired emission wavelength region.

It is known that a substituent is introduced onto a basic skeleton in order to achieve a desired peak emission wavelength. In that case, however, the stability of the compound may be impaired.

When an organic light-emitting device is used for a display apparatus, the peak emission wavelength needs to be within 430 to 480 nm to achieve blue light emission.

The organic compound according to the present invention is a compound having a peak emission wavelength of 430 to 480 nm. That is, such a compound can be a luminescent material of a blue organic light-emitting device.

To increase the emission efficiency of the organic light-emitting device, the quantum yield of the luminescent material itself needs to be high.

To achieve this, the following conditions are required.
1. The oscillator strength is high.
2. The skeleton that contributes to light emission has a small oscillatory region.

Regarding the condition 1, it is important to improve the symmetry of a skeleton of a luminescent material that contributes to light emission. This is because the transition dipole moment of each atom in a molecule having high symmetry is easily oriented in the same direction and thus the transition dipole moment is increased. High transition dipole moment leads to high oscillator strength, which results in high quantum yield.

Furthermore, since the transition dipole moment of a molecule is increased by extending conjugation in a certain direction, the oscillator strength is increased.

The organic compound according to the present invention has a fused ring structure formed by extending the conjugation from the 8-position to 11-position of benzo[k]fluoranthene. Such a structure has a transition dipole moment higher than that of the benzo[k]fluoranthene.

That is, the organic compound according to the present invention has a structure with high oscillator strength.

Regarding the condition 2, when the basic skeleton has no rotational structure, the conversion of energy the organic compound has obtained into kinetic energy such as rotational or vibrational energy is suppressed and thus the ratio of energy emitted as photons can be increased. In other words, the decrease in quantum yield can be suppressed.

The basic skeleton of the organic compound according to the present invention, i.e., the acephenanthryl[4,5-k]benzo[e]acephenanthrene skeleton, itself has a peak emission wavelength in the blue region. Moreover, this basic skeleton has no rotational structure and therefore can suppress the decrease in quantum yield caused by rotational vibration.

A comparative example of the basic skeleton is benzo[b]fluoranthene. When the benzo[b]fluoranthene is compared with acephenanthryl[4,5-k]benzo[e]-7,10-diphenylacephenanthrene (example compound A110), which is an example of the present invention, the peak emission wavelength of the former is 395 nm whereas the peak emission wavelength of the latter is 439 nm.

The organic compound according to the present invention has a peak emission wavelength in the blue region whereas the comparative compound does not have a peak emission wavelength in the blue region. The quantum yield of the comparative compound is 0.49 whereas the quantum yield of the organic compound according to the present invention is 0.80. The compound according to the present invention emits light at an efficiency higher than that of the comparative compound.

A comparison has been performed using the example compound A110, which is an example of the organic compound according to the present invention. The basic skeleton itself of the organic compound according to the present invention has a peak emission wavelength in the blue region and high quantum yield. This is because the phenyl groups provided at the 7- and 10-positions of the example compound A110 have little effect on the peak emission wavelength and also on the quantum yield.

[Chem. 6]

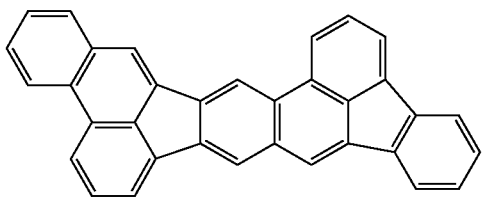 [SMILES: c1ccc2c(c1)cc1c3cc4c(cc3c3cccc2c31)cc1c2ccccc2c2cccc4c21]

Basic skeleton of the present invention

[Chem. 7]

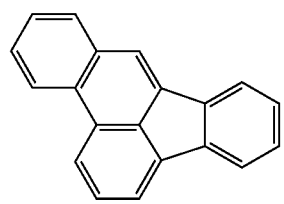

benzo[b]fluoranthene

[Chem. 8]

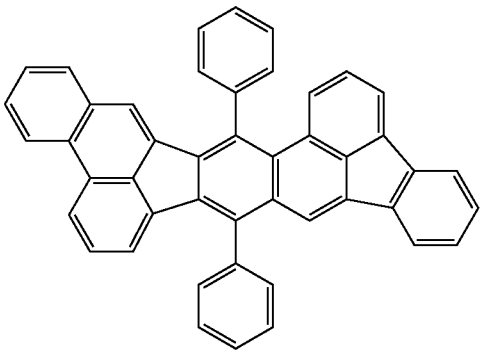

acephenanthryl[4,5-k]benzo[e]-7,10-diphenylacephenanthrene
(Compound A110)

Accordingly, in the organic compound according to the present invention, the basic skeleton itself achieves blue light emission and high quantum yield.

Since the organic compound according to the present invention has two five-membered-ring structures in the basic skeleton thereof, the HOMO/LUMO energy levels are low. Thus, the organic compound according to the present invention has a high oxidation potential.

This means that a larger amount of energy is required to oxidize the organic compound according to the present invention. That is, the organic compound according to the present invention is stable against oxidation.

The basic skeleton of the organic compound according to the present invention is highly planar and easily generates excimers by intermolecular stacking. Therefore, a steric hindrance group, i.e., a bulky substituent may be introduced to prevent the intermolecular stacking.

The position of a substituent that produces a high effect of steric hindrance was calculated. Specifically, calculation was done by quantum chemical calculation at the B3LYP/6-31G* level using a density functional theory.

Herein, a dihedral angle of a bond between the basic skeleton and the substituent (phenyl group in this calculation) is obtained to determine the effect of steric hindrance. The effect of steric hindrance is increased as the dihedral angle approaches 90°, which increases the effect of suppressing intermolecular stacking.

Table 1 shows the calculation results. Table 1 also shows the absorption value (S1) obtained from the quantum chemical calculation.

TABLE 1

| | Structural formula | Dihedral angle (°) | Absorption value (S1) (nm) |
|---|---|---|---|
| Non-substituted compound | | — | 406 |

TABLE 1-continued

| Structural formula | Dihedral angle (°) | Absorption value (S1) (nm) |
|---|---|---|
| Phenyl-substituted compound at 3-position | 54.2 | 412 |
| Phenyl-substituted compound at 5-position | 38.1 | 416 |
| Phenyl-substituted compound at 9-position | 89.6 | 409 |
| Phenyl-substituted compound at 10-position | 56.5 | 413 |
| Phenyl-substituted compound at 14-position | 47.6 | 418 |
| Phenyl-substituted compound at 18-position | 88.3 | 407 |

The 9- and 18-positions have large dihedral angles. That is, the substitution positions highly suppressing the generation of excimers caused by intermolecular stacking are the 9- and 18-positions.

The phenyl groups at those positions have a dihedral angle of 88° or more, which is substantially perpendicular to the basic skeleton. This shows that these substitution positions are most suitable for suppressing the generation of excimers. These substitution positions are positions at which the conjugation does not easily spread due to the substantially perpendicular arrangement and the emission wavelength does not easily shift to longer wavelengths.

From the results above, by introducing substituents at the 9- and 18-positions, intermolecular stacking is suppressed and thus the organic compound according to the present invention is obtained as a light-emitting material that does not easily generate excimers.

Herein, the above-described "perpendicular" means that the plane of the substituent introduced at the 9- or 18-position is perpendicular to the plane of the basic skeleton. Examples of the substituent introduced at the 9- or 18-position include a naphthyl group, an indenyl group, a biphenyl group, a terphenyl group, a fluorenyl group, and a tertiary butyl group in addition to the phenyl group.

The peak emission wavelength of the organic compound according to the present invention can be adjusted to a desired wavelength, for example, by introducing a substituent. A substituent can be introduced at a substitution position suitable for the shift to longer wavelengths, the position being selected from the 1- to 8-positions and the 10- to 17-positions, that is, a position other than the 9- and 18-positions of the organic compound according to the present invention. This is because the 9- and 18-positions have little effect on a change in wavelength.

Absorption values (S1) obtained when different bonding positions between the basic skeleton and the phenyl group are employed are compared with each other. From the absorption values, the change in the peak emission wavelength of the substituent can be predicted.

Table 1 shows the results. When a compound having a phenyl group at the 9- or 18-position of the basic skeleton thereof is compared with a non-substituted compound, the difference in absorption value between the former and the latter is 3 nm or less. On the other hand, the difference between a compound having a phenyl group at a different substitution position and the non-substituted compound is 6 nm or more and 12 nm or less.

In other words, the compound having a phenyl group at the 9- or 18-position has little effect on wavelength. To shift a wavelength to longer wavelengths, a substituent can be introduced at a position selected from the 1- to 8-positions and the 10- to 17-positions.

In the organic compound according to the present invention, by introducing a substituent at a position selected from the 1- to 8-positions and 10- to 17-positions, the wavelength is shifted to longer wavelengths and a light-emitting material suitable for green to red light emission can be obtained.

Specific examples of the organic compound according to the present invention are shown below. However, the present invention is not limited thereto.

[Chem. 9]

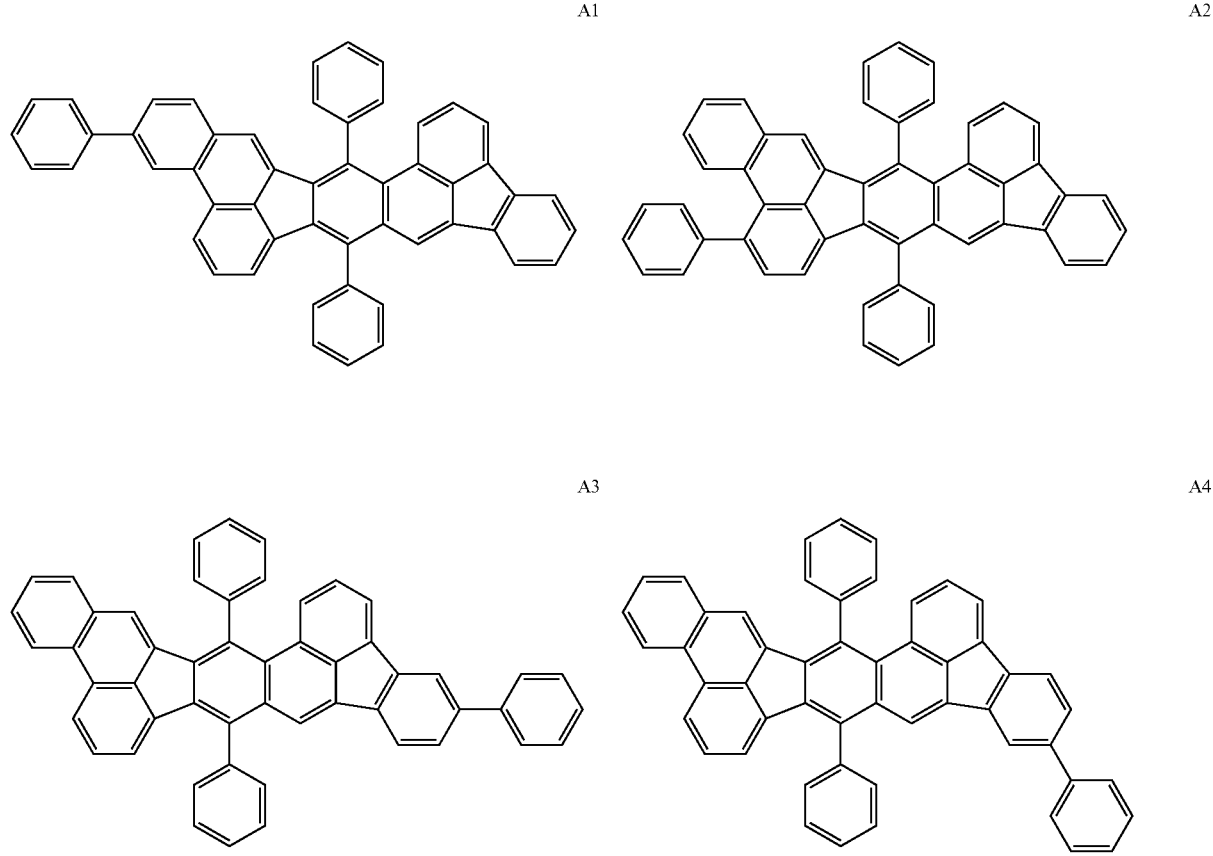

-continued
A5
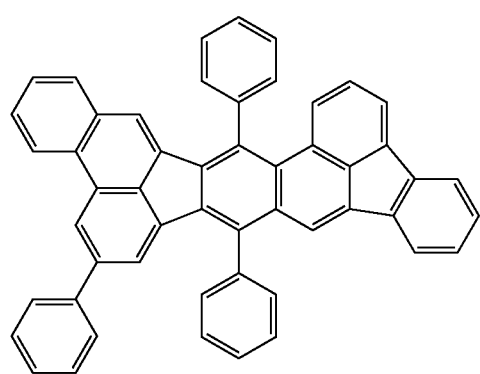
A6
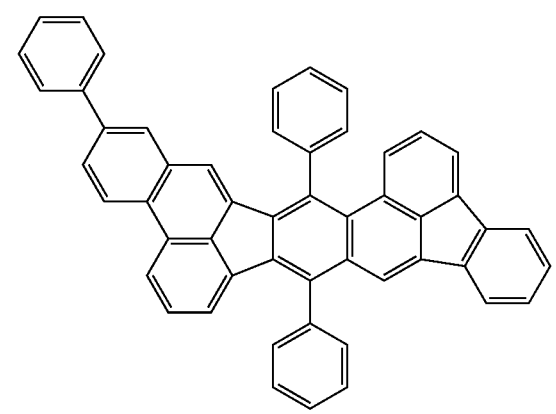
A7
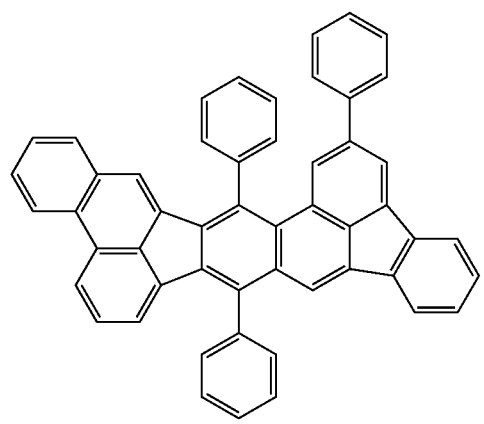
A8
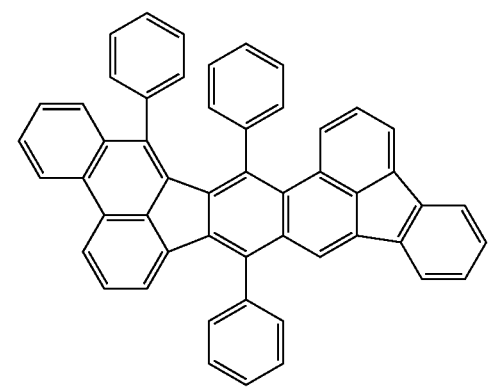
A9
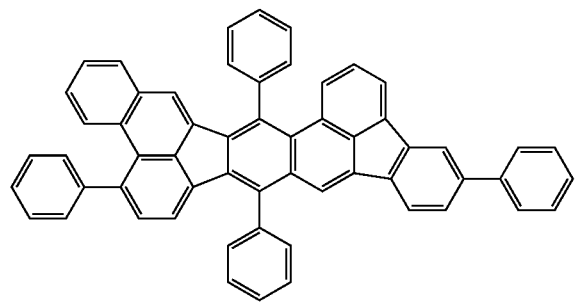
A10
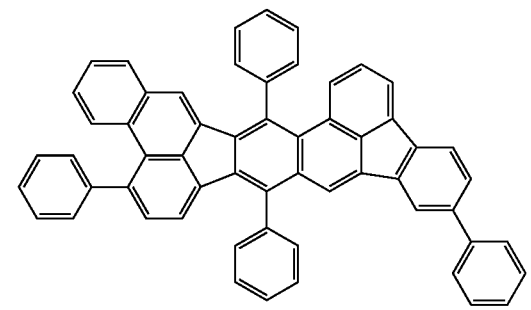
A11
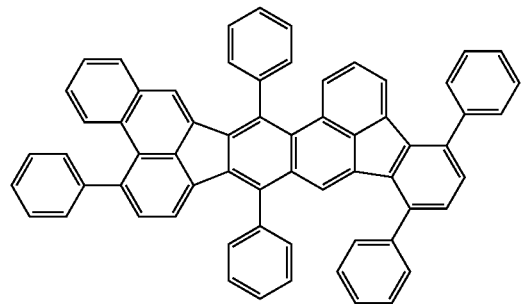
A12
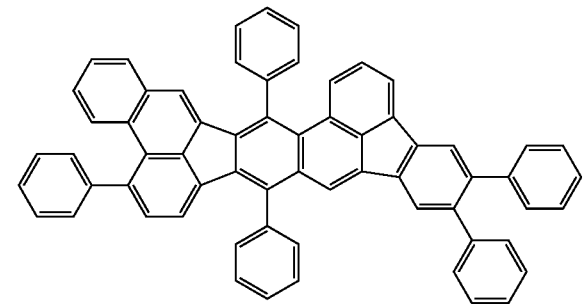

-continued
A13
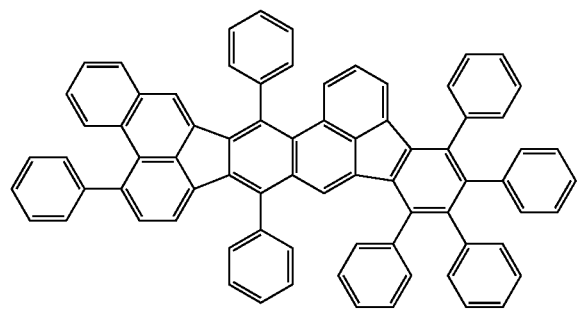
A14
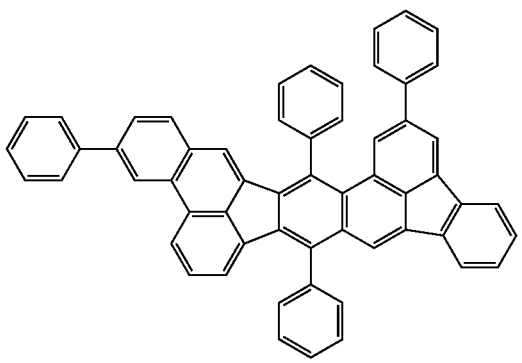
A15
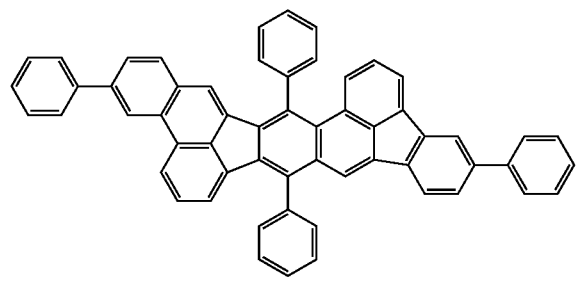
A16
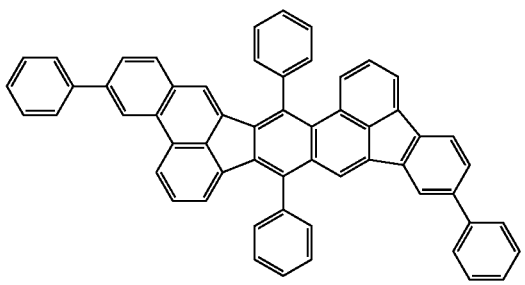
A17
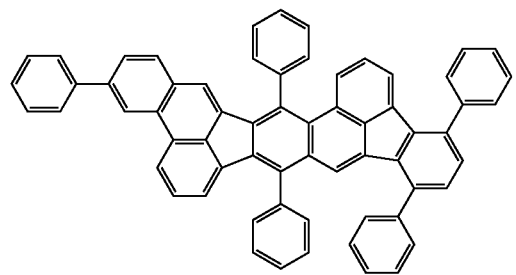
A18
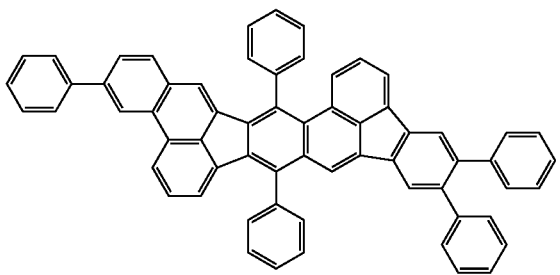
A19
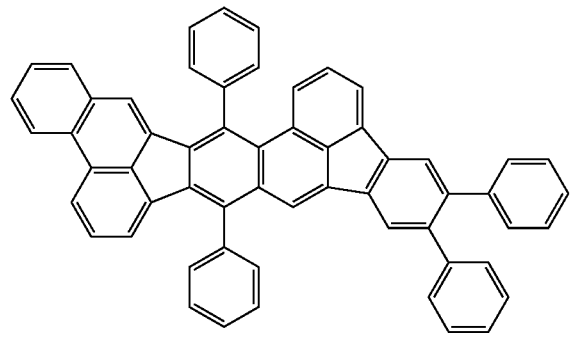

-continued
[Chem. 10]
A20
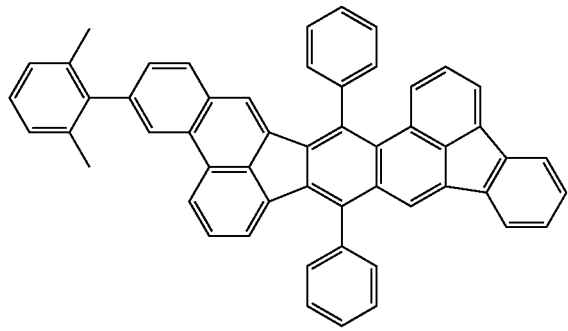
A21
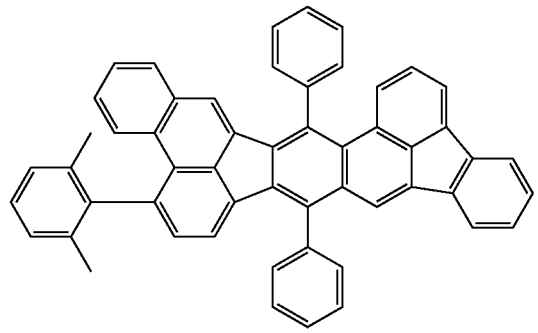
A22
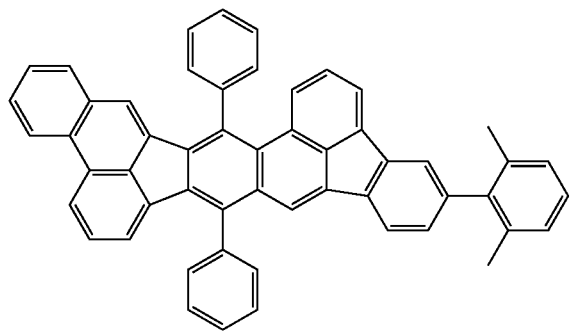
A23
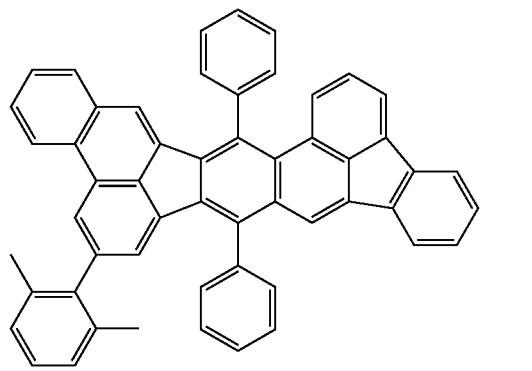
A24
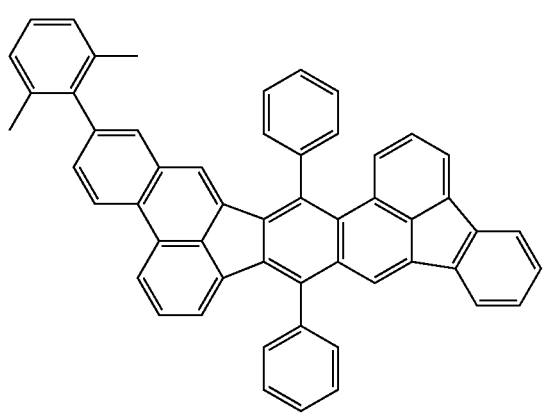
A25
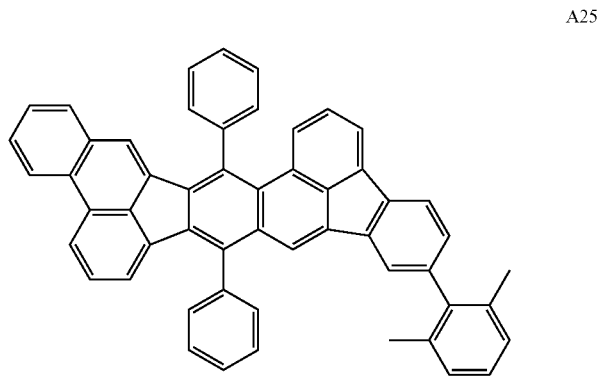
A26
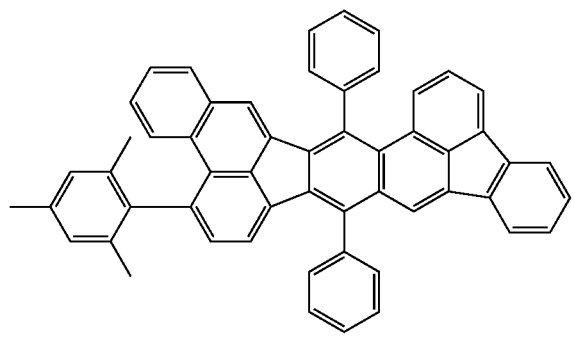

-continued
A27
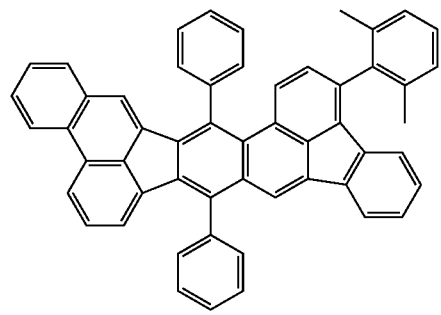
A28
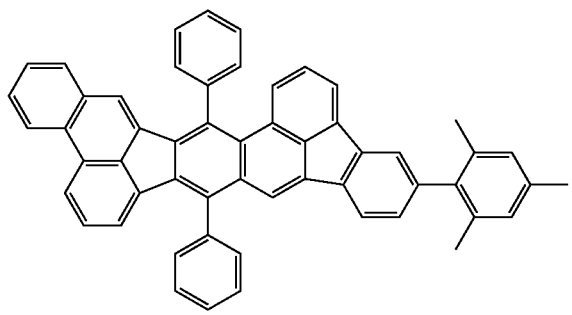
A29
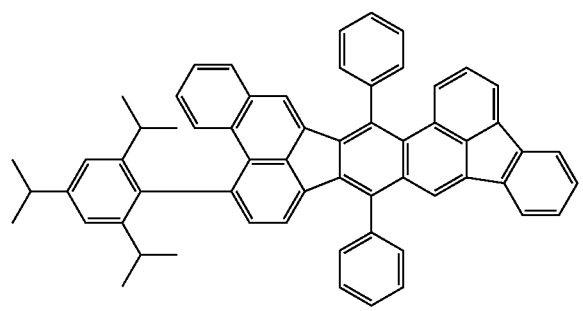
A30
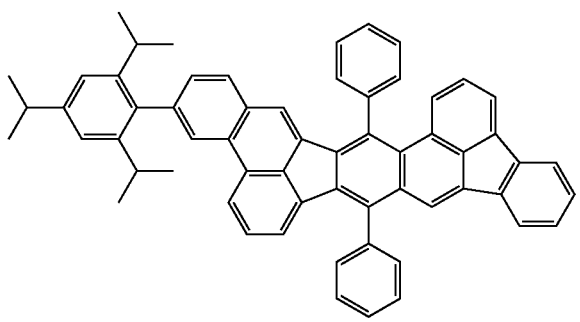
A31
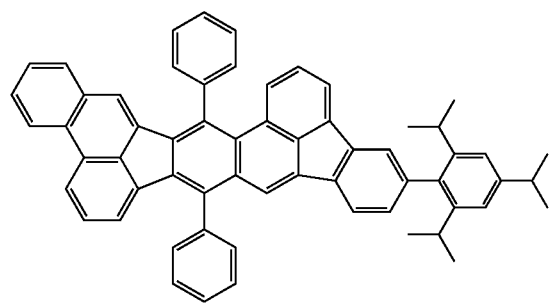
A32
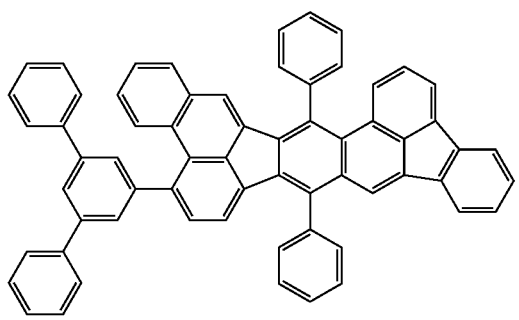
A33
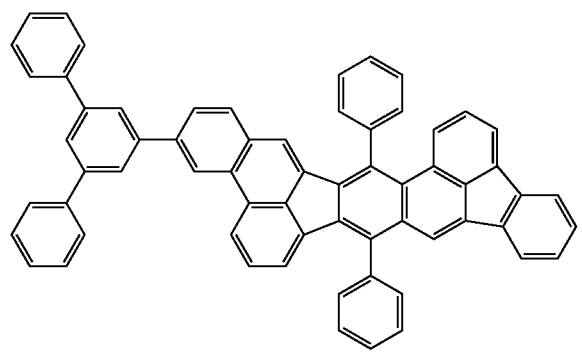
A34
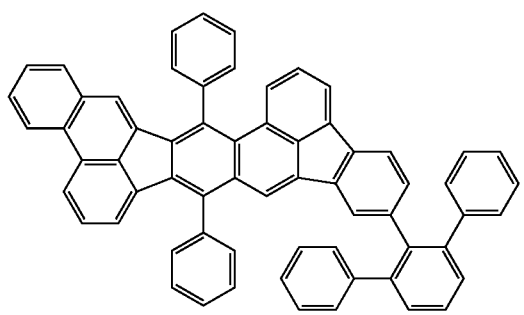

-continued
A35
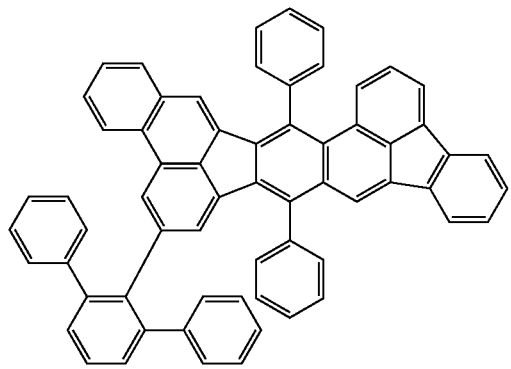
A36
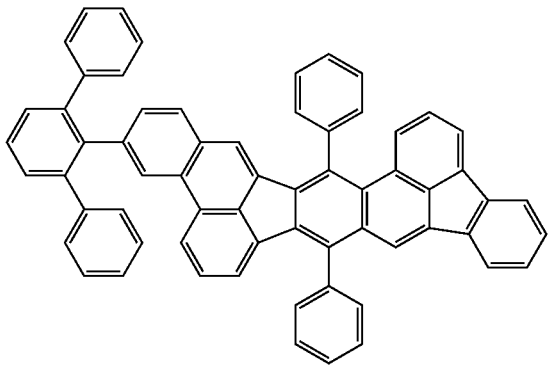
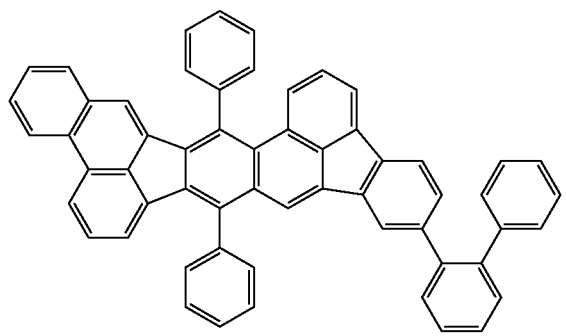
[Chem. 11]
A38
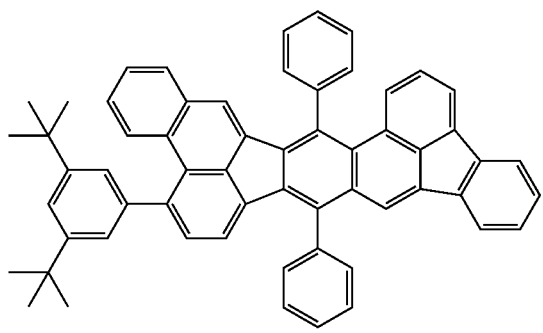
A39
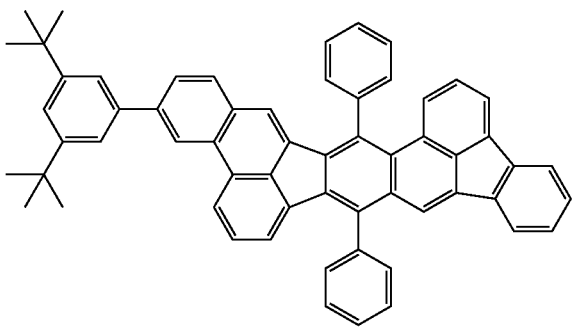
A40
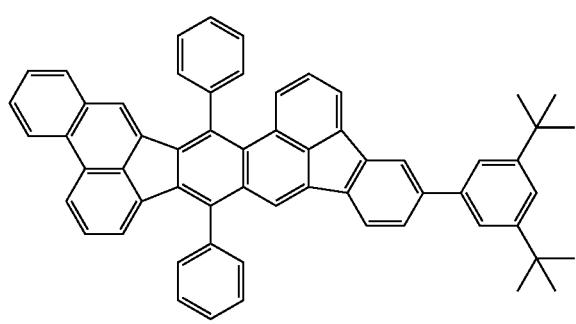

-continued
A41
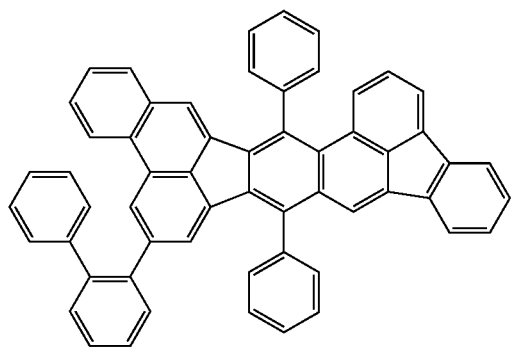
A42
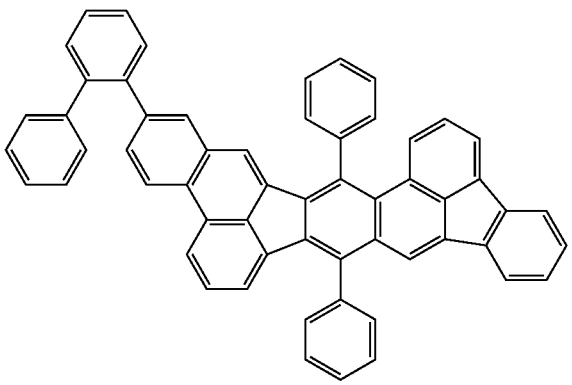
A43
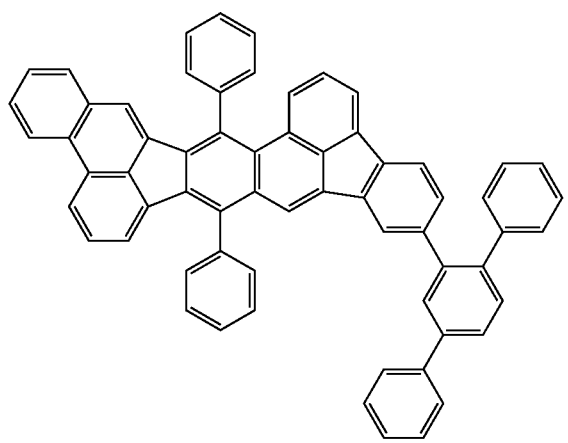
A44
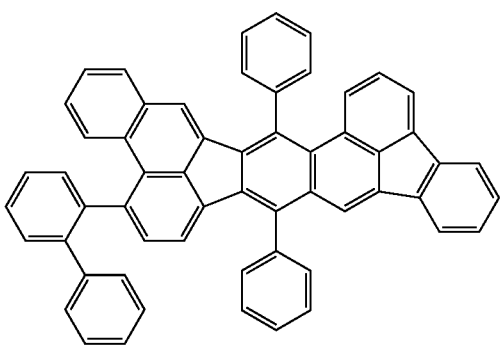
A45
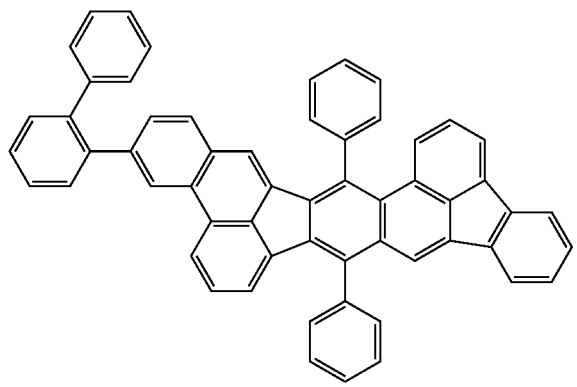
A46
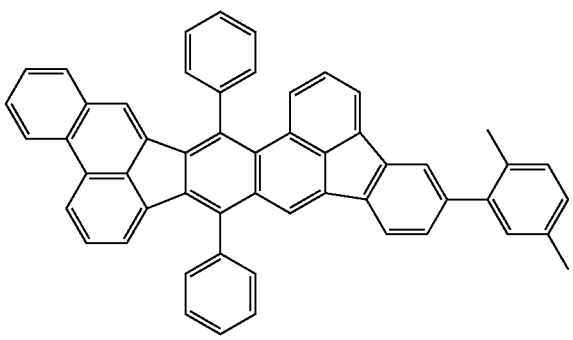
A47
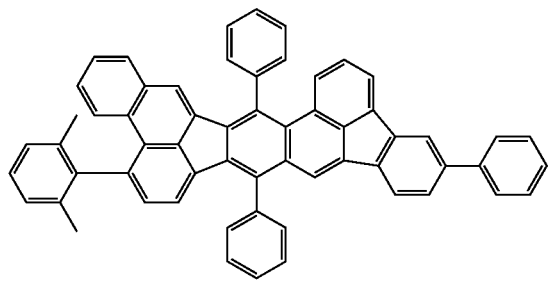
A48
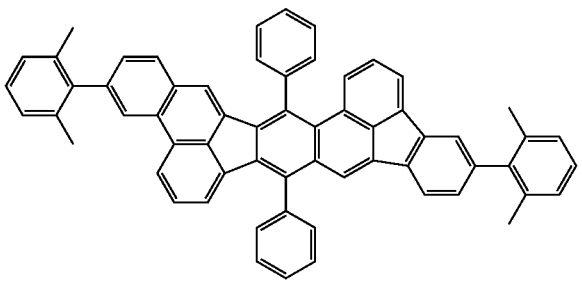

-continued
A49
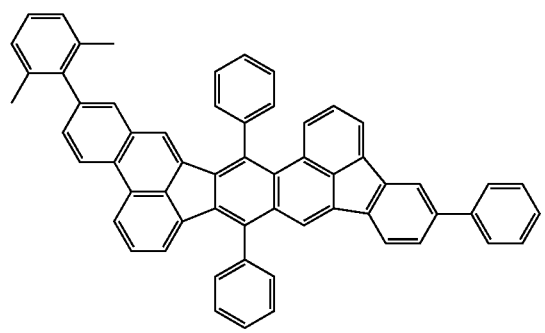
A50
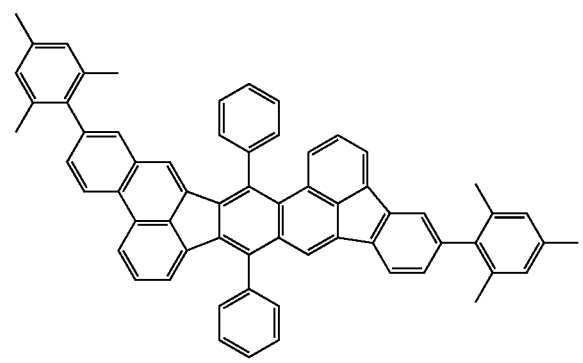
A51
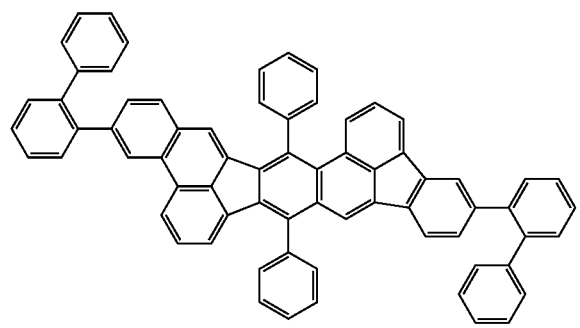
A52
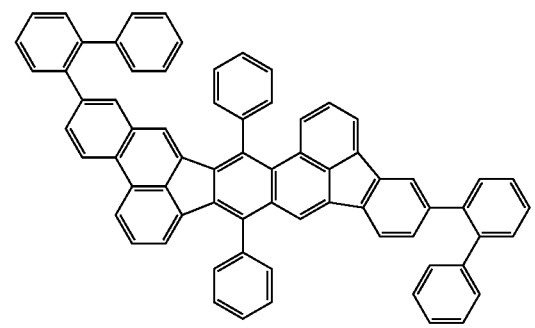
A53
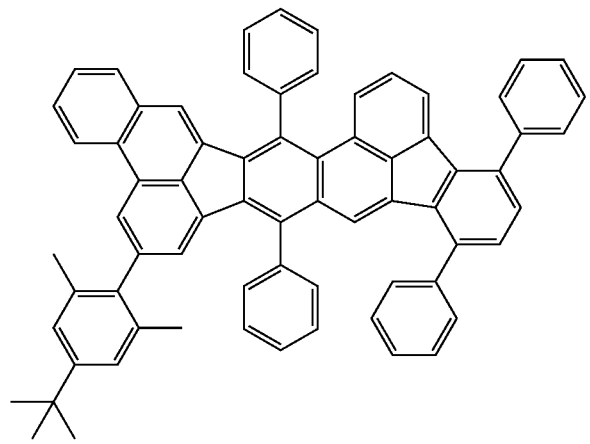
A54
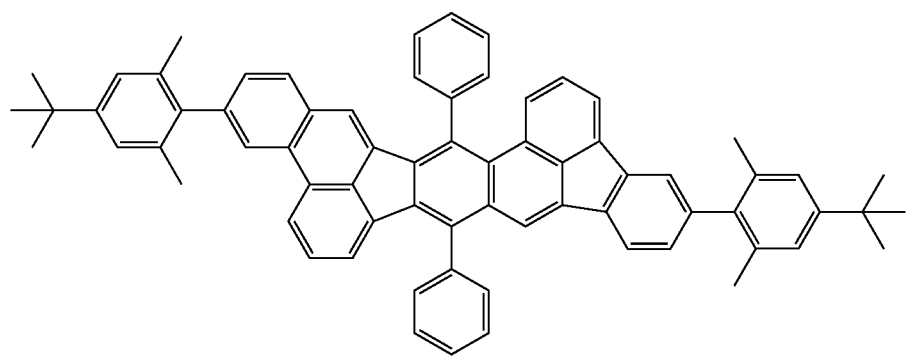

A55
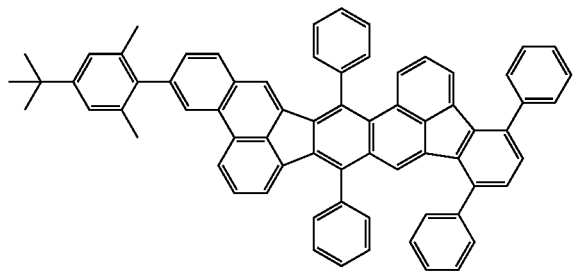
[Chem. 12]
A56
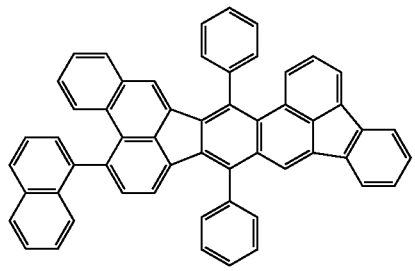
A57
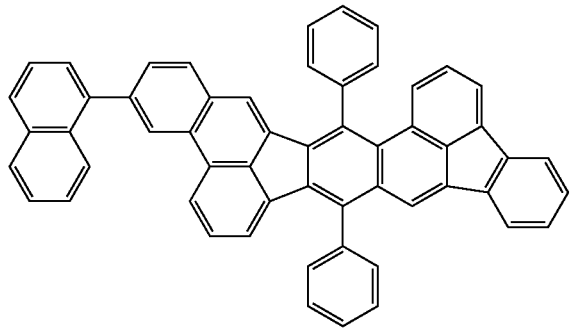
A58
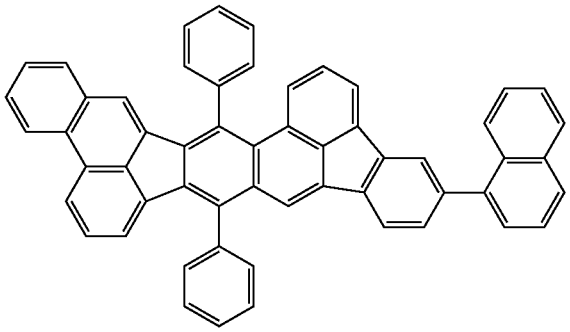
A59
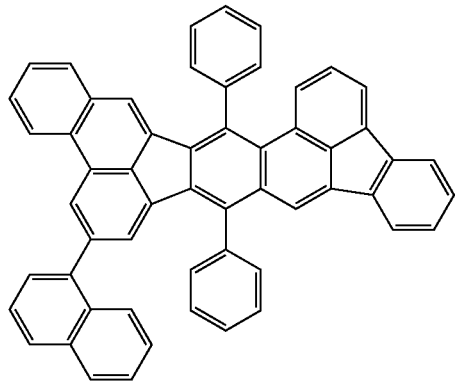
A60
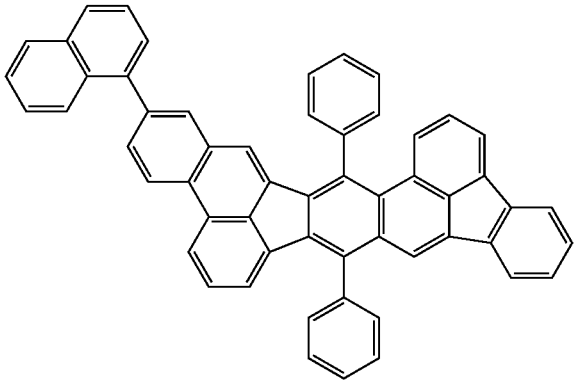

-continued
A61
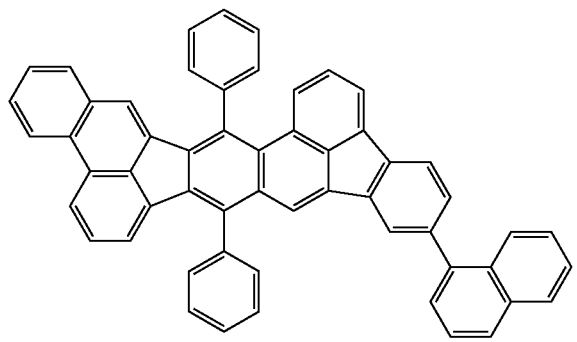
A62
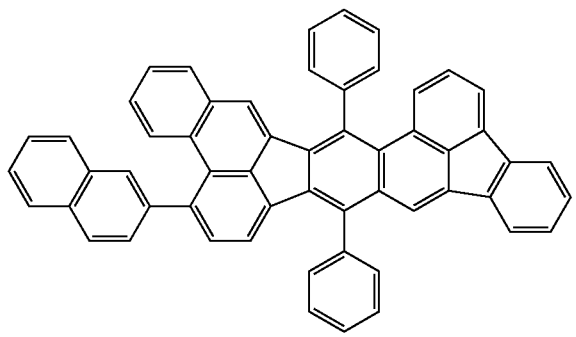
A63
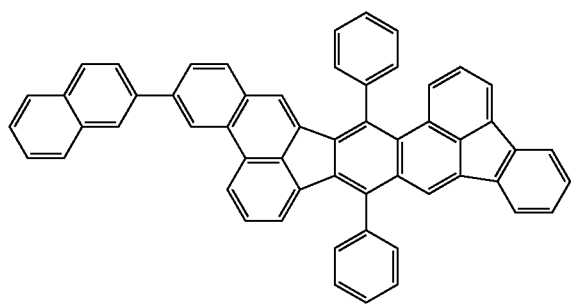
A64
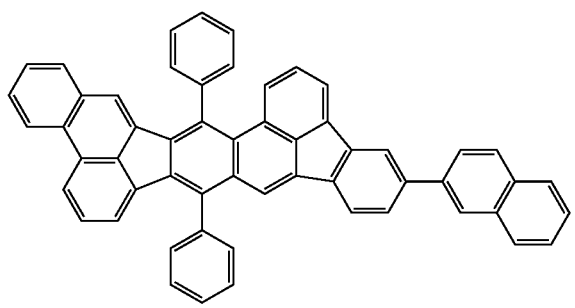
A65
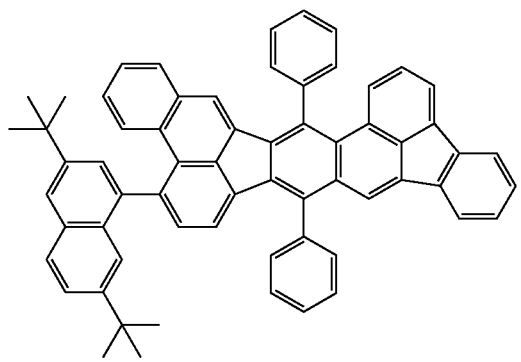
A66
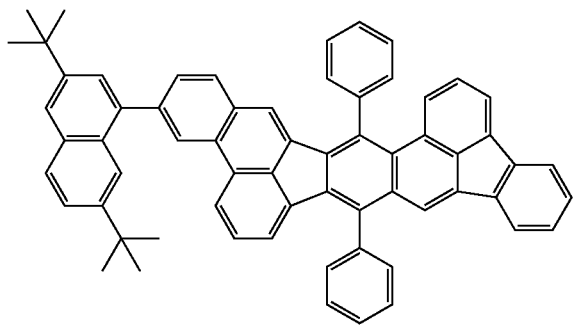
A67
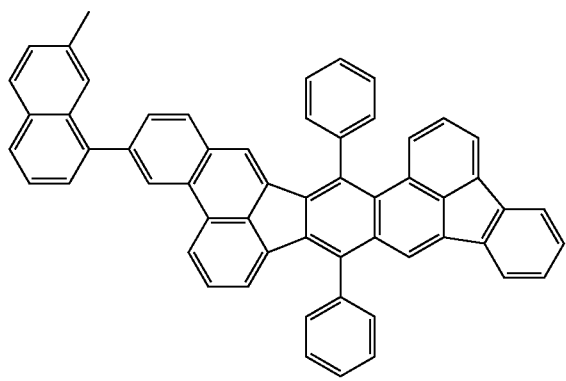
A68
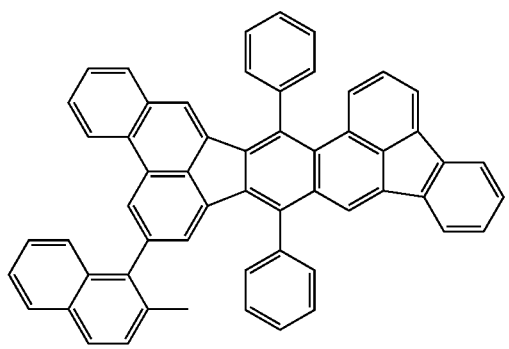

-continued
A69
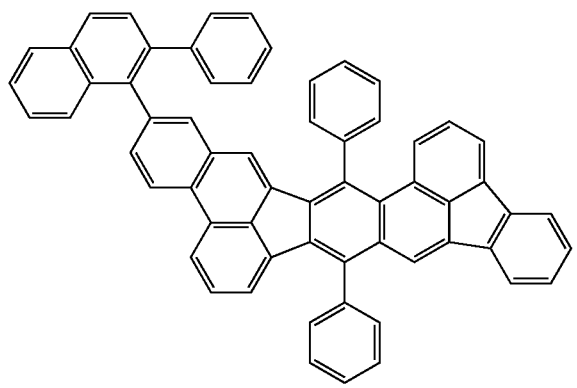
A70
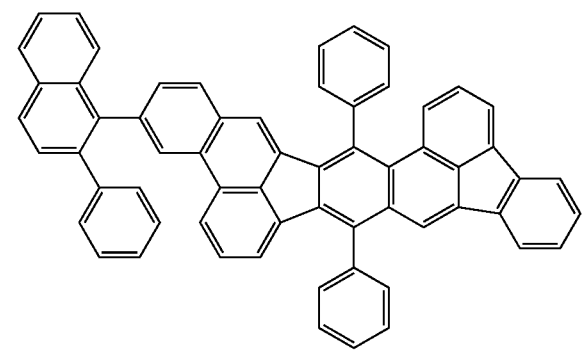
A71
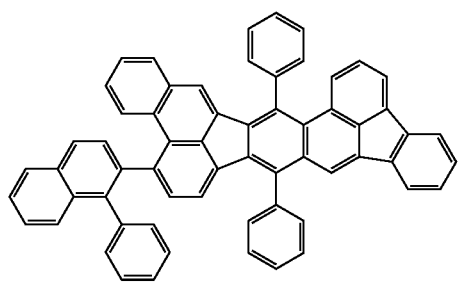
A72
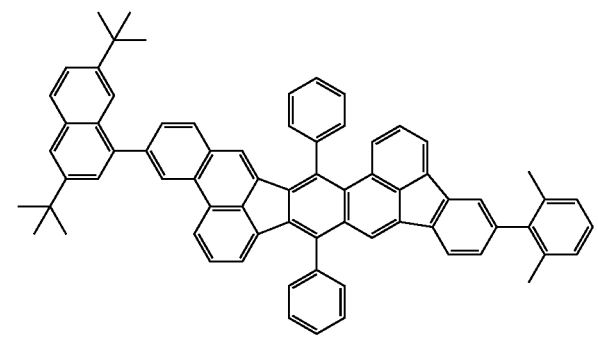
A73
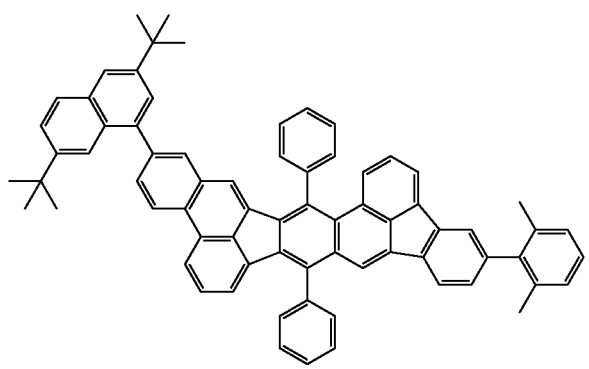
[Chem. 13]
A74
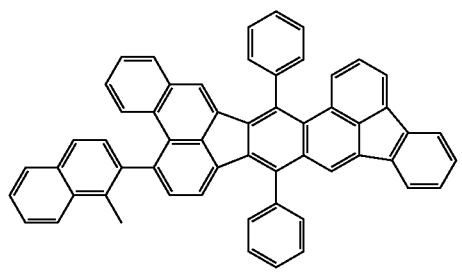
A75
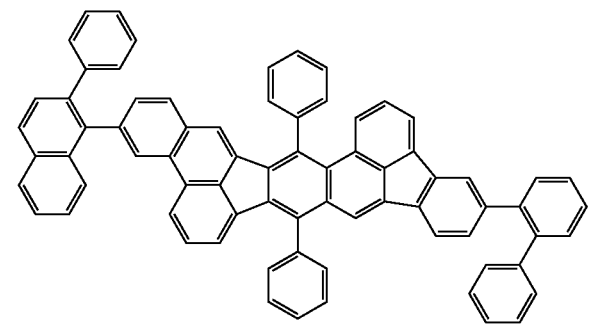

-continued
A76
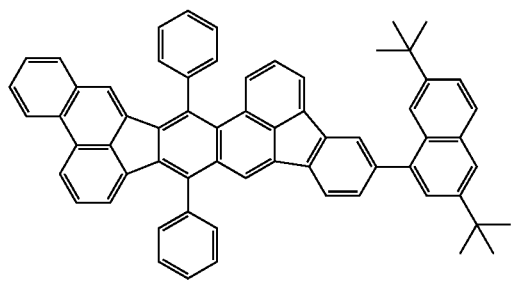
A77
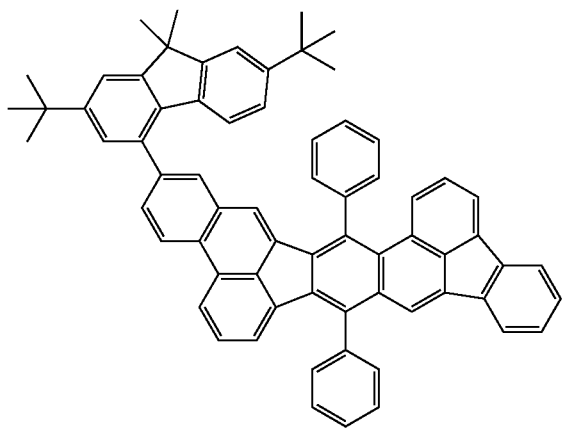
A78
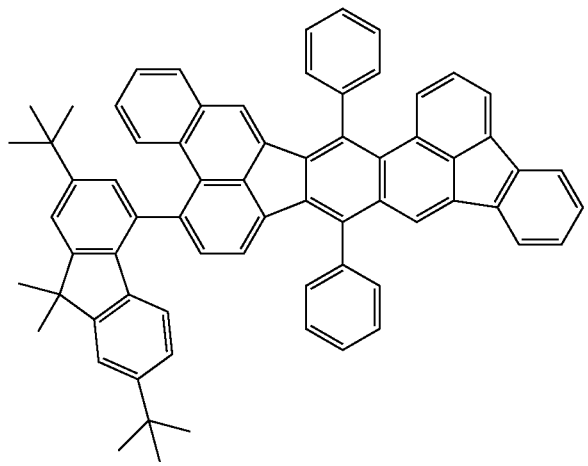
A79
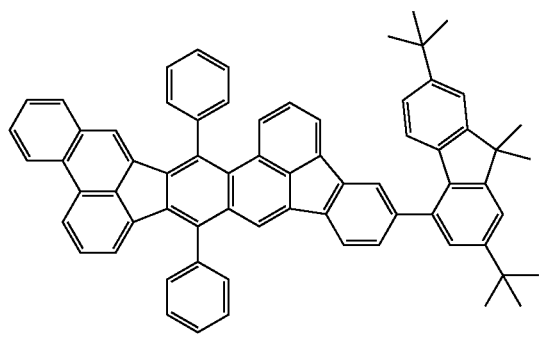
A80
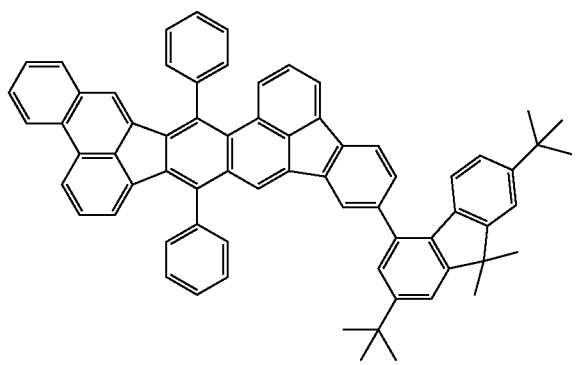
A81
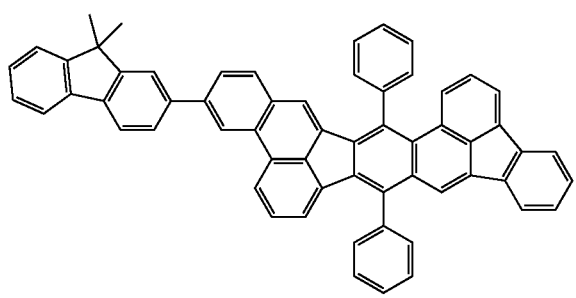
A82
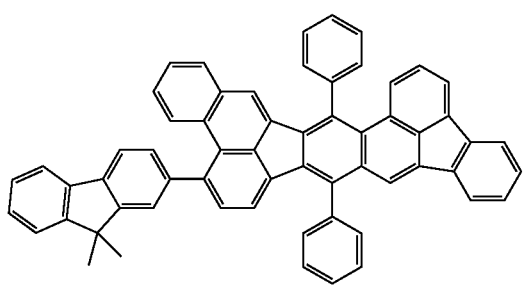

-continued
A83
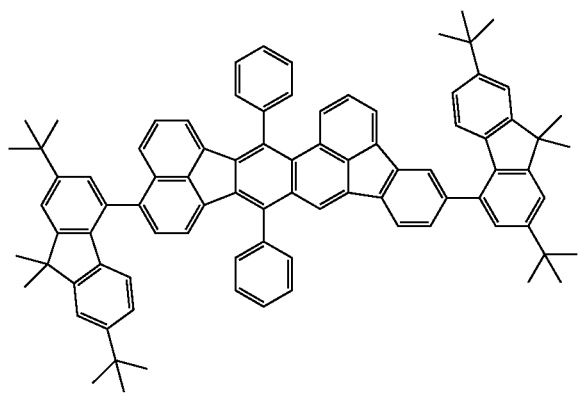
A84
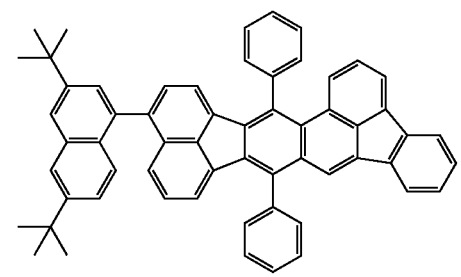
A85
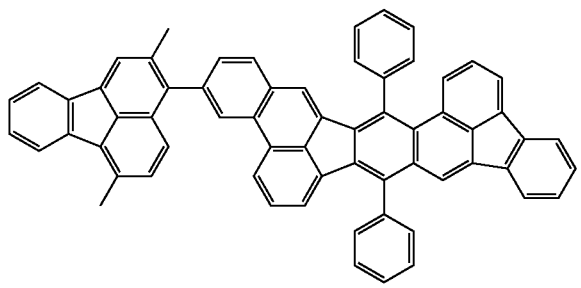
A86
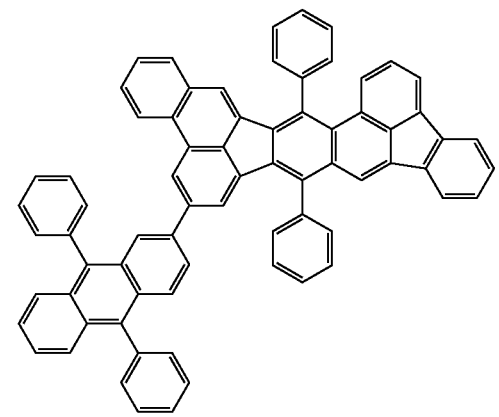
A87
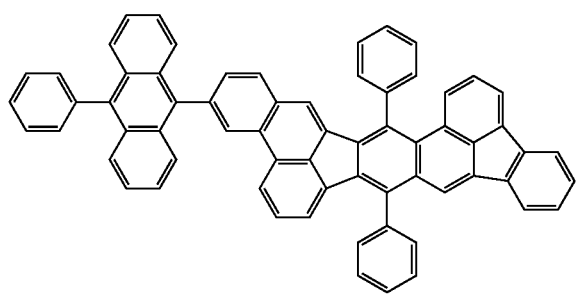
A88
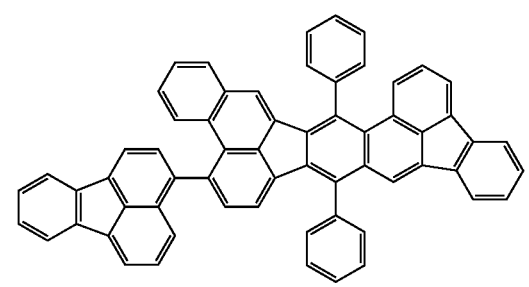
A89
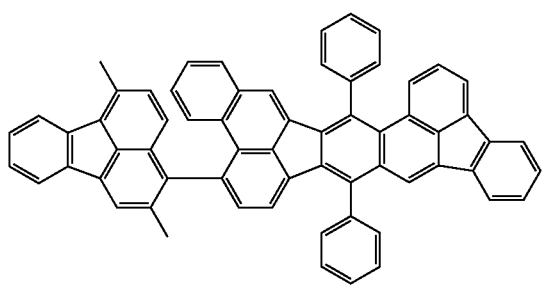
A90
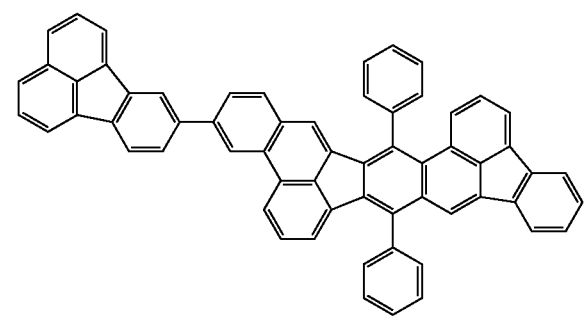

A91
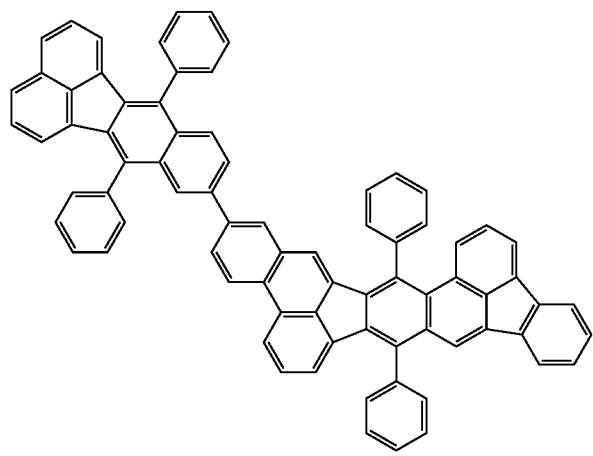
[Chem. 14]
A92
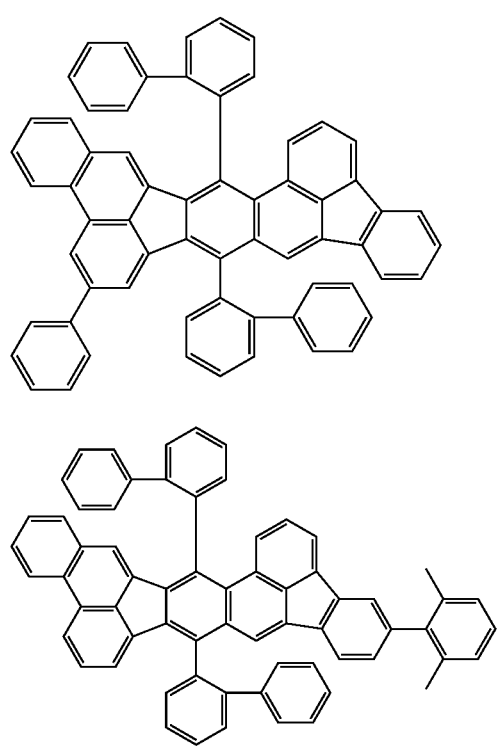
A93
A94
A95
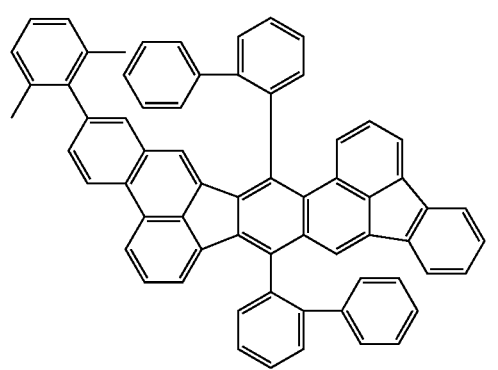
A96
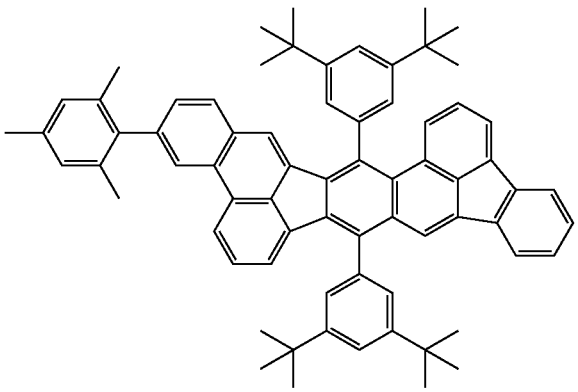

-continued
A97
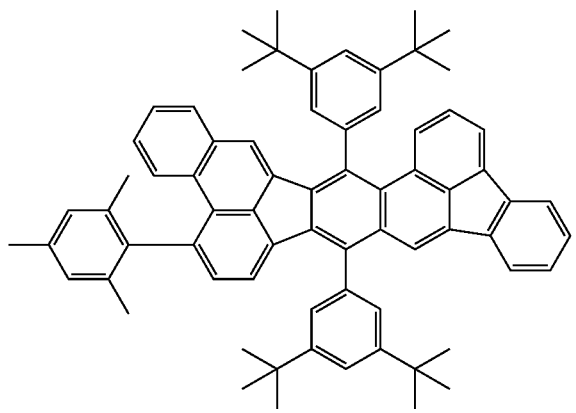
A98
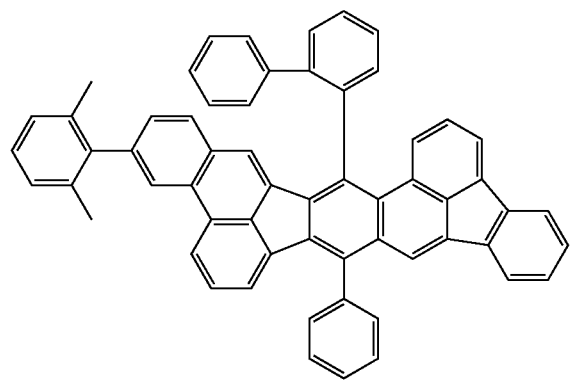
A99
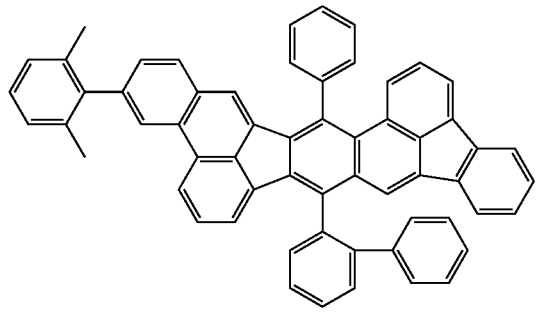
A100
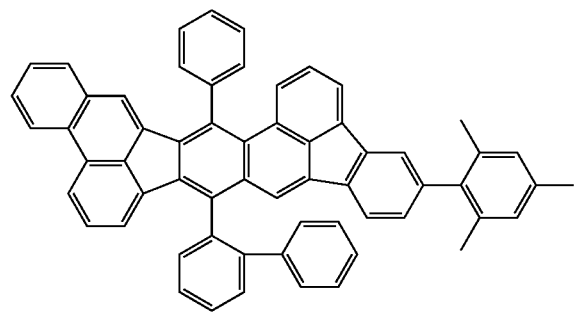
A101
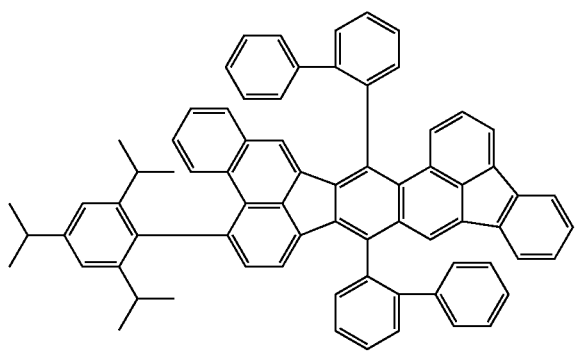
A102
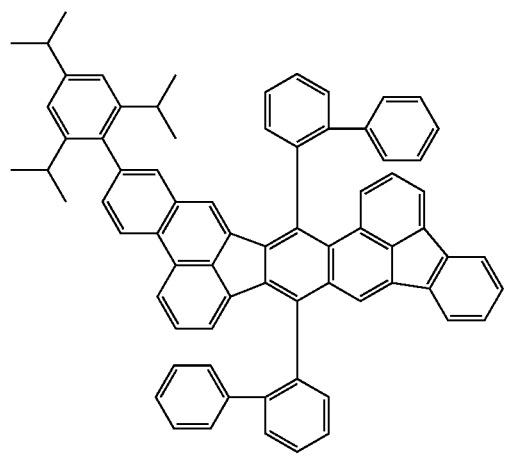

-continued
A103
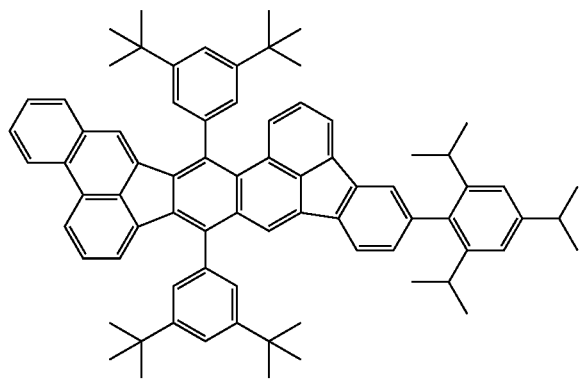
A104
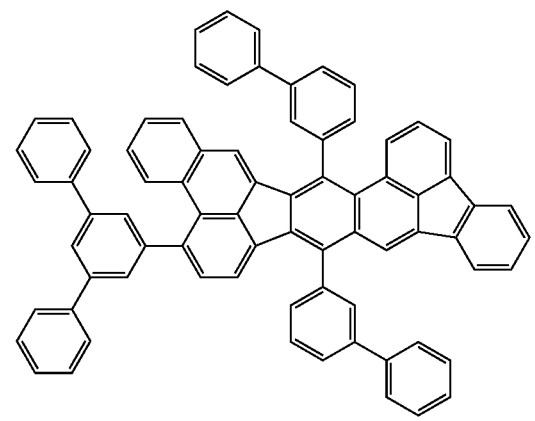
A105
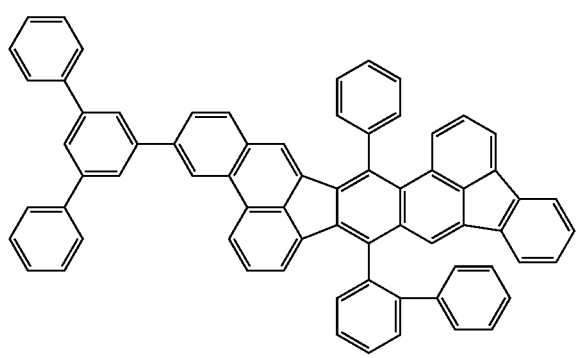
A106
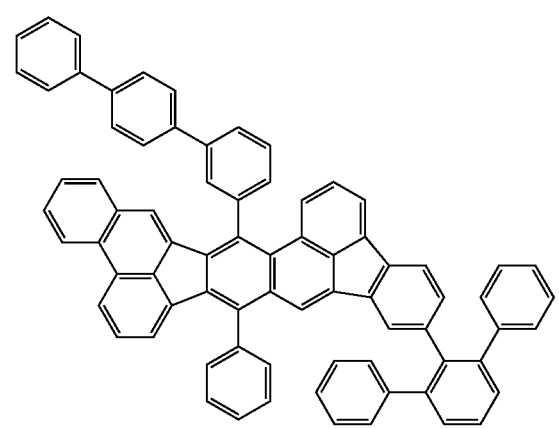
A107
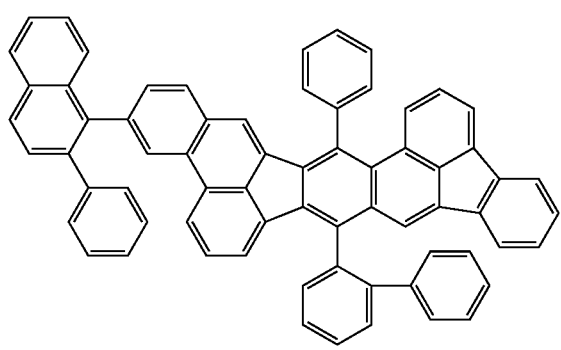
A108
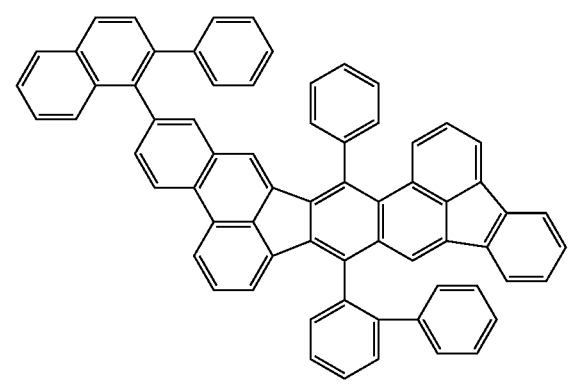
A109
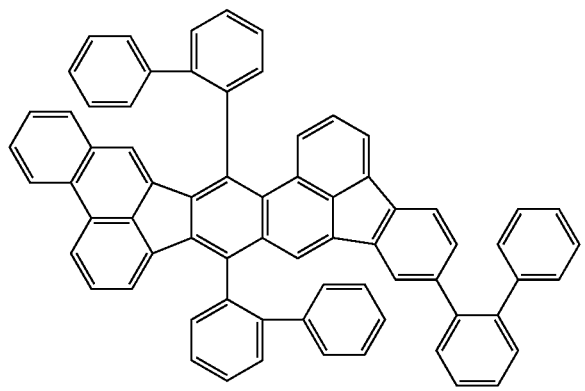

-continued
A110
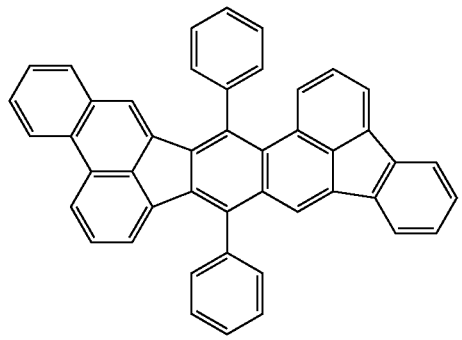
A111
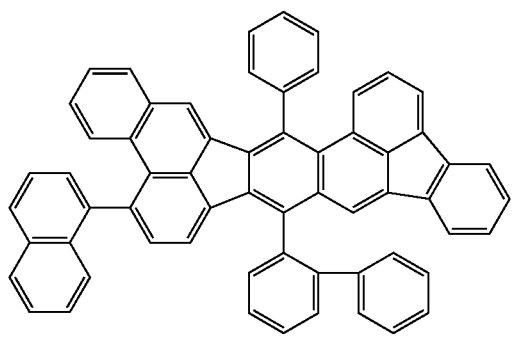
A112
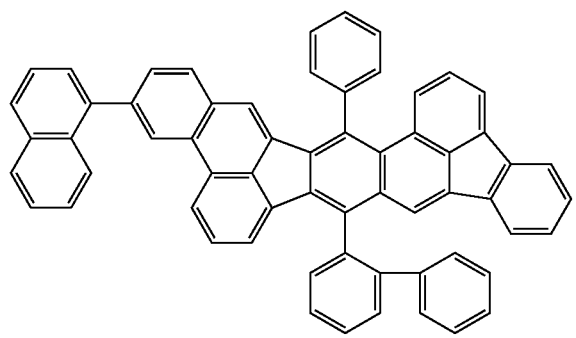
A113
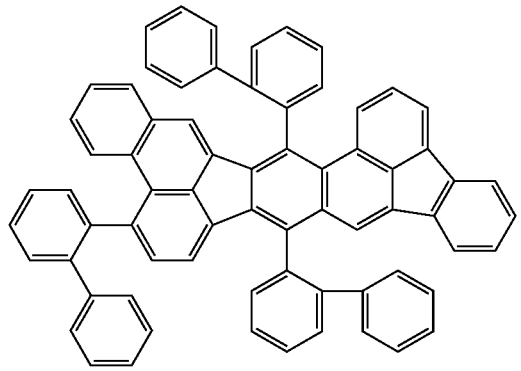
A114
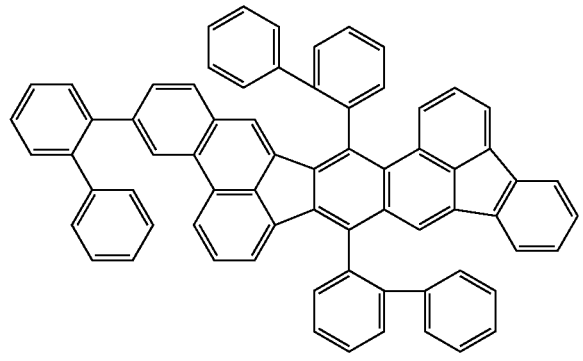
A115
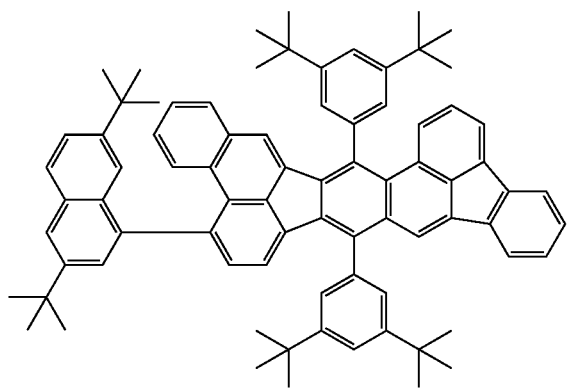
A116
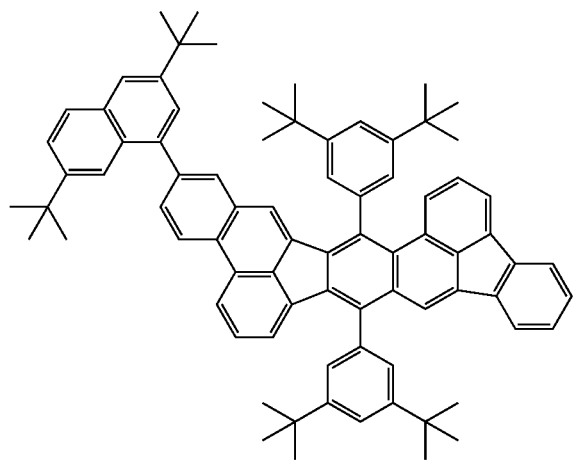

-continued
A117
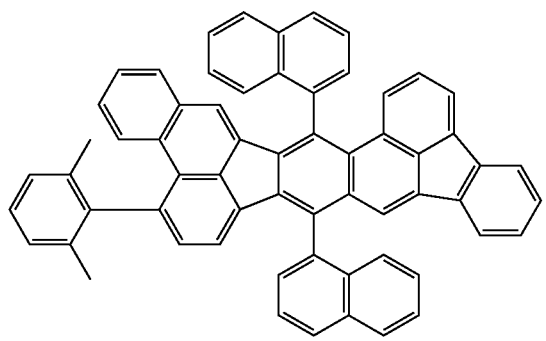
A118
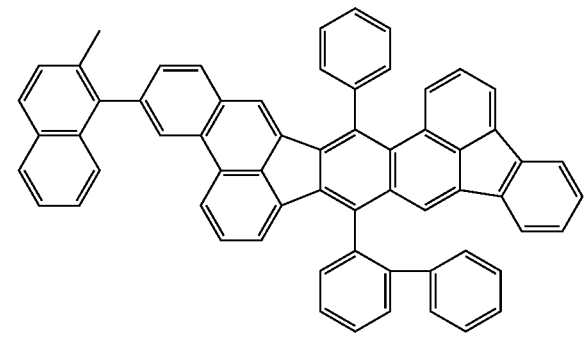
A119
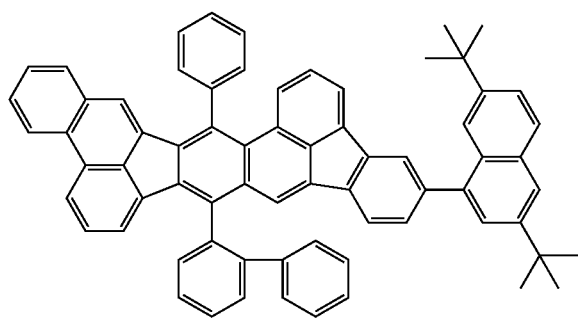
A120
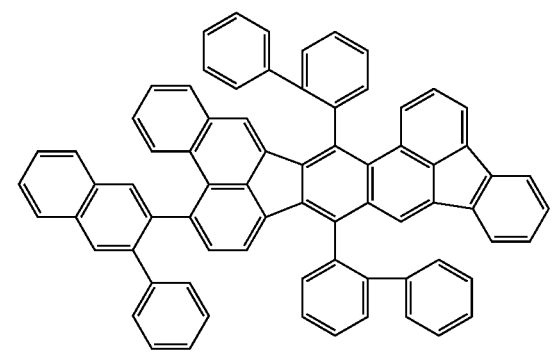
A121
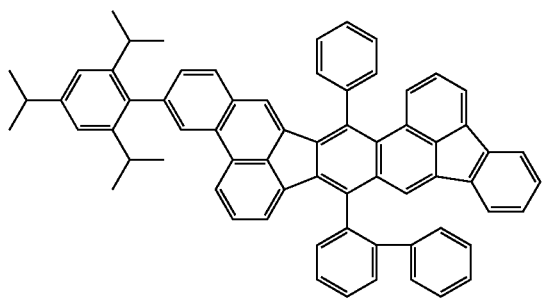
A122
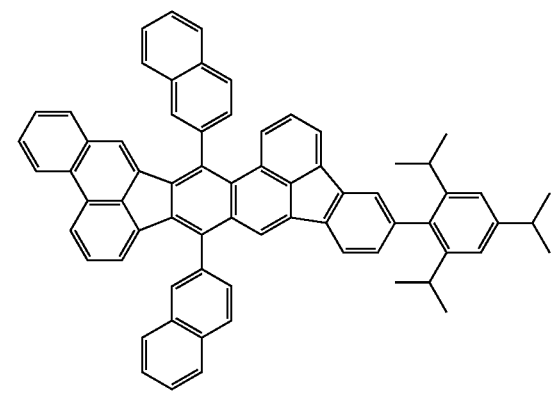
A123
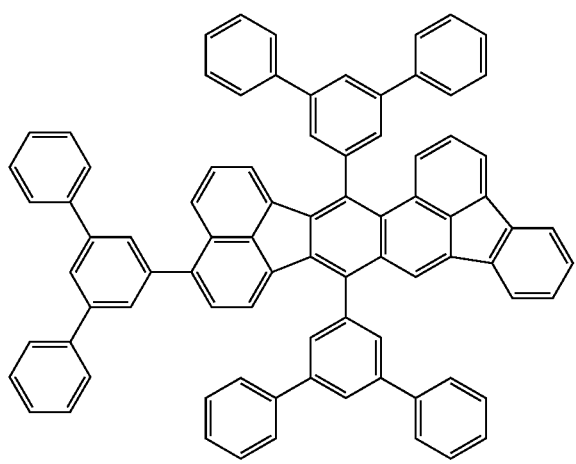
A124
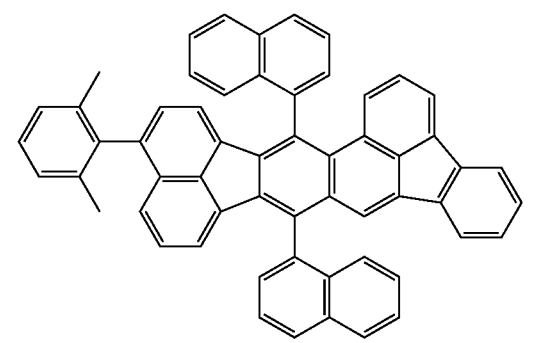

-continued
A125
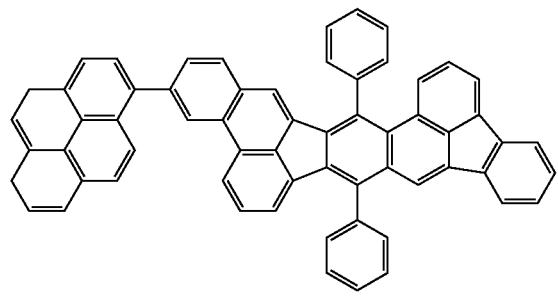
A126
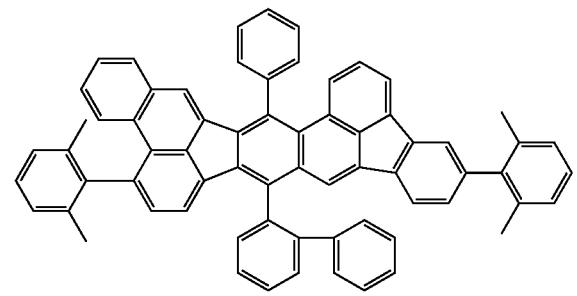
A127
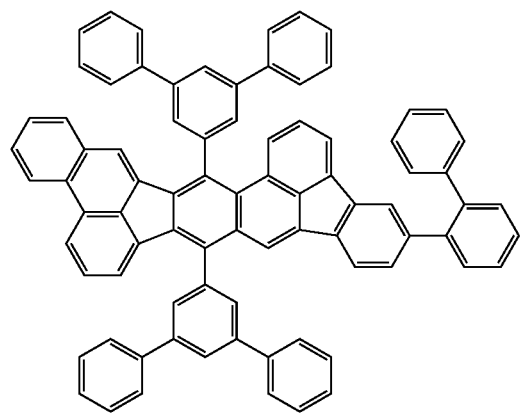
A128
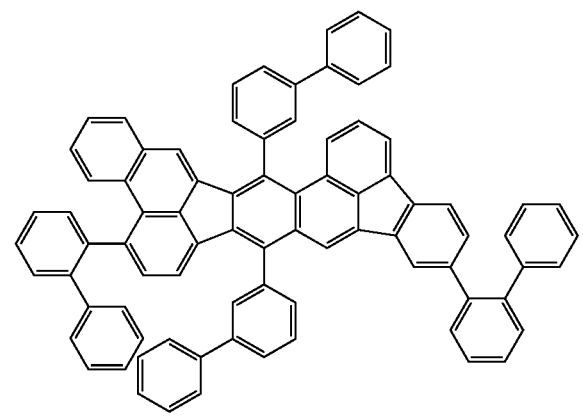
[Chem. 16]
A129
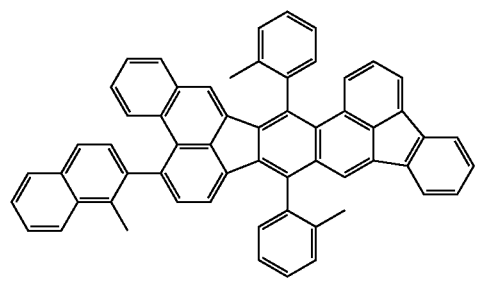
A130
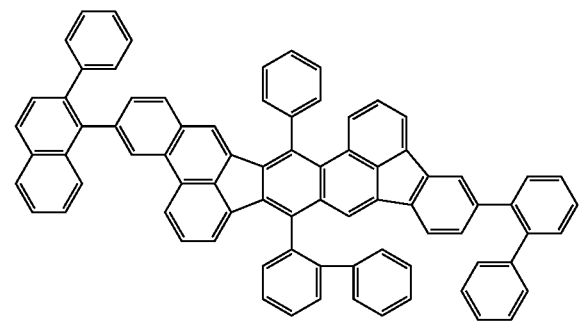
A131
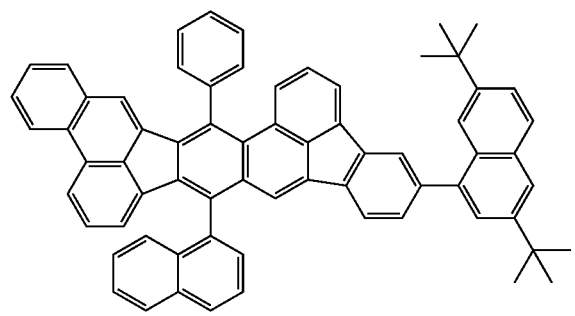
A132
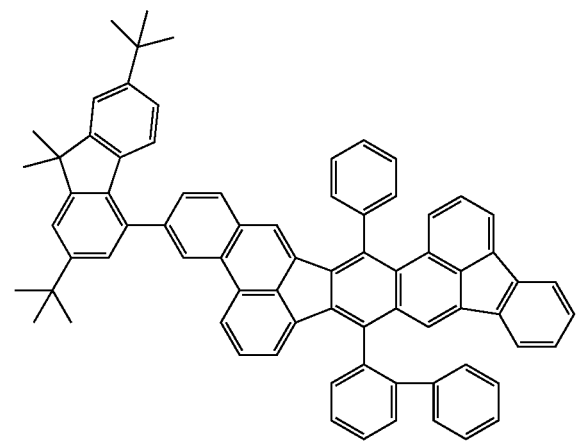

-continued
A133
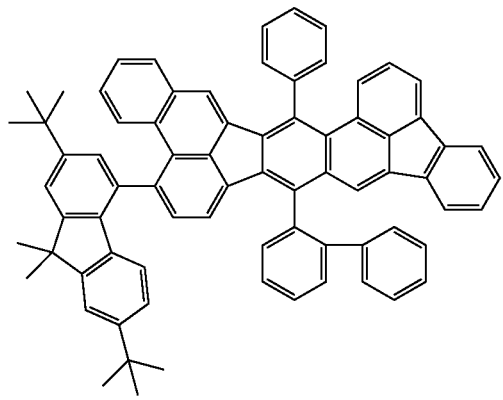
A134
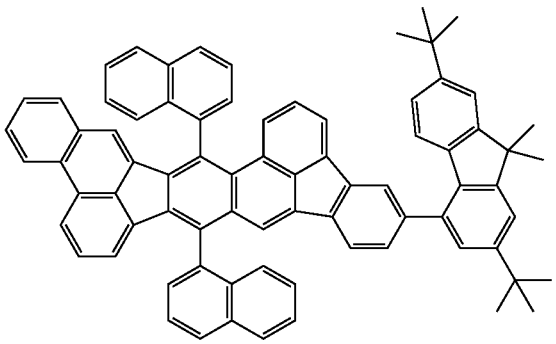
A135
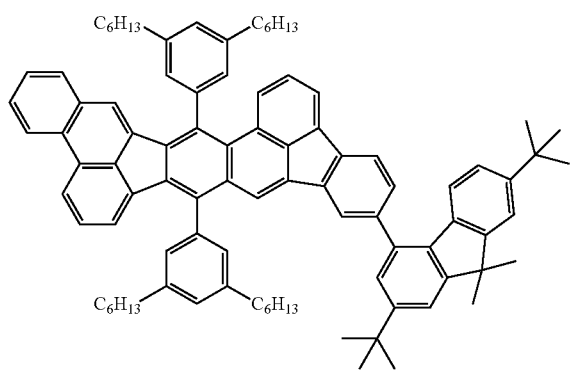
A136
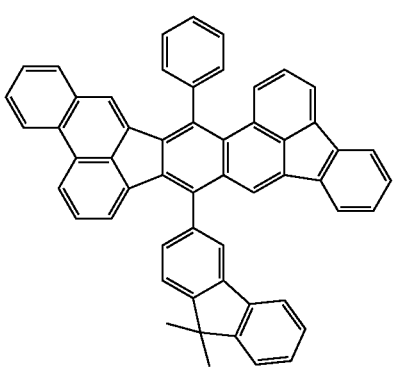
A137
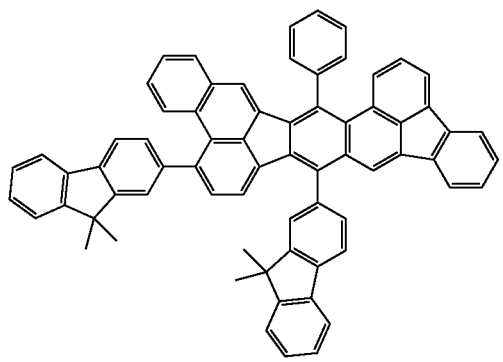
A138
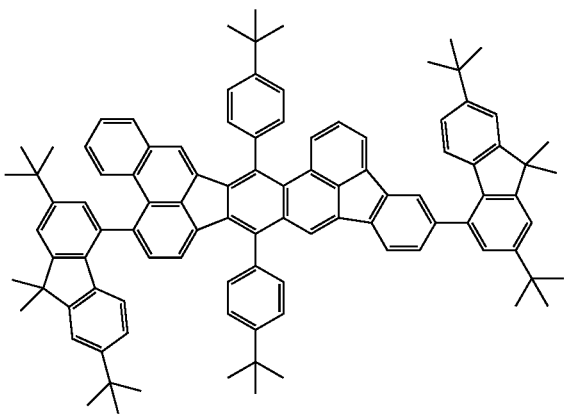
A139
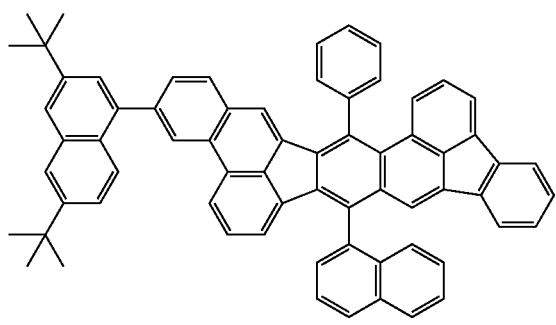
A140
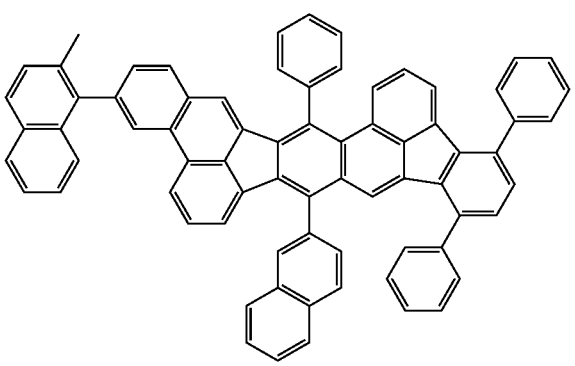

A141
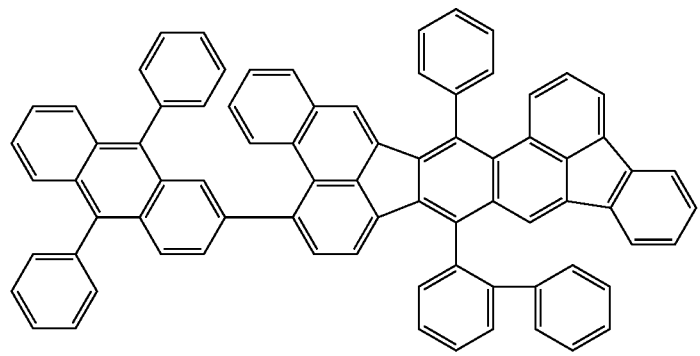
A142
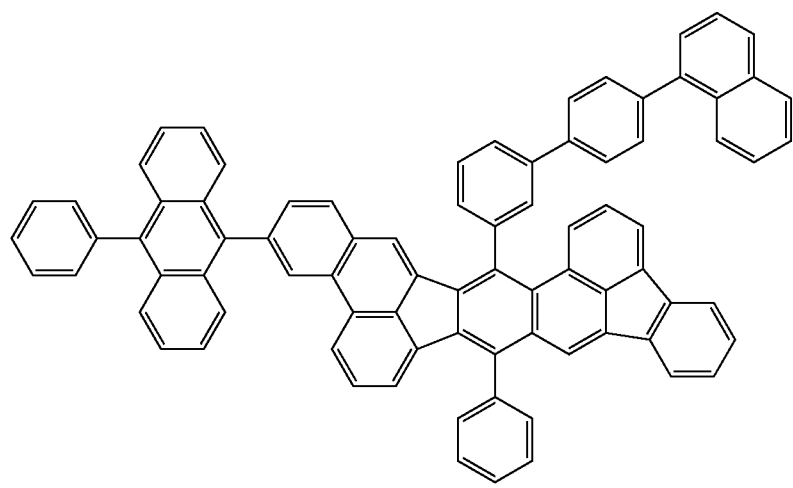
A143
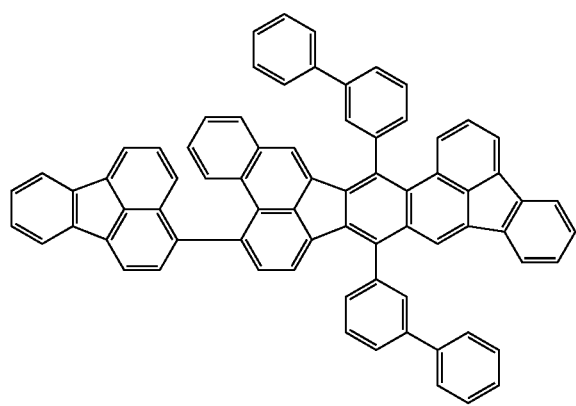
A144
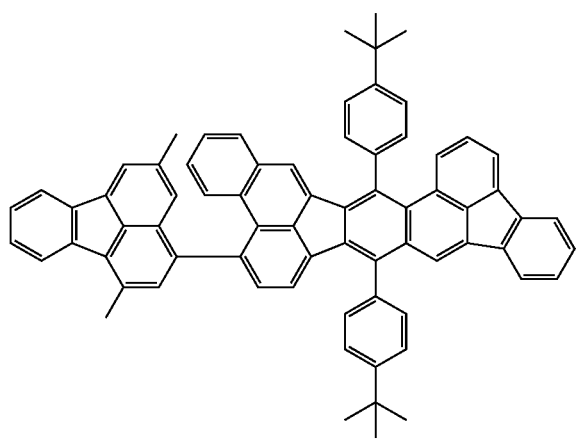

-continued
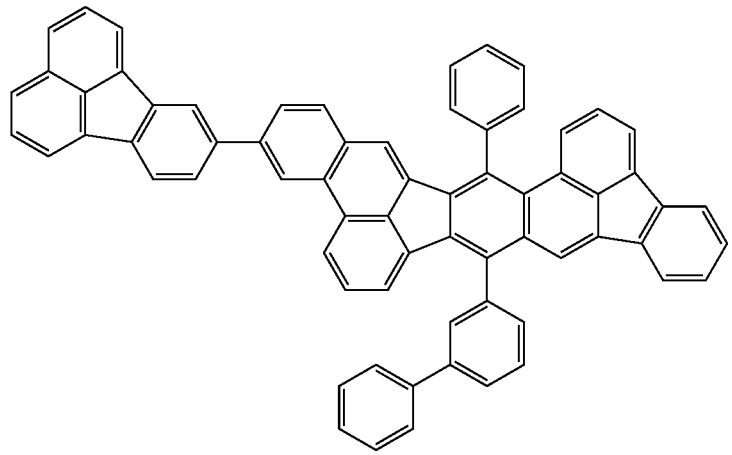
A145
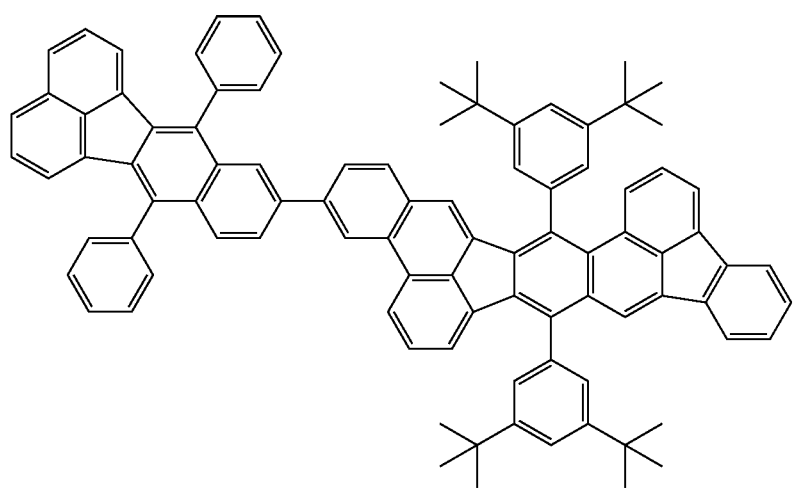
A146
[Chem. 17]
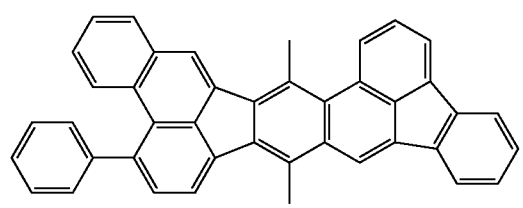
B1
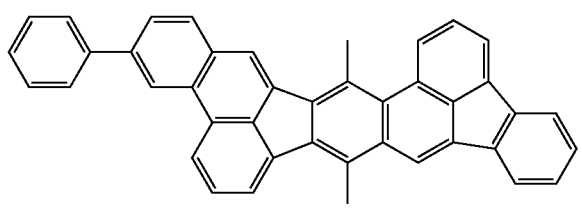
B2
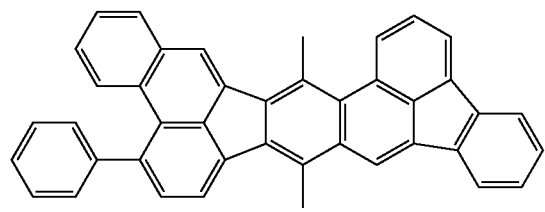
B3
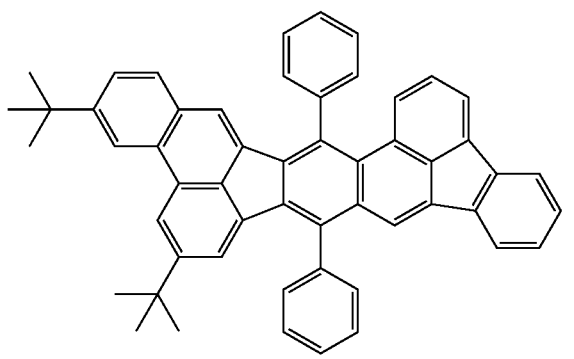
B4

-continued
B5
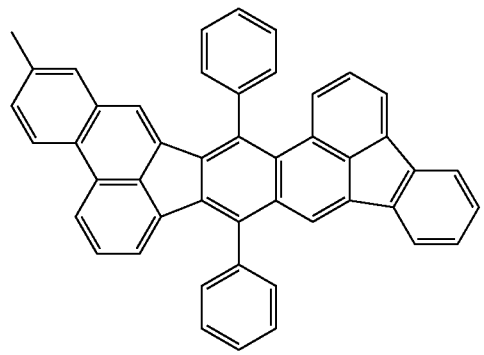
B6
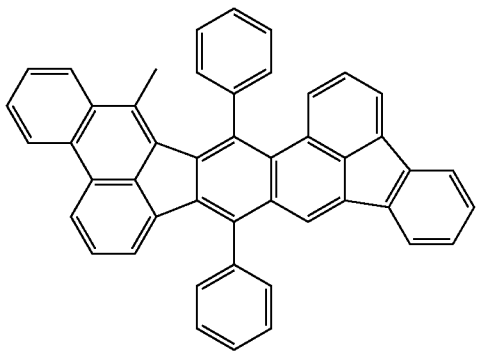
B7
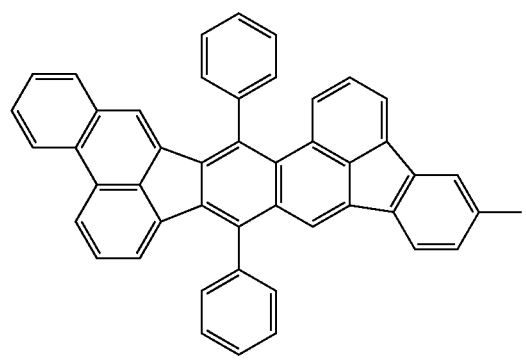
B8
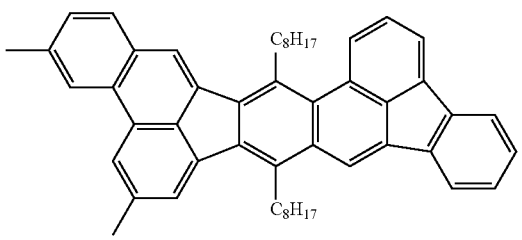
B9
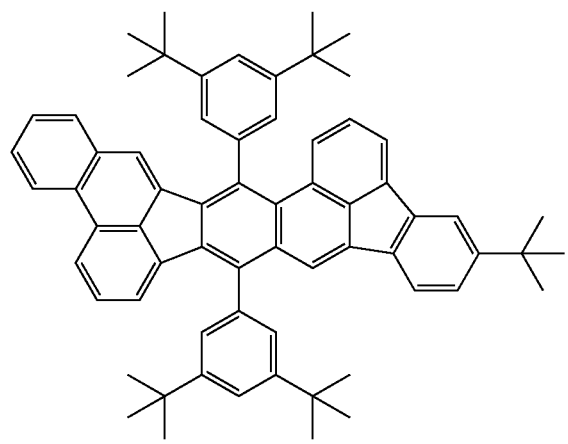
B10
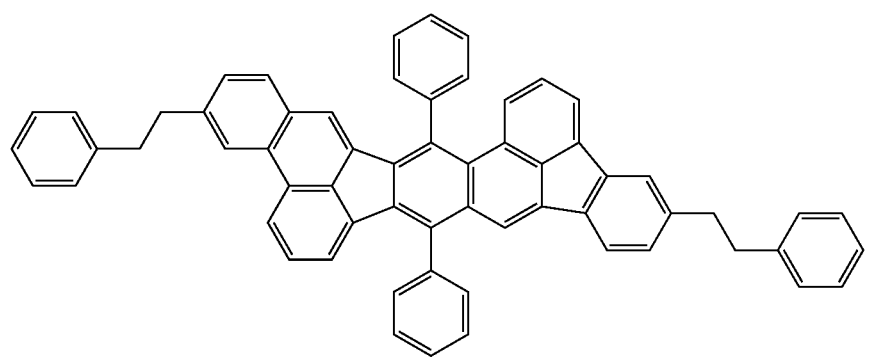

-continued
B11
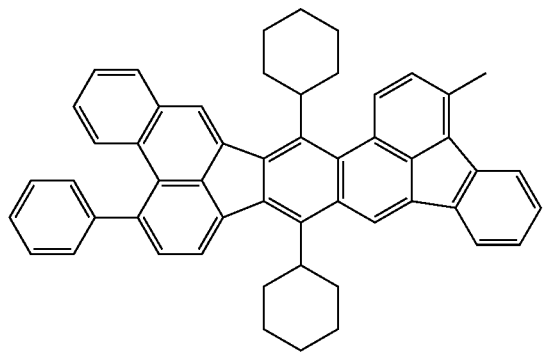
B12
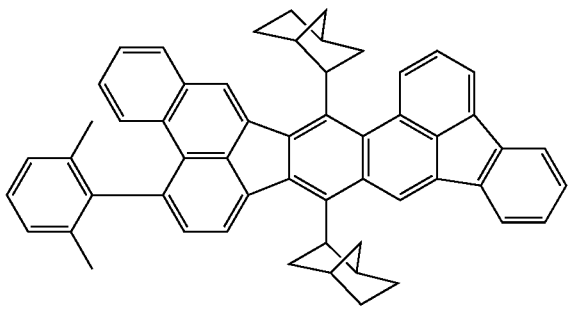
B13
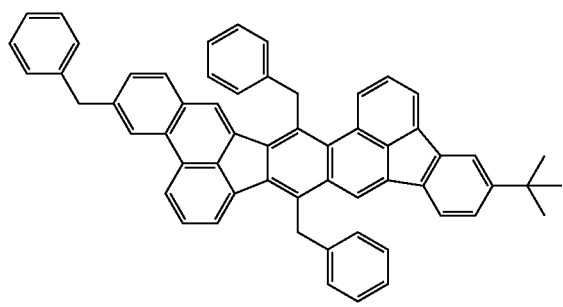
B14
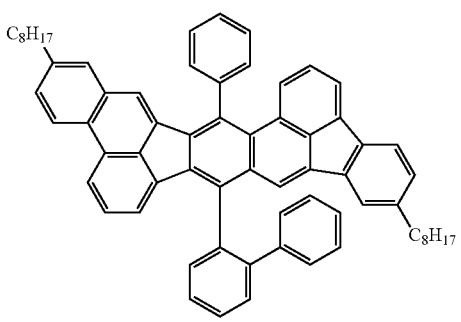
B15
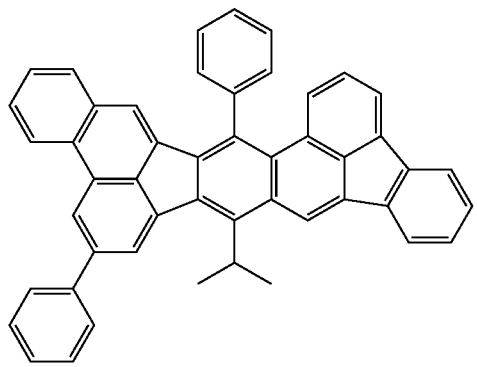
B16
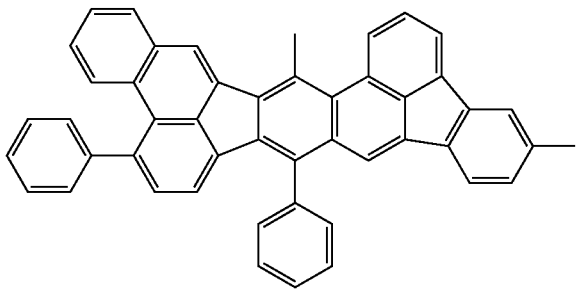
B17
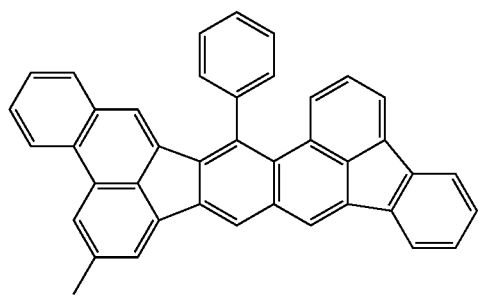
B18
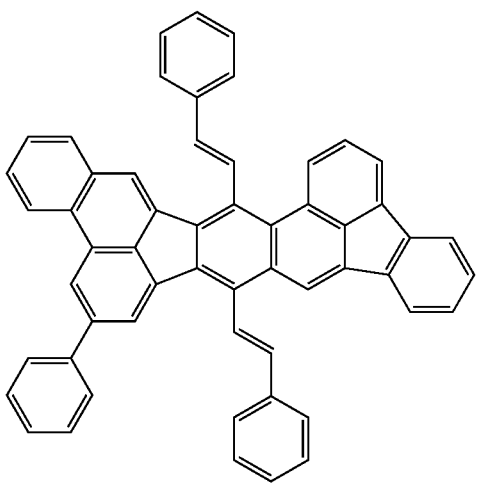

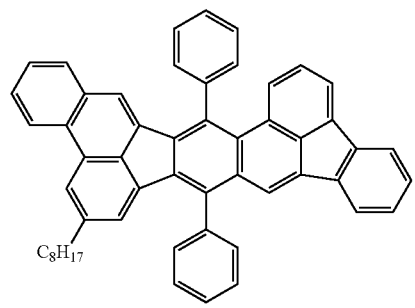
B19
[Chem. 18]
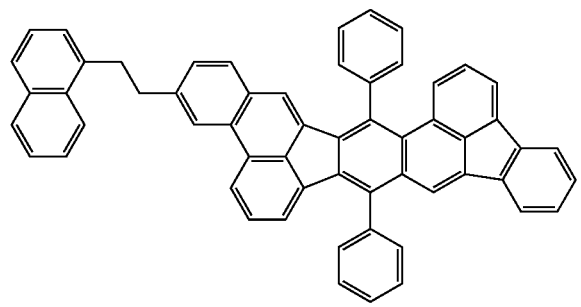
B20
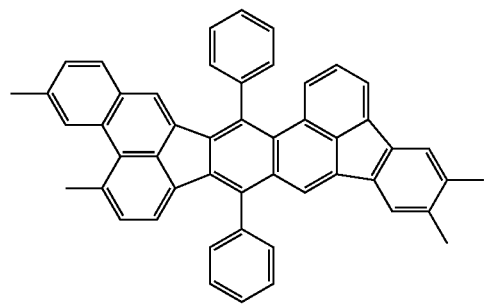
B21
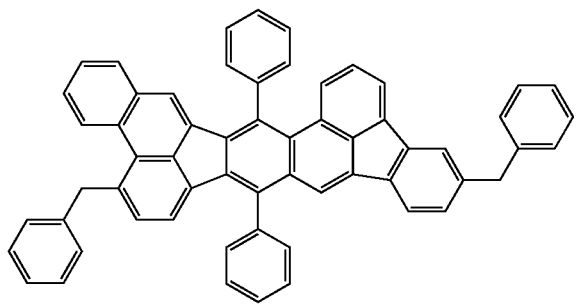
B22
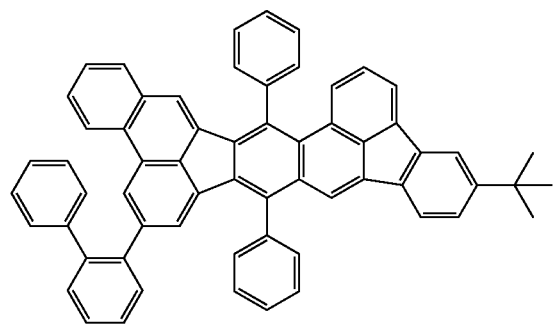
B23
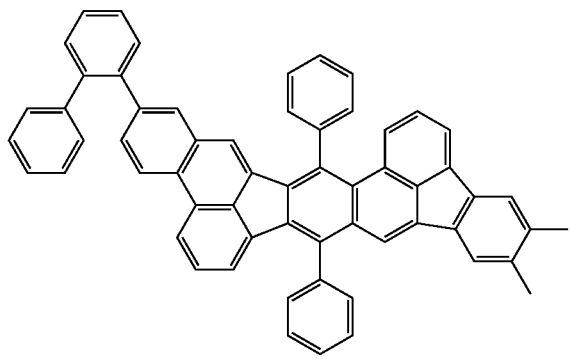
B24

-continued
B25
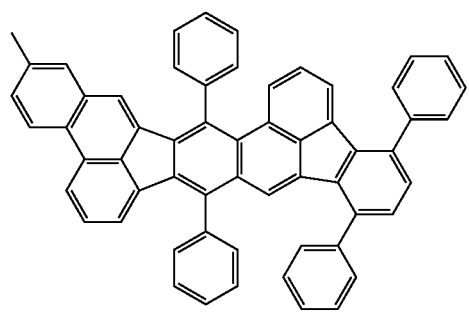
B26
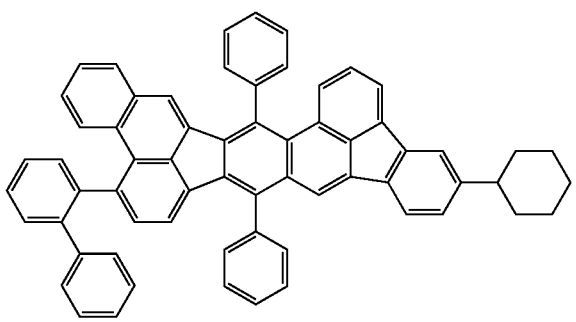
B27
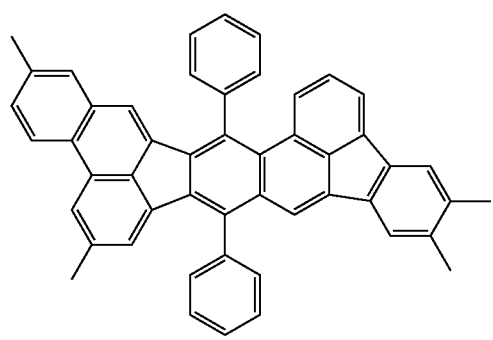
B28
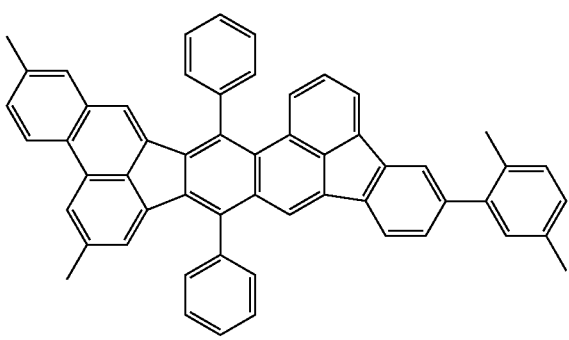
B29
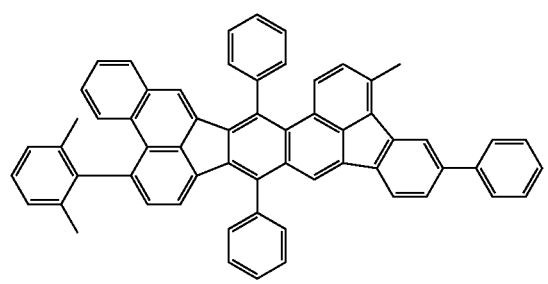
B30
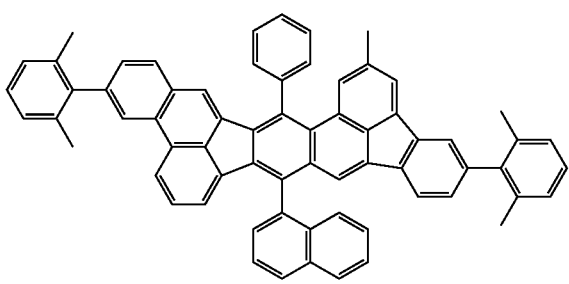
B31
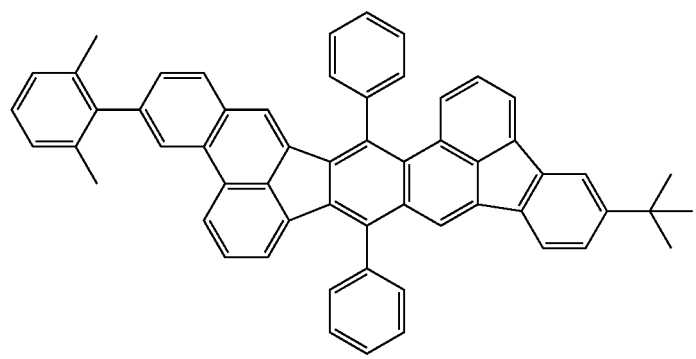

-continued
B32
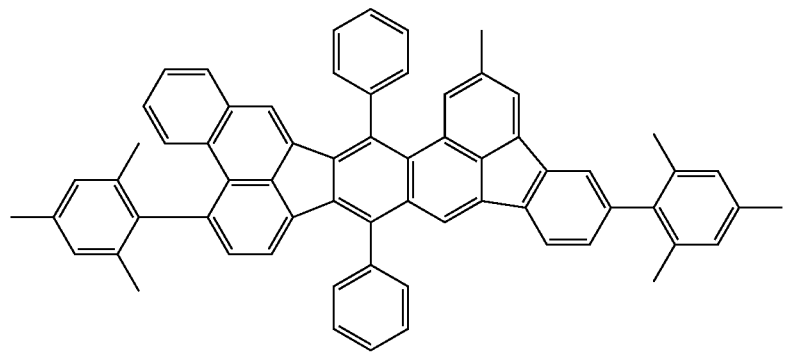
B33
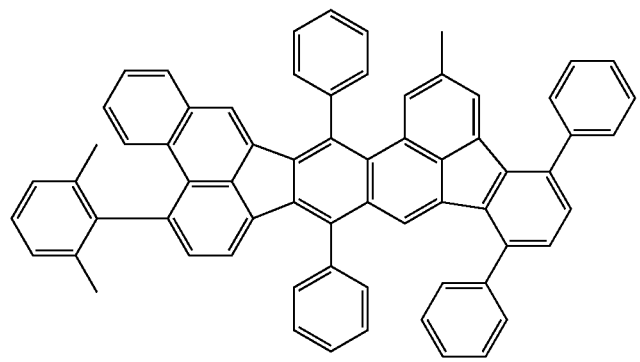
B34
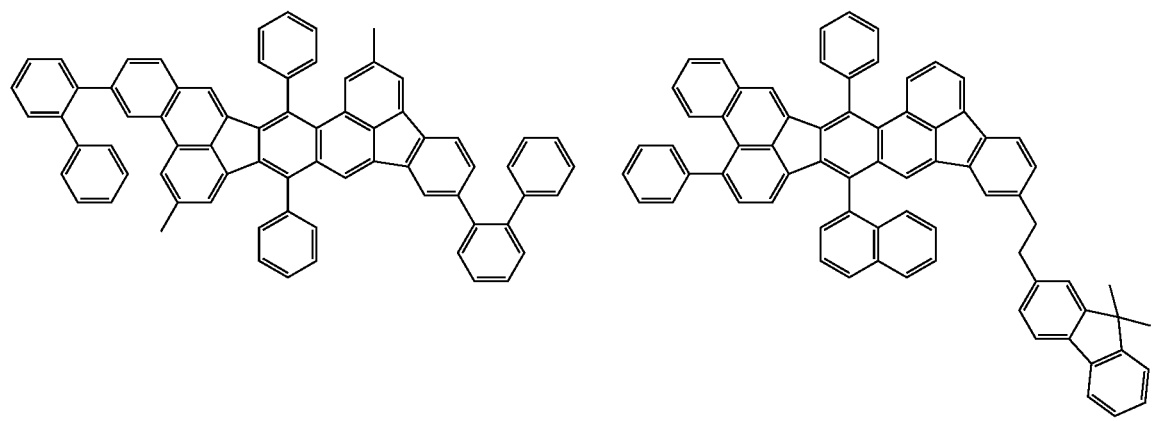
B35
B36
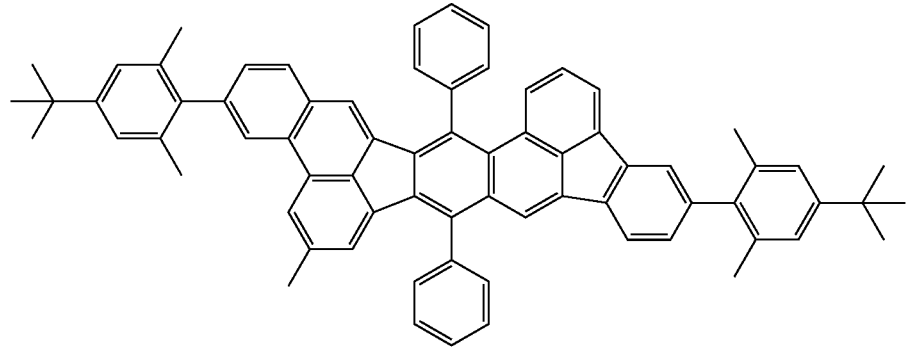

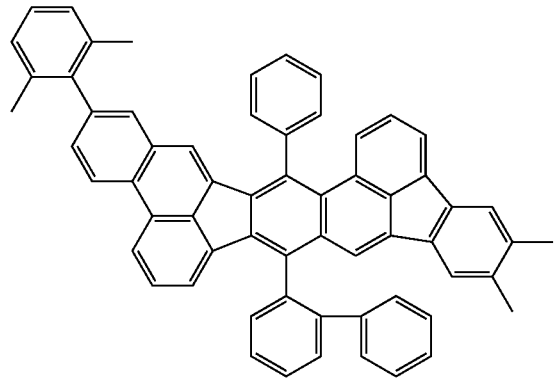
B37
[Chem. 19]
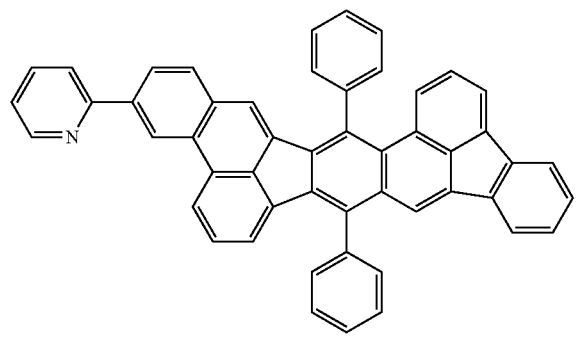
C1
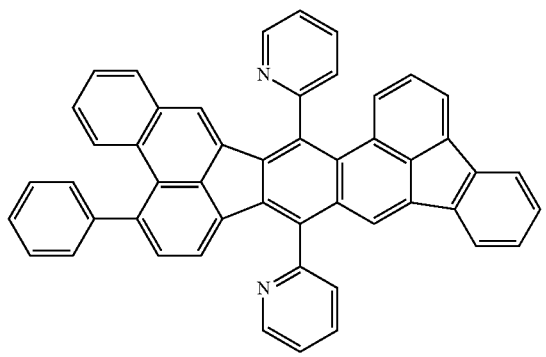
C2
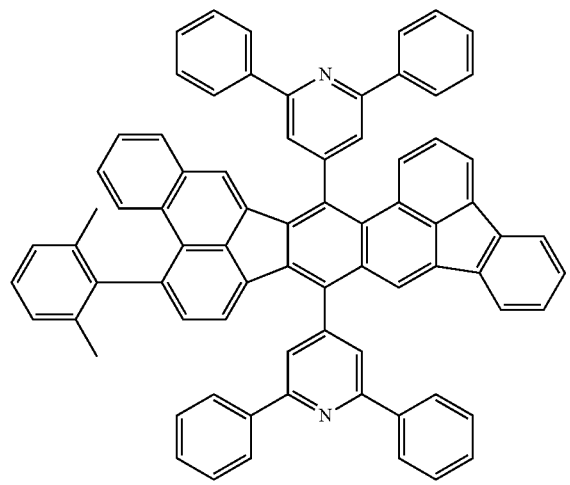
C3

-continued
C4
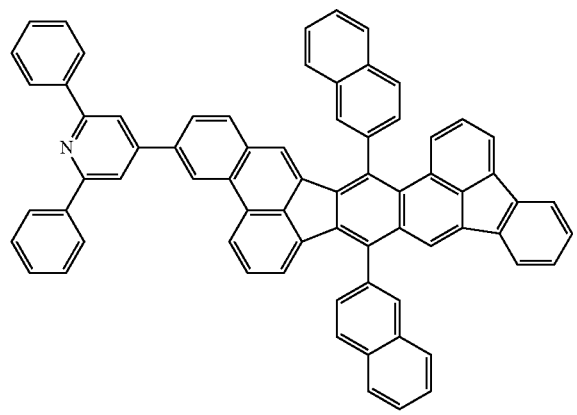
C5
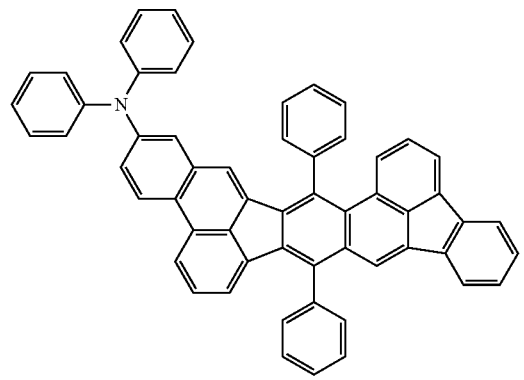
C6
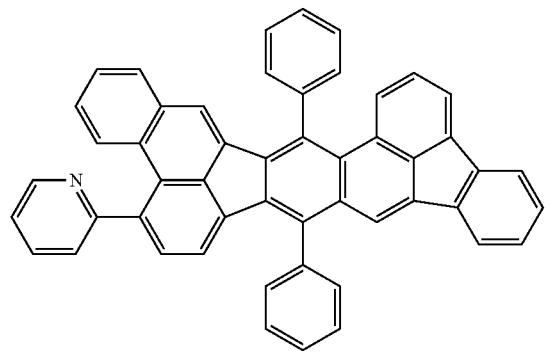
C7
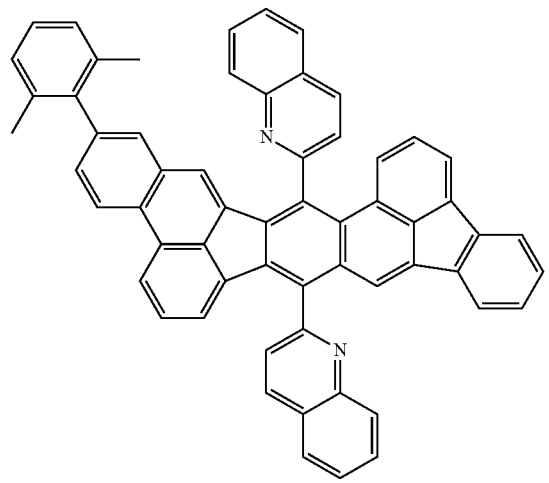
C8
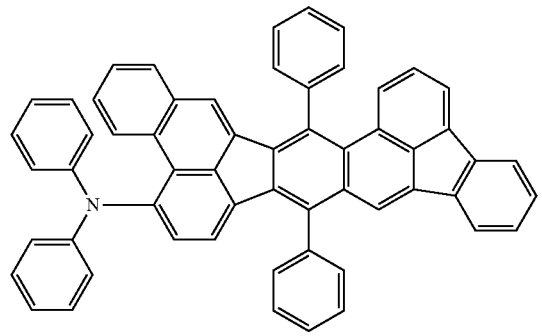
C9
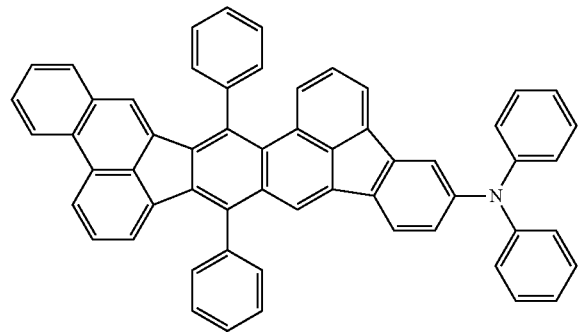

-continued
C10
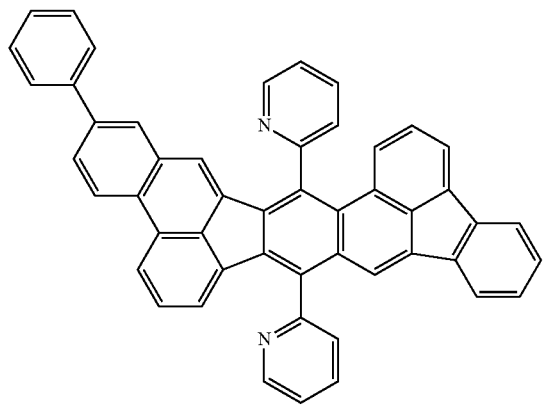
C11
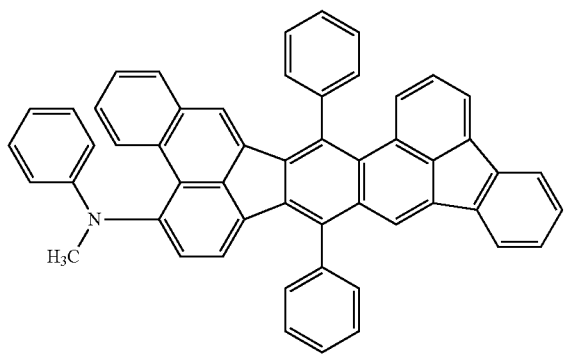
C12
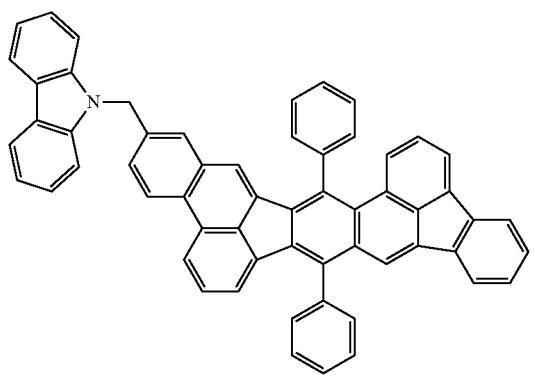
C13
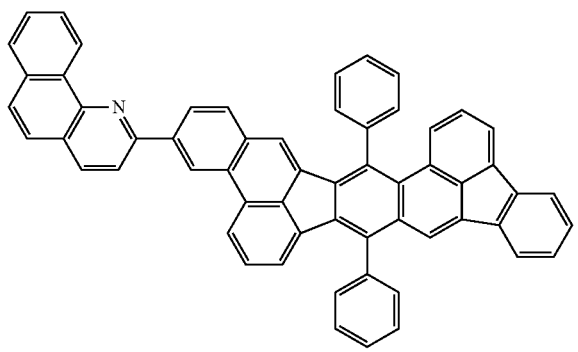
C14
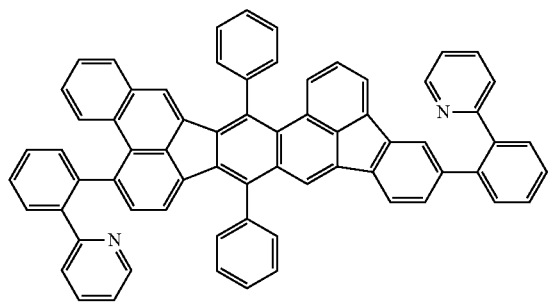
C15
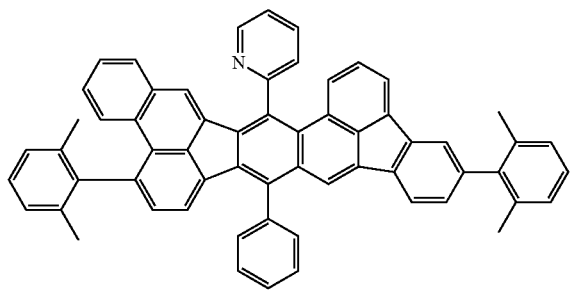
[Chem. 20]
C16
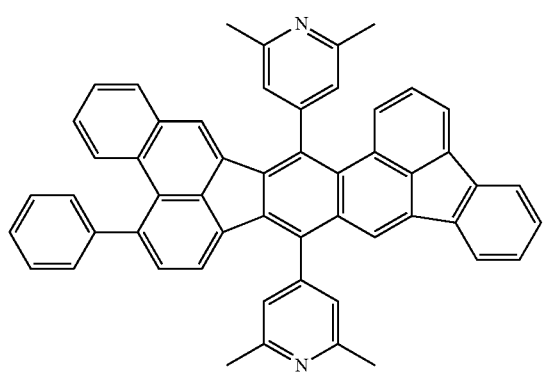
C17
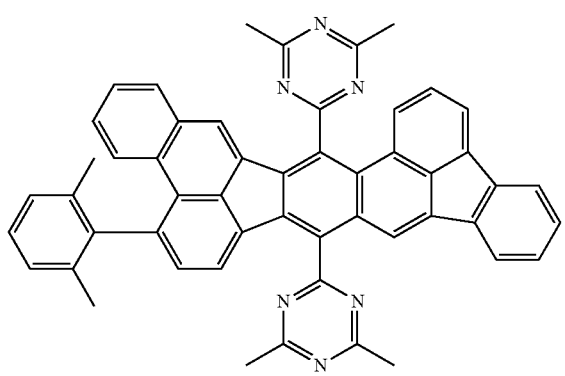

-continued
C18
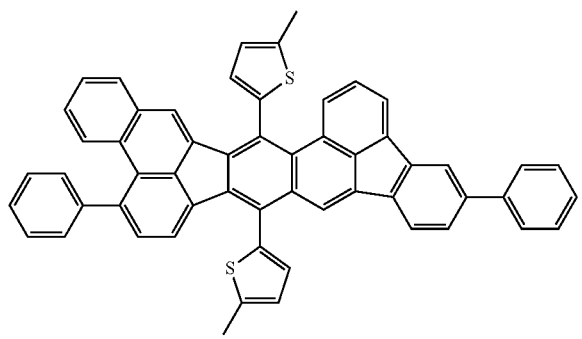
C19
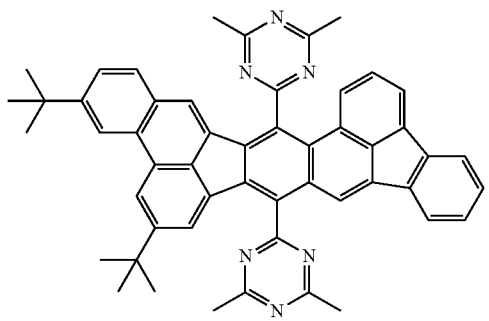
C20
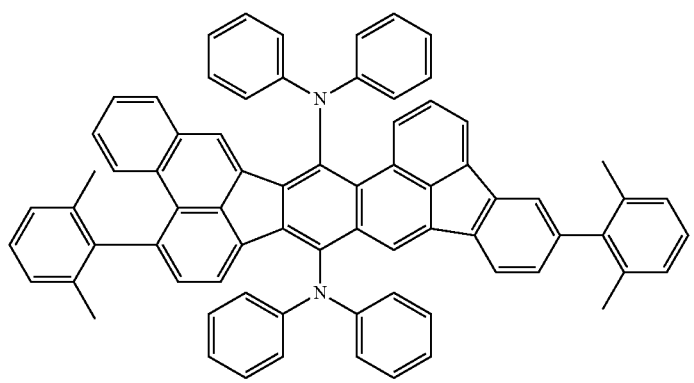
C21
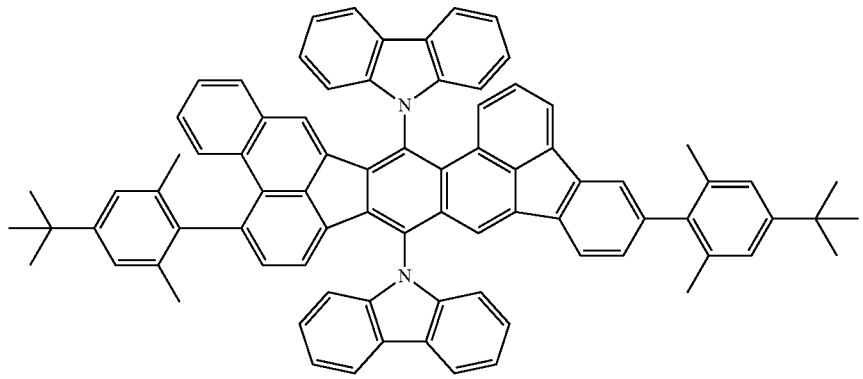
C22
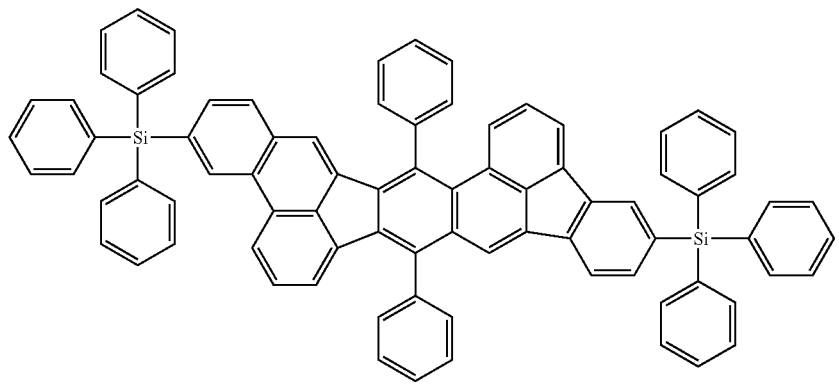

-continued
C23
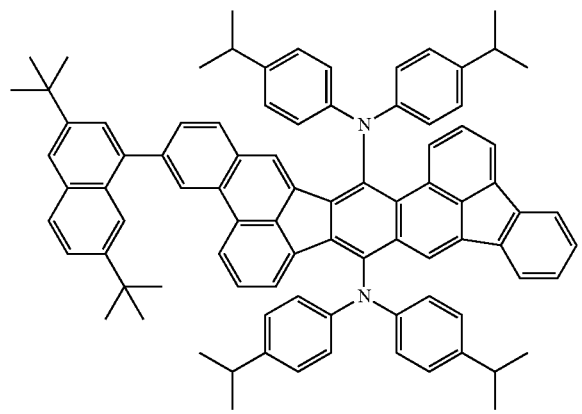
C24
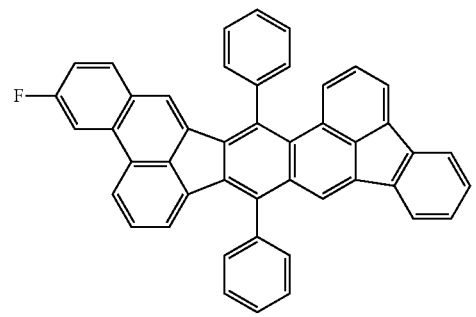
C25
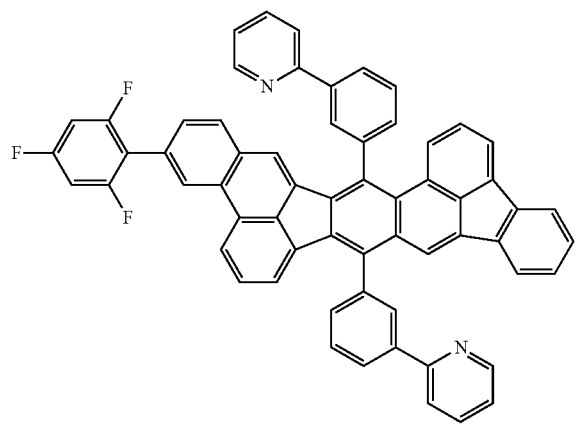
C26
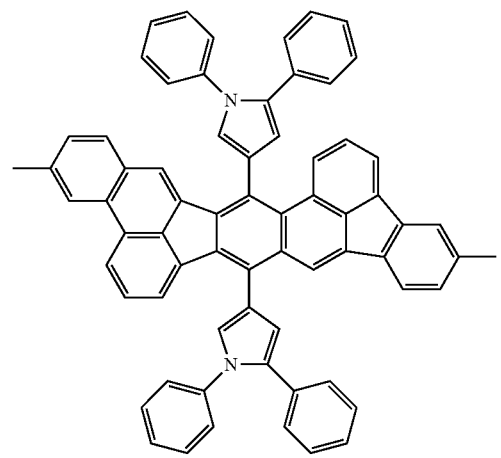
C27
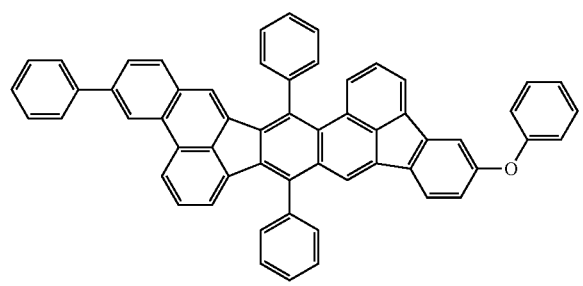
C28
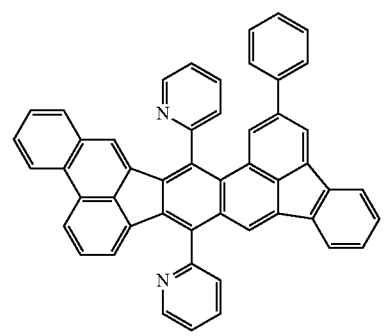
C29
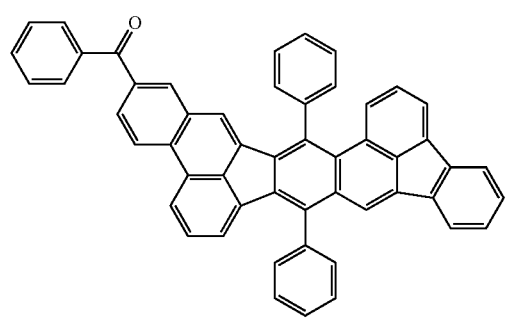
C30
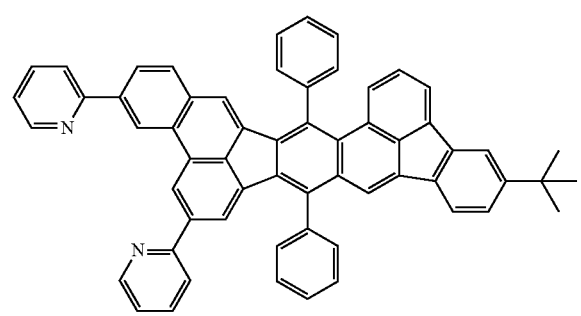

-continued

C31

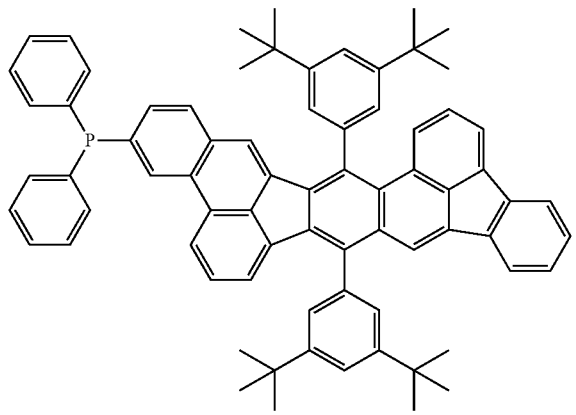

C32

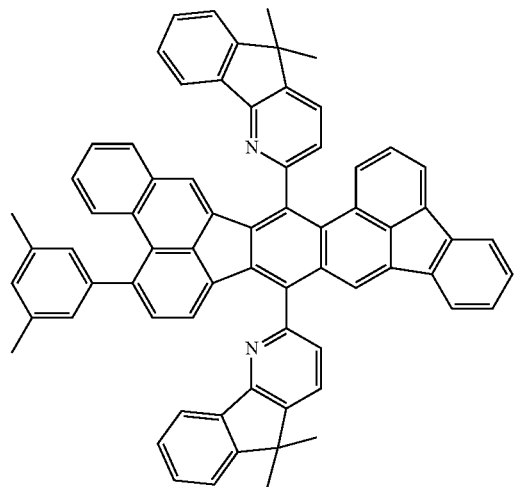

C33

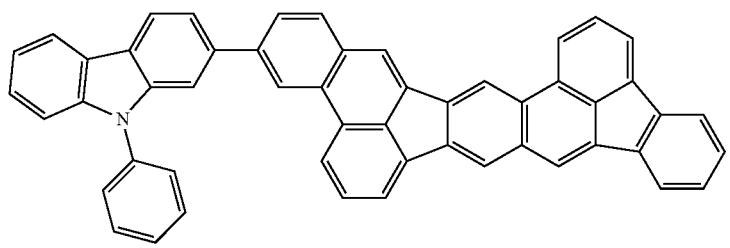

The compounds A1 to A146 are organic compounds having aryl groups on the basic skeleton and the molecule is composed of only a hydrocarbon.

By introducing an aryl group at the 9- or 18-position, concentration quenching can be suppressed. This is because since the aryl group at the 9- or 18-position is substantially perpendicular to the basic skeleton in terms of a dihedral angle, the structure becomes three-dimensional and the intermolecular stacking can be suppressed.

The peak emission wavelength of a compound having an aryl group at a substitution position other than the 9- and 18-positions is shifted to longer wavelengths compared with the peak emission wavelength of the basic skeleton.

By introducing an aryl group at that position, the conjugation of the basic skeleton is extended, which narrows the band gap of the molecule. Thus, such a compound can emit light with a wavelength longer than the emission wavelength of the basic skeleton itself, which is a non-substituted compound.

All the organic compounds in the group A are composed of a hydrocarbon. Therefore, when the half of the total of the oxidation potential and the reduction potential of the basic skeleton is assumed to be a center position, the potential width of oxidation-reduction of these organic compounds can be changed while maintaining the center position.

The compounds B1 to B37 are organic compounds in which an alkyl group is directly bonded to the basic skeleton.

When an alkyl group is directly bonded to the basic skeleton, the organic compound according to the present invention is influenced by the alkyl group having an electron-donating property and thus the oxidation potential is increased. That is, the example compounds in the group B are easily oxidized.

The compounds C1 to C33 are organic compounds including heteroatoms in the molecule thereof.

When the organic compound according to the present invention has a substituent including a heteroatom, the organic compound undergoes the change in the oxidation-reduction potential derived from the heteroatom. This can shift the peak emission wavelength to longer wavelengths.

The organic compound according to the present invention can be used as an electron-trapping luminescent material. Furthermore, when the organic compound has a substituent including a heteroatom, the organic compound can be used in applications such as an electron transport layer material, a hole transport layer material, and a hole-trapping luminescent material, in addition to the electron-trapping luminescent material, because the oxidation-reduction potential varies.

The organic compound according to the present invention is more favorably represented by general formula (2) below. This is because by introducing phenyl groups at the 9- and 18-positions of the basic skeleton of the present invention, the generation of excimers can be highly suppressed. When the phenyl group has a substituent at a position of $R_{19}$ or $R_{20}$, the generation of excimers can be further suppressed.

Moreover, when a substituent is introduced at a position of $R_5$, $R_6$, $R_{14}$, $R_{15}$, or $R_{16}$, the emission wavelength can be changed significantly.

[Chem. 21]

(2)

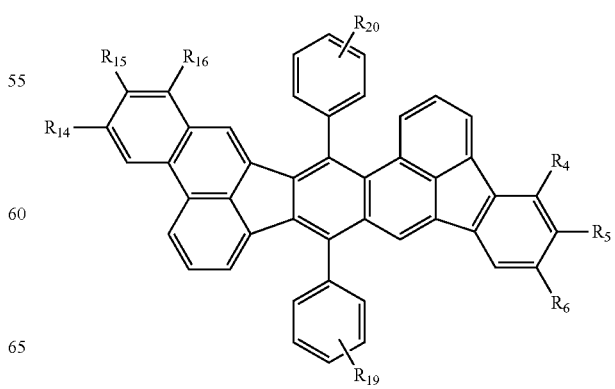

In the general formula (2), substituents represented by $R_5$, $R_6$, $R_{19}$, and $R_{20}$ are each an alkyl group. Substituents represented by $R_{14}$ to $R_{16}$ are each an alkyl group or an aryl group.

The alkyl group is a methyl group, an ethyl group, an n-propyl group, an isopropyl group, an n-butyl group, an isobutyl group, a sec-butyl group, or a tert-butyl group.

The aryl group is a phenyl group, a naphthyl group, a fluorenyl group, a fluoranthenyl group, or a benzofluoranthenyl group. The aryl group may have the above-described alkyl group as a substituent.

The organic compound according to the present invention can be used as a guest material of a light-emitting layer. The organic compound according to the present invention may be a host material or an assist material of a light-emitting layer.

The organic compound according to this embodiment may be used for each layer other than the light-emitting layer, that is, any of a hole injection layer, a hole transport layer, a hole blocking layer, an exciton blocking layer, an electron transport layer, and an electron injection layer.

Herein, a host material is a compound that constitutes the light-emitting layer at the highest weight ratio. A guest material is a compound that constitutes the light-emitting layer at a weight ratio lower than that of the host material, the guest material being a main light-emitting compound in an organic light-emitting device. An assist material is a compound that constitutes the light-emitting layer at a weight ratio lower than that of the host material, the assist material being a compound that assists the light emission of the guest material.

When the organic compound according to the present invention is used as a guest material, the concentration of the guest material relative to the host material is preferably 0.01 wt % or more and 20 wt % or less and more preferably 0.5 wt % or more and 10 wt %.

By changing the concentration of the guest material within one of the two ranges, the emission wavelength of light emitted from the light-emitting layer can be shifted to longer wavelengths by 5 nm or more and 20 nm or less To introduce a substituent into the structure represented by D1, the following synthetic route can be used. .

The organic compound according to the present invention can be synthesized through synthetic route 1 described below. The compounds shown as the example compounds can also be synthesized by substituting hydrogen atoms with other substituents, such as an alkyl group and a phenyl group.

Synthetic route 1

[Chem. 22]

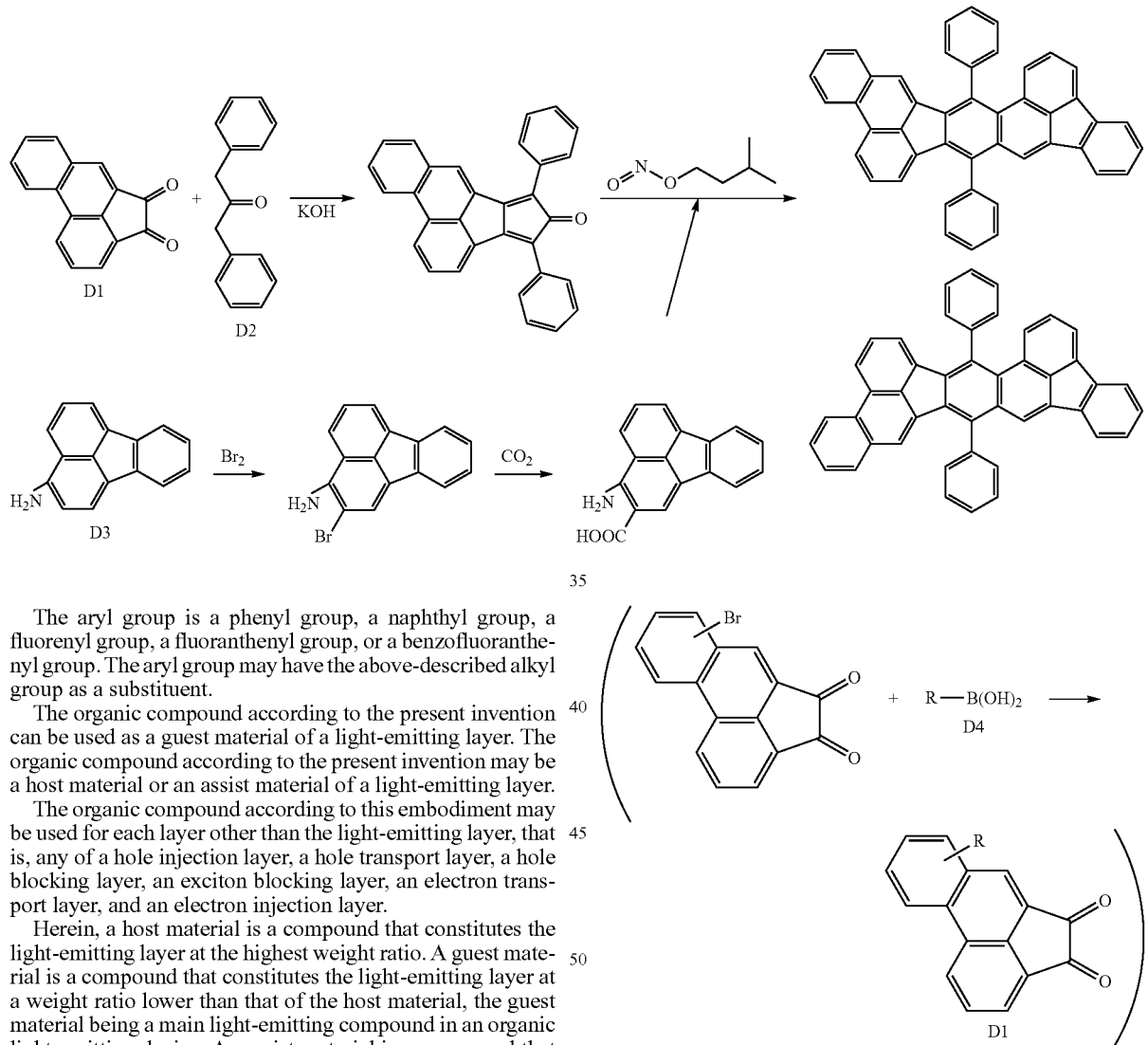

In this synthetic method, an isomer represented by the general formula (3) below is produced in the final synthesis step. Since these isomers have substantially the same light-emitting characteristics, the isomers may be isolated from each other by recrystallization or may be used in a mixed form. When they are used in a mixed form, the degree of crystallinity is lowered and thus an effect of suppressing concentration quenching can be expected. That is, they can be used at high concentration The compound represented by the general formula (1) have an isomer. The isomer is the compound represented by the-general formula (3). Note that an isomer of an example compound A1 is expressed as "A1-2". .

[Chem. 24]

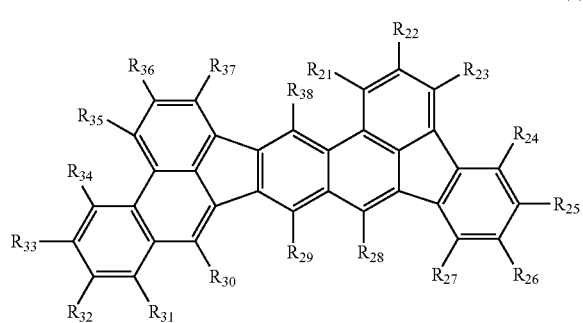

(3)

In the general formula (3), $R_{21}$ to $R_{38}$ are each independently selected from a hydrogen atom, a halogen atom, an alkyl group, an alkoxy group, an amino group, an aryl group, and a heterocyclic group.

Various organic compounds according to the present invention can be synthesized by using starting materials D1 to D4. Tables 2 to 5 show the starting materials D1 to D4 and various organic compounds according to the present invention that are synthesized using the starting materials. The isomers are omitted.

TABLE 2

| | D1 | D2 | D3 |
|---|---|---|---|
| Synthetic Example 1 | | | |
| Synthetic Example 2 | | | |
| Synthetic Example 3 | | | |

TABLE 2-continued
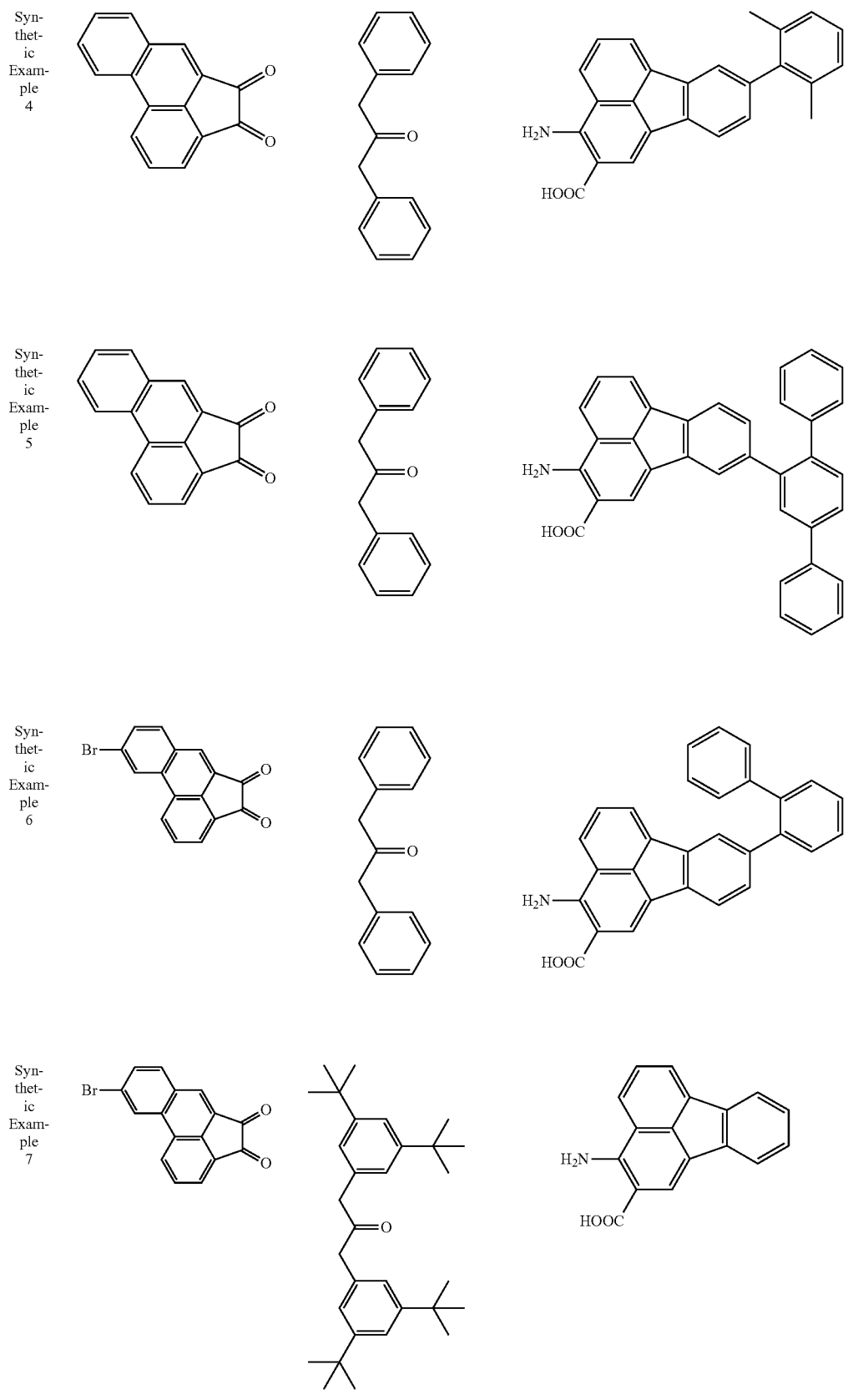

TABLE 2-continued

| | D4 | Synthetic Compound |
|---|---|---|
| Synthetic Example 1 | Ph-B(OH)₂ | A1 |
| Synthetic Example 2 | Ph-B(OH)₂ | A8 |
| Synthetic Example 3 | (2,6-dimethylphenyl)-B(OH)₂ | A20 |
| Synthetic Example 4 | — | A22 |

TABLE 2-continued
| Synthetic Example 5 | 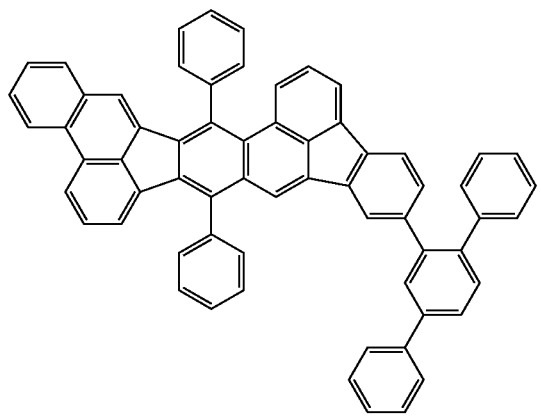 A43 |
| Synthetic Example 6 | 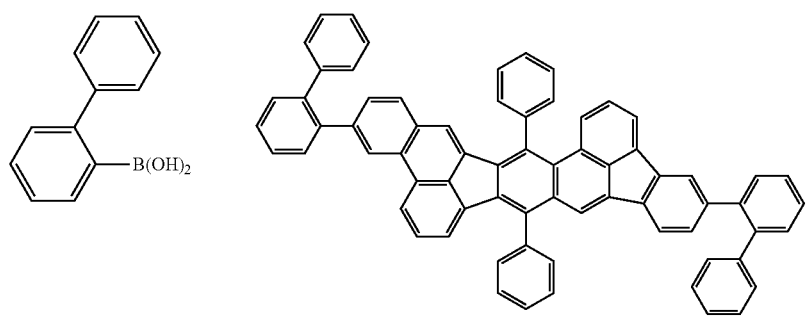 A51 |
| Synthetic Example 7 | 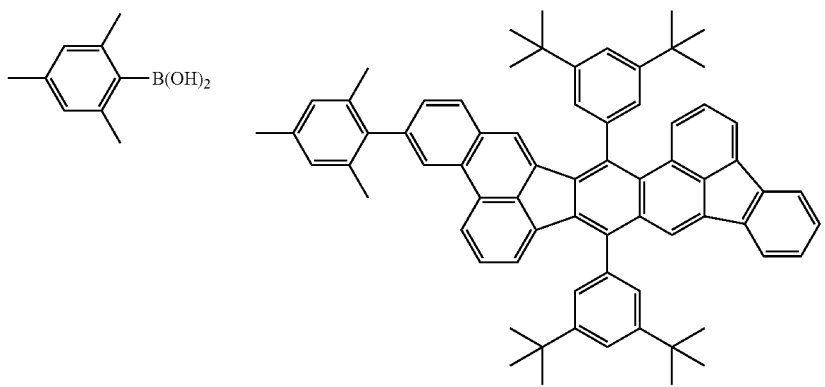 A54 |

TABLE 3
| | | |
|---|---|---|
| 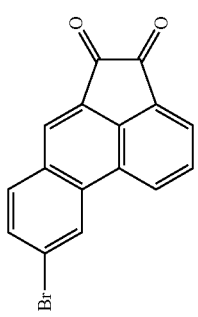 | 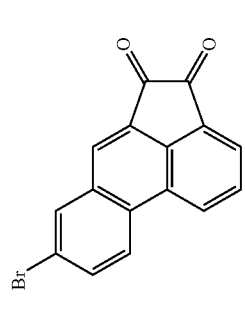 | 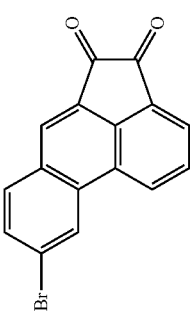 |
| 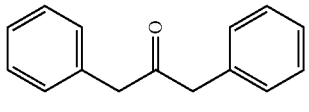 | 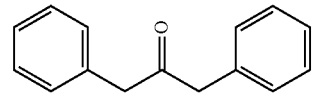 | 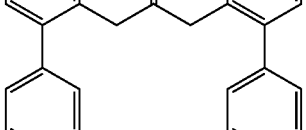 |
| 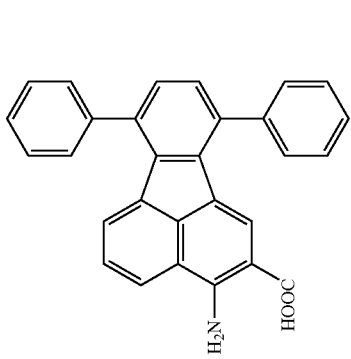 | 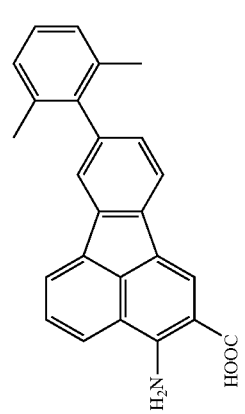 | 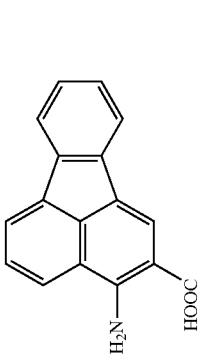 |
| Synthetic Example 8 | Synthetic Example 9 | Synthetic Example 10 |

TABLE 3-continued
| | | |
|---|---|---|
| Synthetic Example 11 | 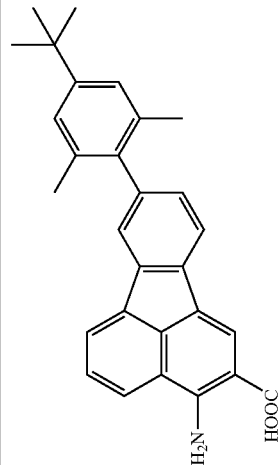 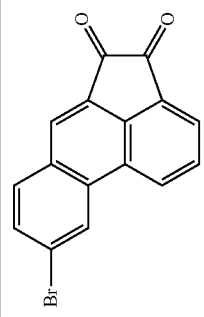 | |
| Synthetic Example 12 | 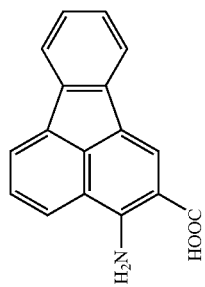 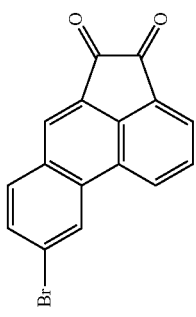 | |
| Synthetic Example 13 | 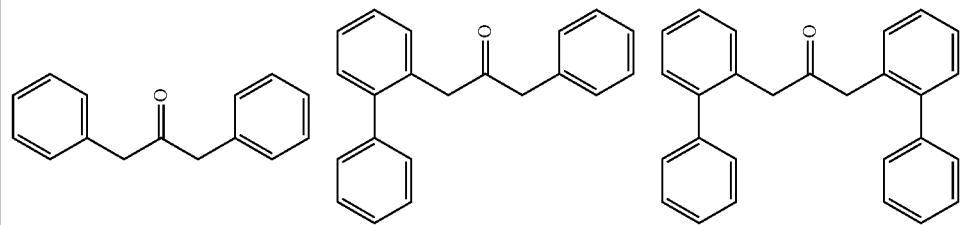 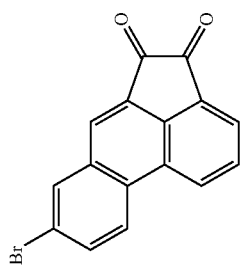 | |

TABLE 3-continued
| Synthetic Example 14 | 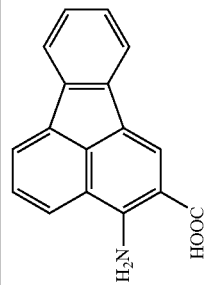 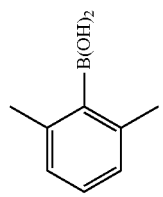 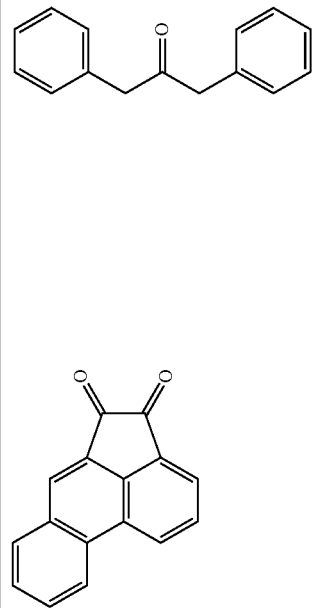 | 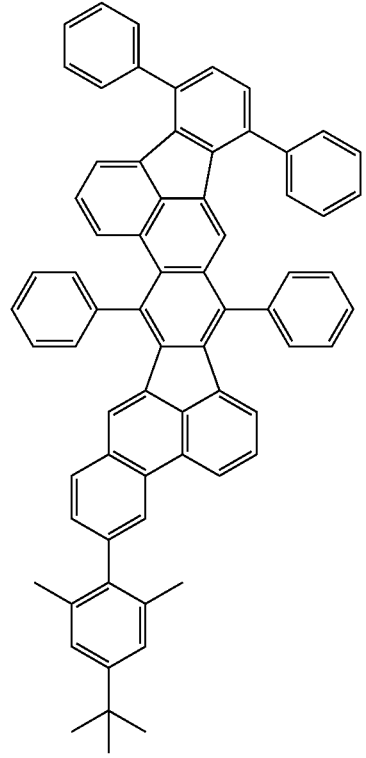 A55 |
| --- | --- | --- |
| Synthetic Example 8 | | |

TABLE 3-continued
| Synthetic Example 9 | 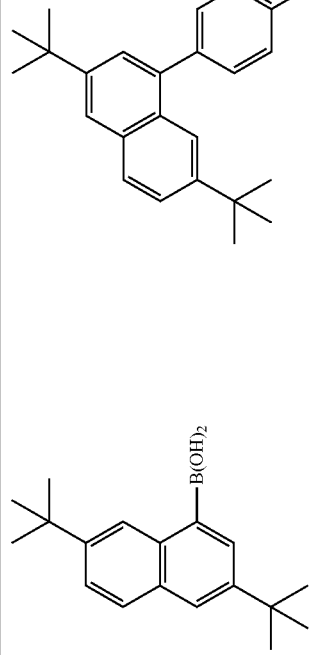 | 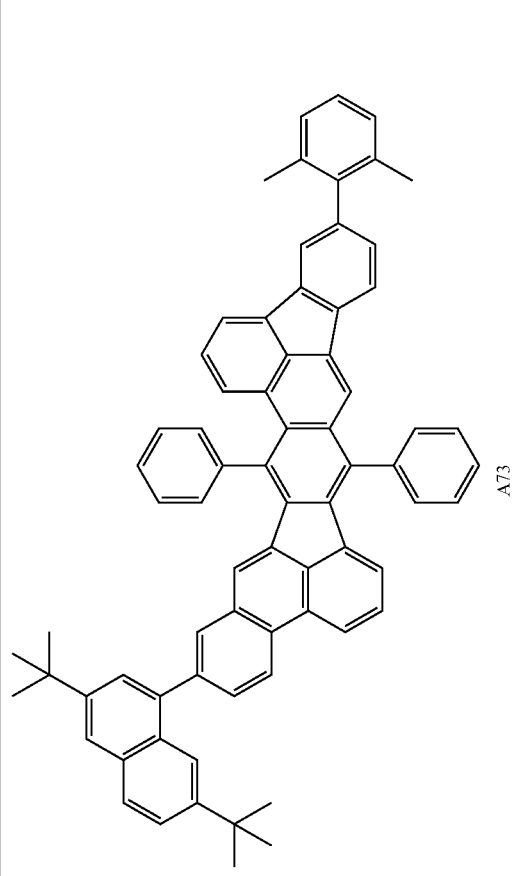 A73 |
| Synthetic Example 10 | 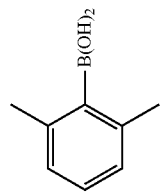 | 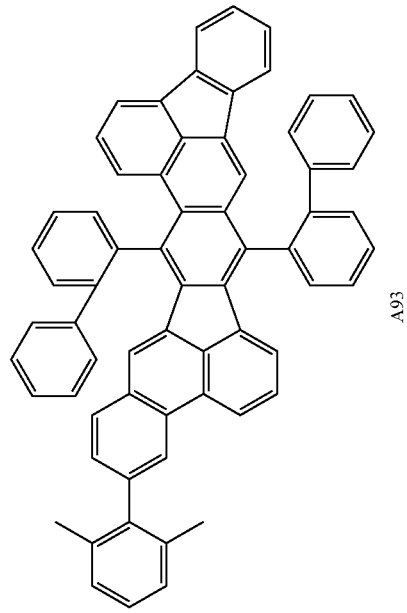 A93 |

TABLE 3-continued
| Synthetic Example 11 | 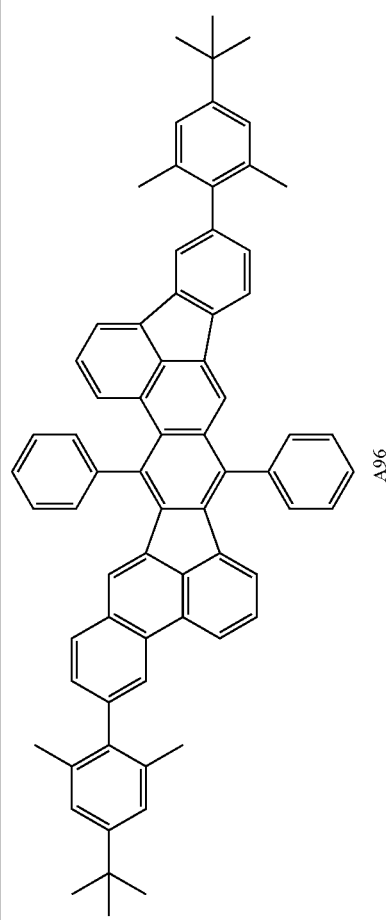 A96 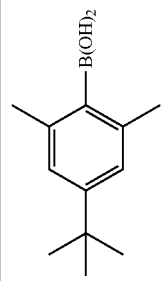 |

TABLE 3-continued
| Synthetic Example 12 | 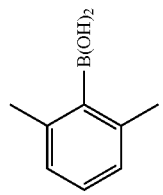 | A99 | A99-3 |

TABLE 3-continued
| Synthetic Example 13 | 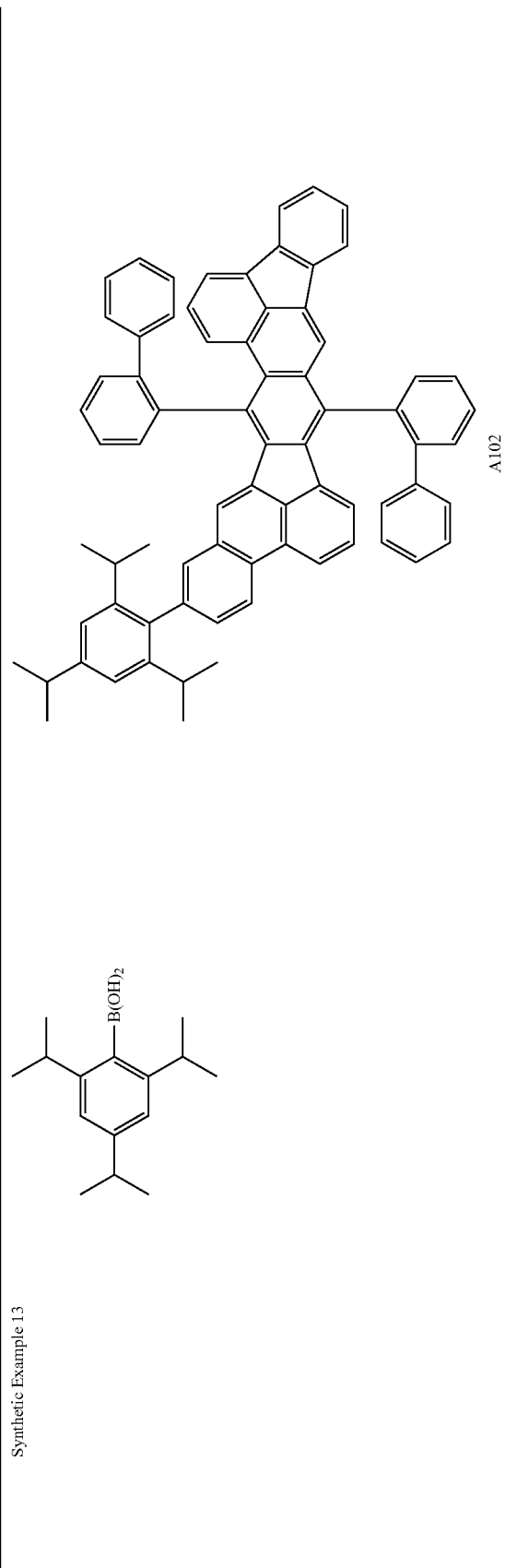 | A102 |
| Synthetic Example 14 | — | 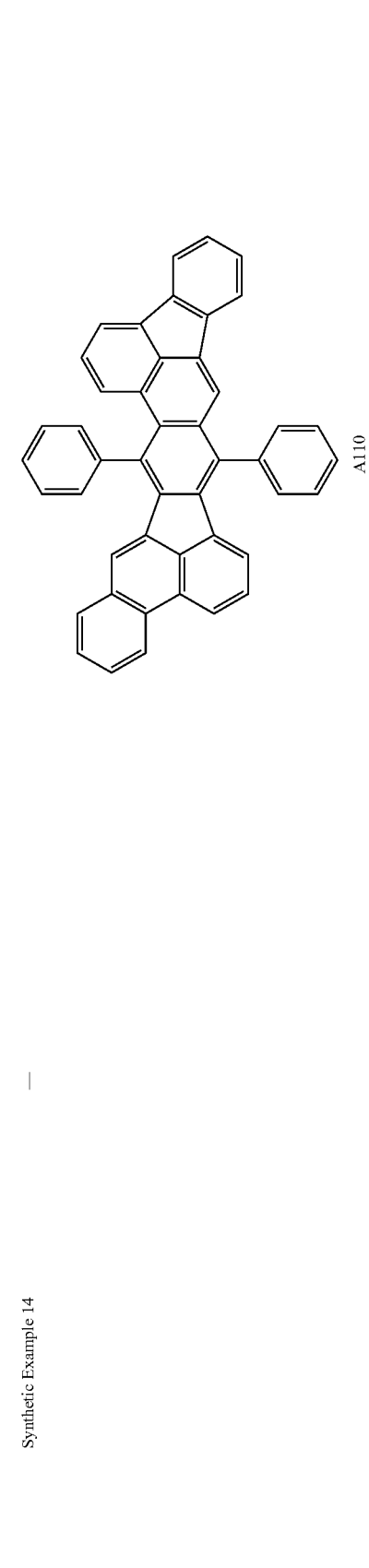 A110 |

TABLE 4
| Synthetic Example 15 | 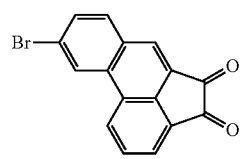 [SMILES: O=C1C(=O)c2cc3ccc(Br)cc3c3cccc1c23] | 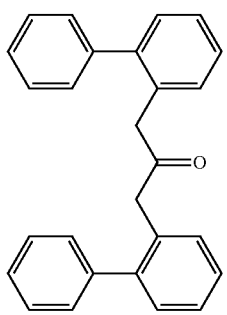 | 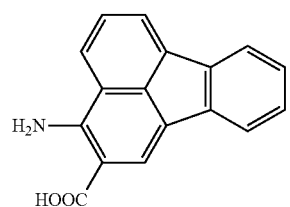 [SMILES: Nc1c(C(=O)O)cc2c3c(cccc13)-c1ccccc1-2] |
| Synthetic Example 16 | 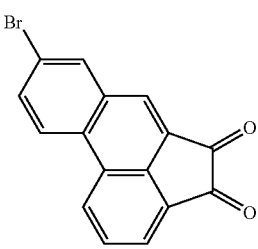 [SMILES: O=C1C(=O)c2cc3cc(Br)ccc3c3cccc1c23] | 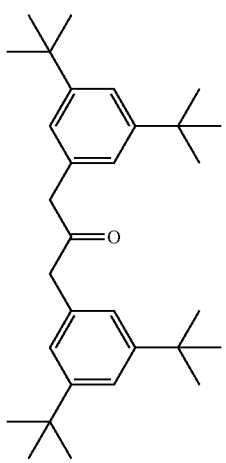 | 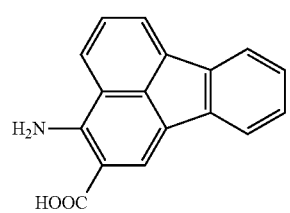 [SMILES: Nc1c(C(=O)O)cc2c3c(cccc13)-c1ccccc1-2] |
| Synthetic Example 17 | 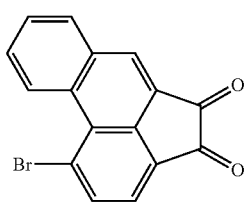 [SMILES: O=C1C(=O)c2cc3ccccc3c3c(Br)ccc1c23] | 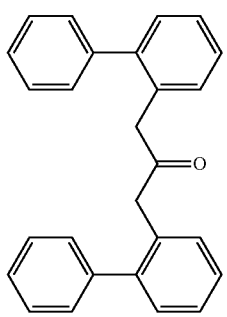 | 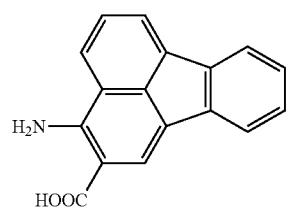 [SMILES: Nc1c(C(=O)O)cc2c3c(cccc13)-c1ccccc1-2] |
| Synthetic Example 18 | 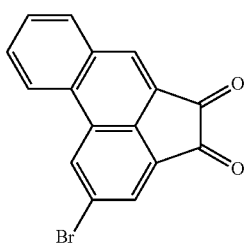 [SMILES: O=C1C(=O)c2cc3ccccc3c3cc(Br)cc1c23] | 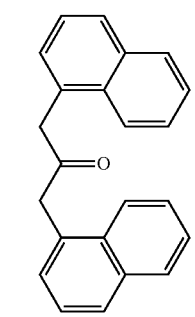 | 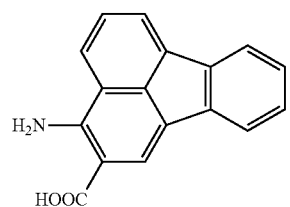 [SMILES: Nc1c(C(=O)O)cc2c3c(cccc13)-c1ccccc1-2] |

TABLE 4-continued
| | 101 | | 102 |
|---|---|---|---|
| Synthetic Example 19 | 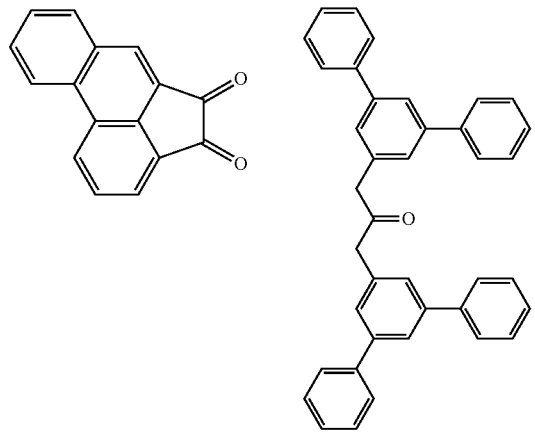 | | 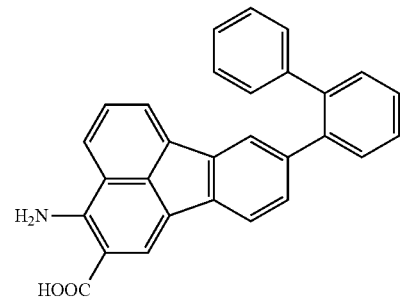 [SMILES: Nc1c(C(=O)O)cc2c3c(cccc13)-c1cc(-c3ccccc3-c3ccccc3)ccc1-2] |
| Synthetic Example 20 | 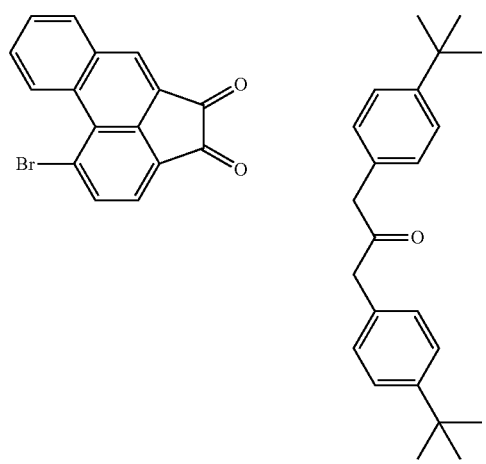 | | 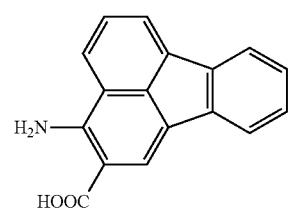 [SMILES: Nc1c(C(=O)O)cc2c3c(cccc13)-c1ccccc1-2] |
| Synthetic Example 21 | 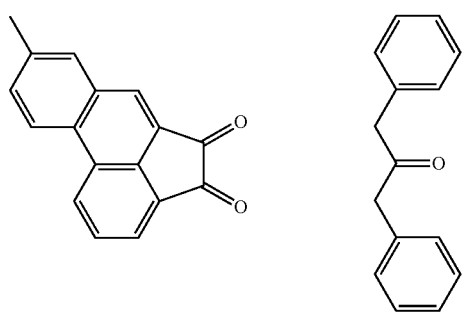 | | 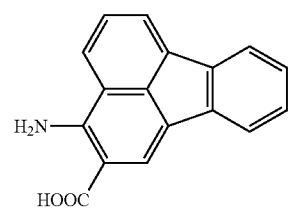 [SMILES: Nc1c(C(=O)O)cc2c3c(cccc13)-c1ccccc1-2] |
| Synthetic Example 22 | 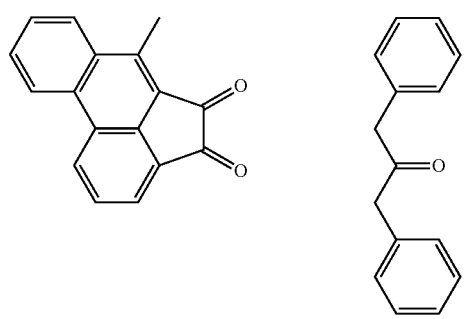 | | 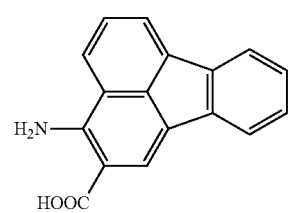 [SMILES: Nc1c(C(=O)O)cc2c3c(cccc13)-c1ccccc1-2] |

TABLE 4-continued
Synthetic Example 15
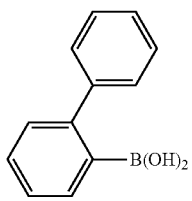 [SMILES: OB(O)c1ccccc1-c1ccccc1]
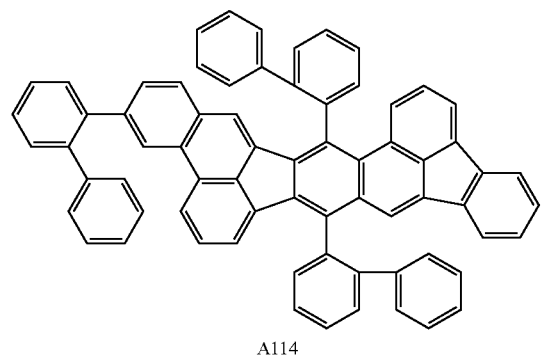
A114
Synthetic Example 16
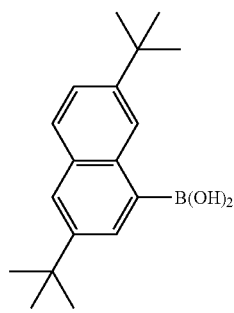 [SMILES: CC(C)(C)c1cc(B(O)O)c2cc(C(C)(C)C)ccc2c1]
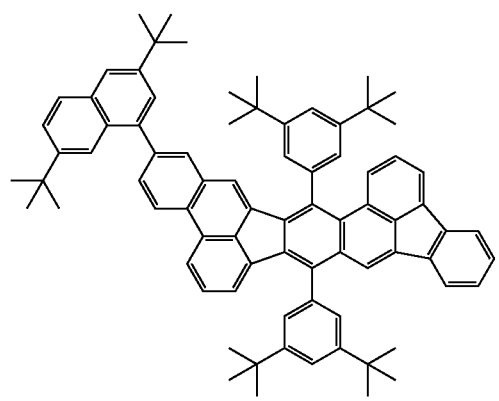
A116
Synthetic Example 17
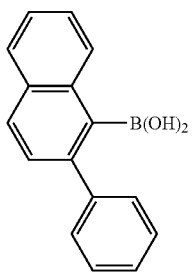 [SMILES: OB(O)c1c(-c2ccccc2)ccc2ccccc12]
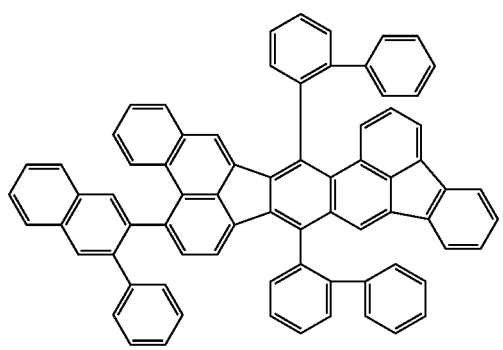
A120
Synthetic Example 18
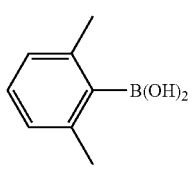
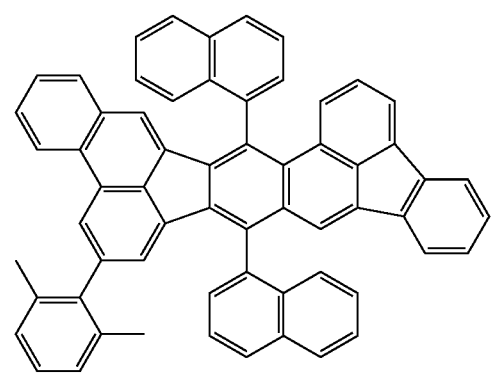
A124

TABLE 4-continued
| | | |
|---|---|---|
| Synthetic Example 19 | — | 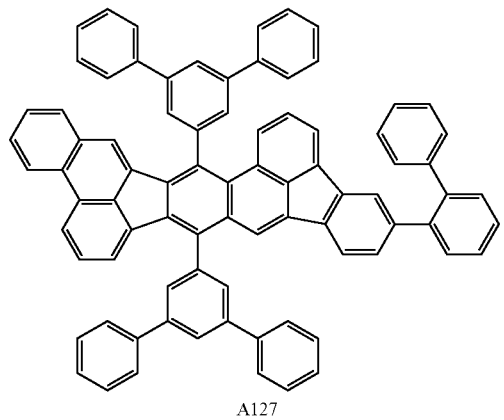 A127 |
| Synthetic Example 20 | 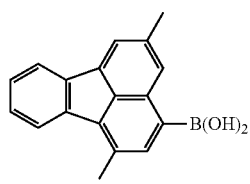 [SMILES: Cc1cc2c3c(c(C)cc(B(O)O)c3c1)-c1ccccc1-2] | 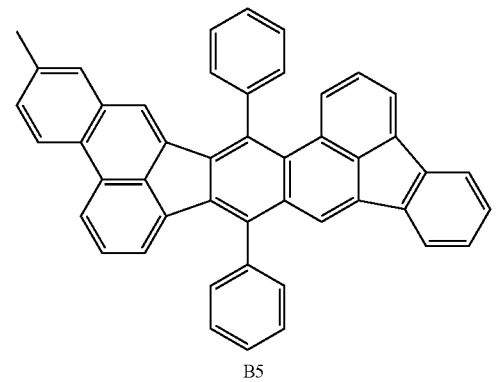 A144 |
| Synthetic Example 21 | — | B5 |
| Synthetic Example 22 | — | 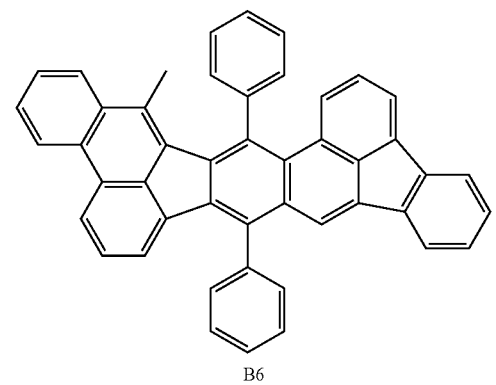 B6 |

TABLE 5
| Synthetic Example 23 | 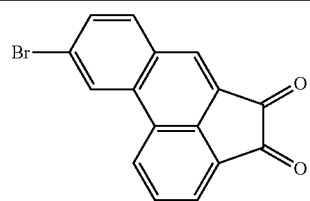 | 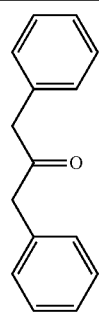 | 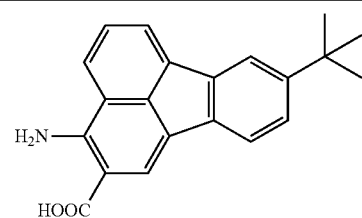 |
| --- | --- | --- | --- |
| Synthetic Example 24 | 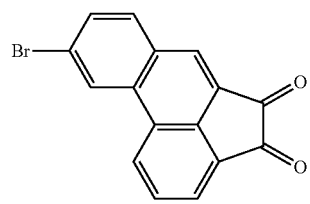 | 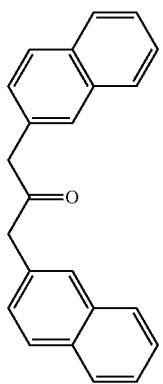 [SMILES: O=C(Cc1ccc2ccccc2c1)Cc1ccc2ccccc2c1] | 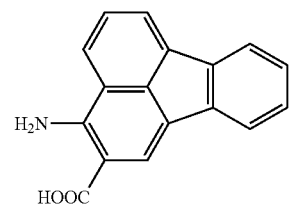 [SMILES: Nc1c(C(=O)O)cc2c3c(cccc13)-c1ccccc1-2] |
| Synthetic Example 25 | 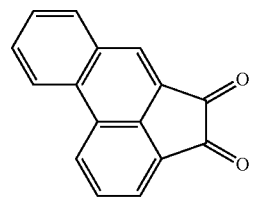 [SMILES: O=C1C(=O)c2cc3ccccc3c3cccc1c23] | 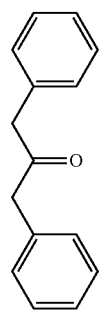 [SMILES: O=C(Cc1ccccc1)Cc1ccccc1] | 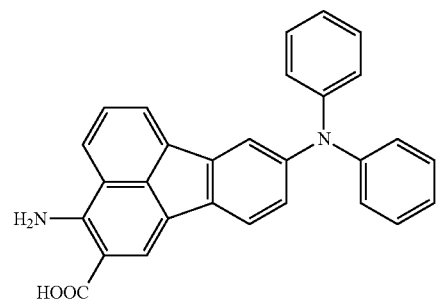 [SMILES: Nc1c(C(=O)O)cc2c3c(cccc13)-c1cc(N(c3ccccc3)c3ccccc3)ccc1-2] |
| Synthetic Example 23 | | 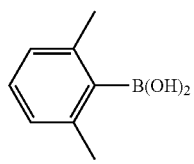 | 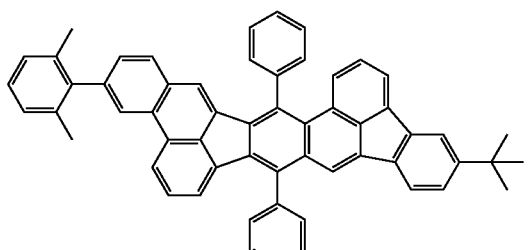 B31 |

TABLE 5-continued

| Synthetic Example 24 | 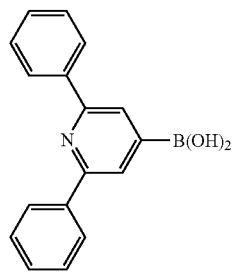 [SMILES: OB(O)c1cc(-c2ccccc2)nc(-c2ccccc2)c1] | 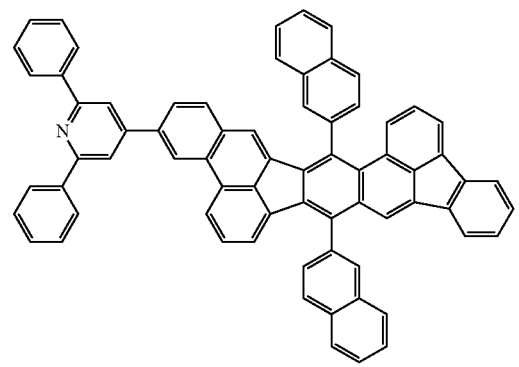 |
|---|---|---|
| | | C4 |
| Synthetic Example 25 | — | 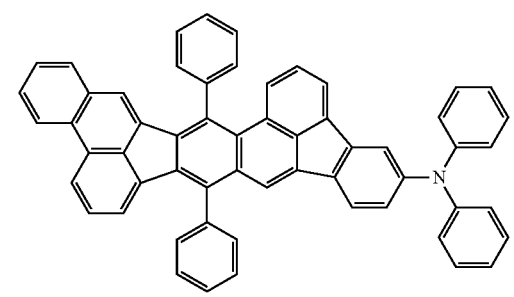 |
| | | C9 |

An example of an organic light-emitting device including the organic compound according to this embodiment will now be described.

The organic light-emitting device according to this embodiment has a structure in which a light-emitting layer is formed between a positive electrode and a negative electrode, which are an example of a pair of electrodes. In addition, a hole transport layer or a hole injection layer may be formed between the positive electrode and the light-emitting layer. An electron transport layer, an electron injection layer, a hole blocking layer, an exciton blocking layer, or the like may be formed between the light-emitting layer and the negative electrode.

The layer structure of the organic compound layer of the organic light-emitting device according to this embodiment is not limited thereto.

In the organic light-emitting device according to this embodiment, multiple organic compound layers may be formed. Examples of the multiple layers include a hole injection layer, a hole transport layer, a light-emitting layer, a hole blocking layer, an exciton blocking layer, an electron transport layer, and an electron injection layer. These layers can be suitably combined with each other.

In the organic light-emitting device according to this embodiment, in addition to the organic compound according to the present invention, a publicly known low-molecular-weight or high-molecular-weight hole-transporting compound, luminescent compound, or electron-transporting compound can be optionally used together.

Such compounds are exemplified below.

Hole injection/transport materials can have a high hole mobility so that holes can be easily injected from the positive electrode and the injected holes can be transported to the light-emitting layer. Examples of the low-molecular-weight or high-molecular-weight materials having hole injection/transport properties include, but are not limited to, triarylamine derivatives, phenylenediamine derivatives, stilbene derivatives, phthalocyanine derivatives, porphyrin derivatives, polyvinylcarbazole, polythiophene, and other electrically conductive polymers.

Examples of the host material mainly include, but are not limited to, in addition to the compounds shown in Tables 6 and 7 and derivatives of the compounds shown in Tables 6 and 7, fused-ring compounds (such as fluorene derivatives, naphthalene derivatives, anthracene derivatives, pyrene derivatives, carbazole derivatives, quinoxaline derivatives, and quinoline derivatives), organoaluminum complexes such as tris(8-quinolinolato)aluminum, organozinc complexes, triphenylamine derivatives, and polymer derivatives such as polyfluorene derivatives and polyphenylene derivatives.

TABLE 6
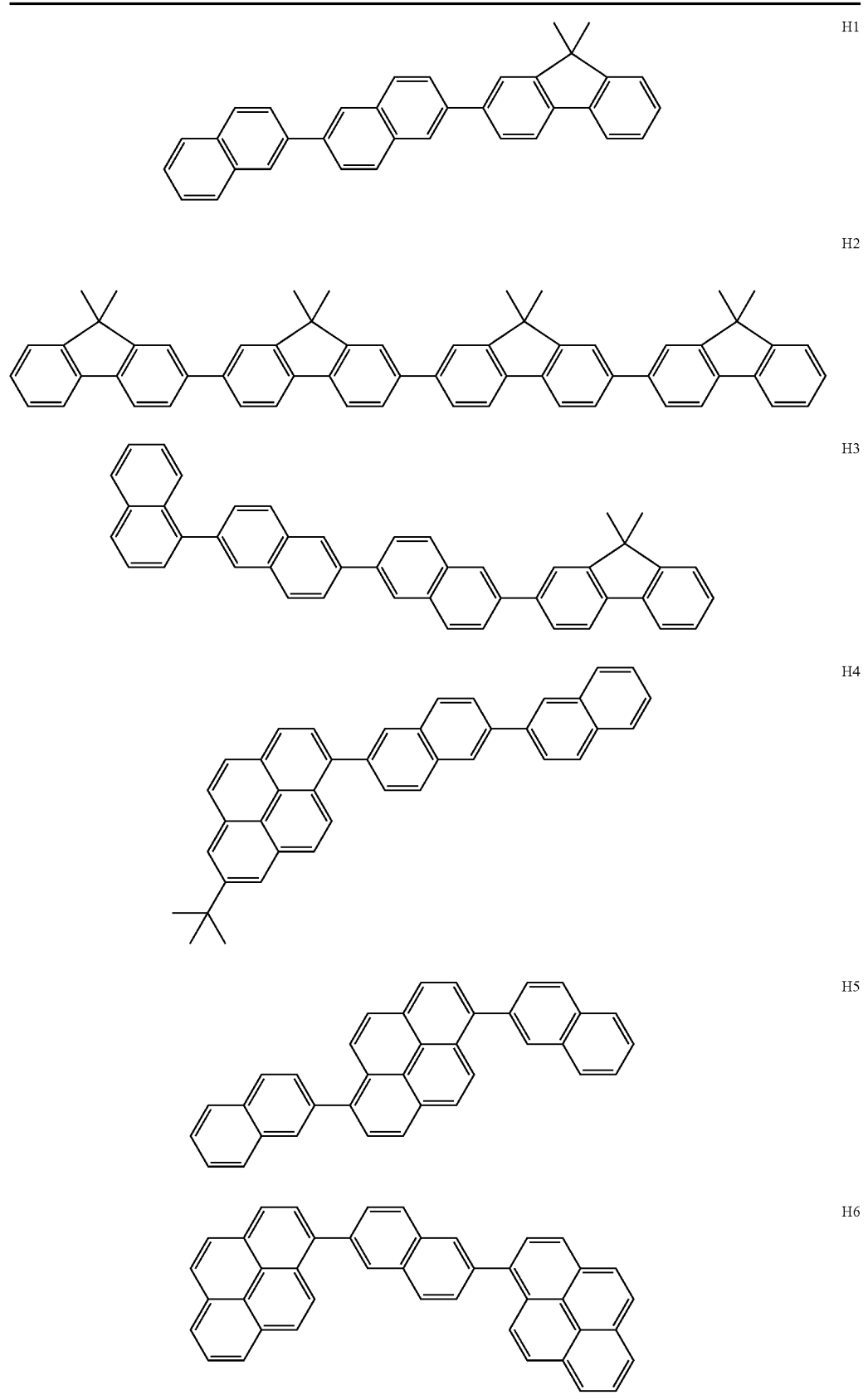

TABLE 6-continued
| | |
|---|---|
| 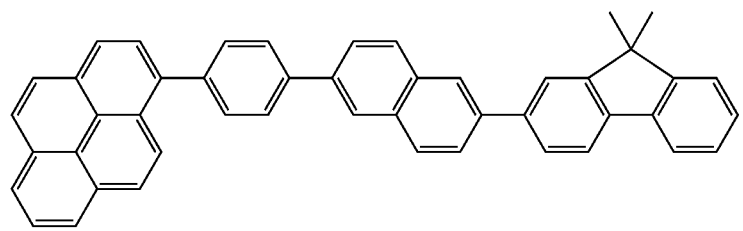 [SMILES: CC1(C)c2ccccc2-c2ccc(-c3ccc4cc(-c5ccc(-c6ccc7ccc8cccc9ccc6c7c89)cc5)ccc4c3)cc21] | H7 |
| 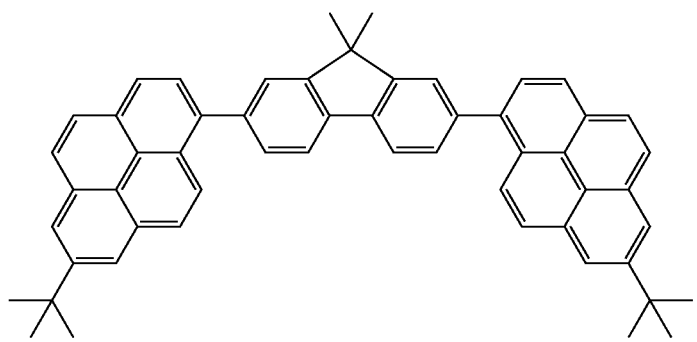 [SMILES: CC(C)(C)c1cc2ccc3ccc(-c4ccc5c(c4)C(C)(C)c4cc(-c6ccc7ccc8cc(C(C)(C)C)cc9ccc6c7c89)ccc4-5)c4ccc(c1)c2c34] | H8 |
| 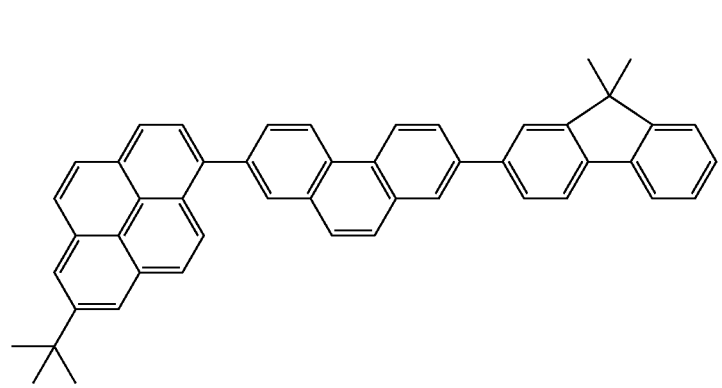 [SMILES: CC(C)(C)c1cc2ccc3ccc(-c4ccc5c(ccc6cc(-c7ccc8c(c7)C(C)(C)c7ccccc7-8)ccc65)c4)c4ccc(c1)c2c34] | H9 |
| 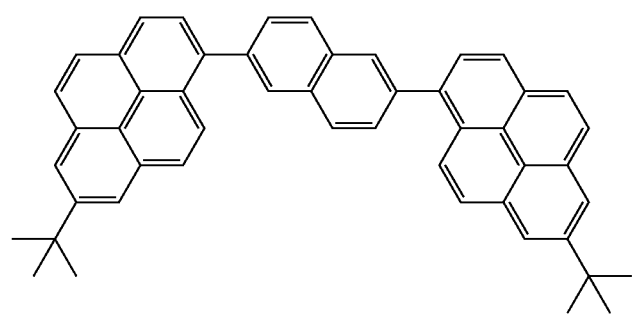 [SMILES: CC(C)(C)c1cc2ccc3ccc(-c4ccc5cc(-c6ccc7ccc8cc(C(C)(C)C)cc9ccc6c7c89)ccc5c4)c4ccc(c1)c2c34] | H10 |
| 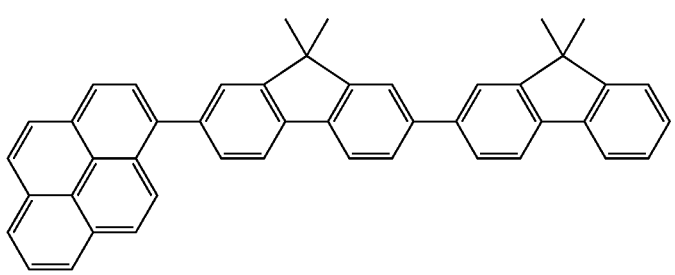 [SMILES: CC1(C)c2ccccc2-c2ccc(-c3ccc4c(c3)C(C)(C)c3cc(-c5ccc6ccc7cccc8ccc5c6c78)ccc3-4)cc21] | H11 |

TABLE 6-continued
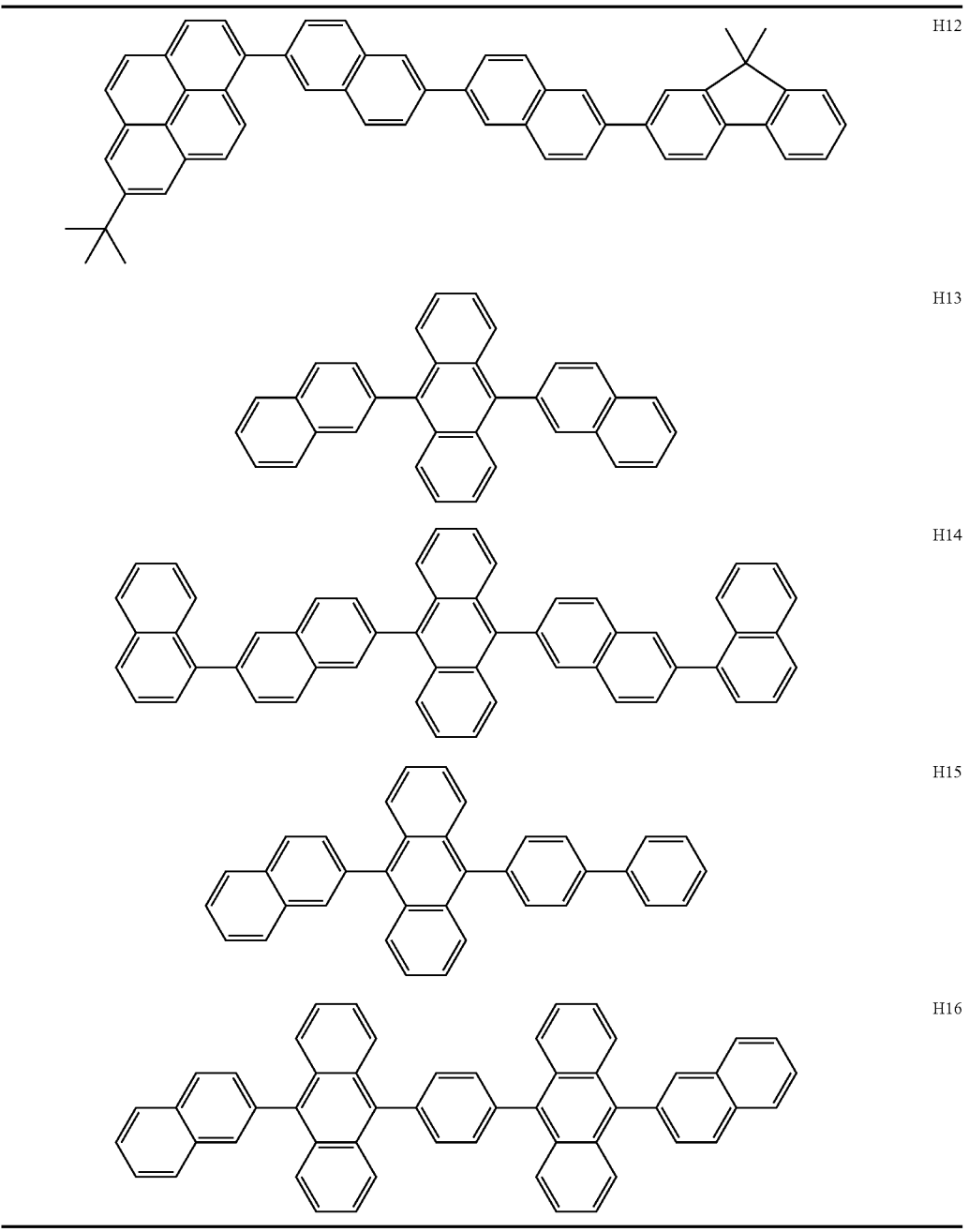
TABLE 7
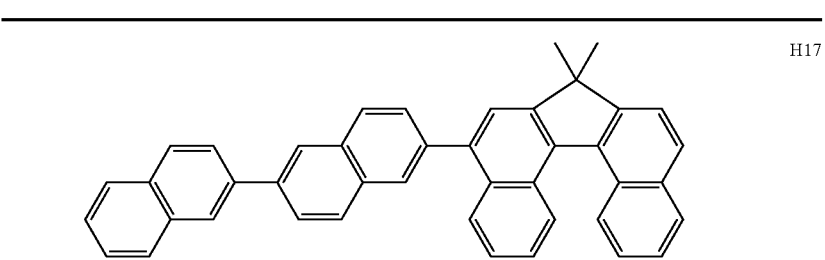

TABLE 7-continued
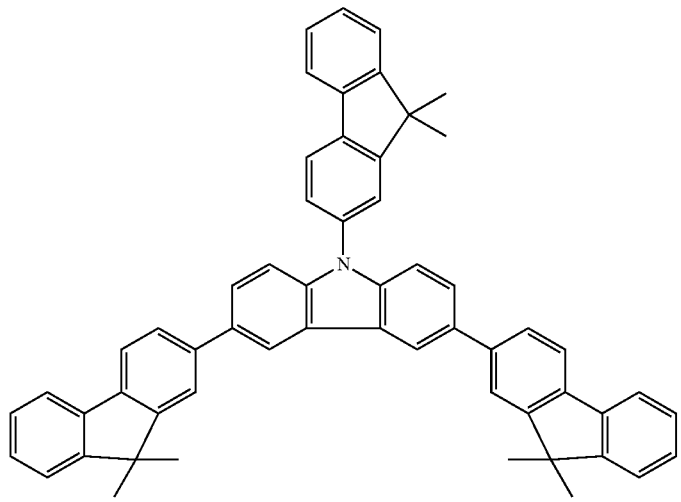 [SMILES: CC1(C)c2ccccc2-c2ccc(-c3ccc4c(c3)c3cc(-c5ccc6c(c5)C(C)(C)c5ccccc5-6)ccc3n4-c3ccc4c(c3)C(C)(C)c3ccccc3-4)cc21]
H18
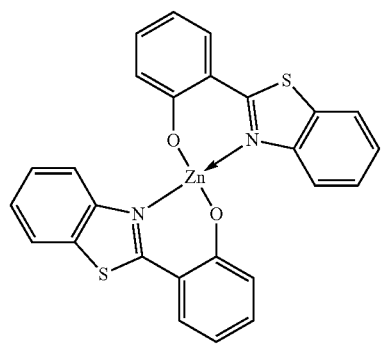
H19
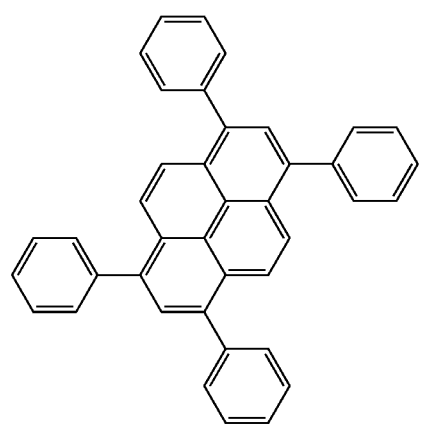 [SMILES: c1ccc(-c2cc(-c3ccccc3)c3ccc4c(-c5ccccc5)cc(-c5ccccc5)c5ccc2c3c54)cc1]
H20
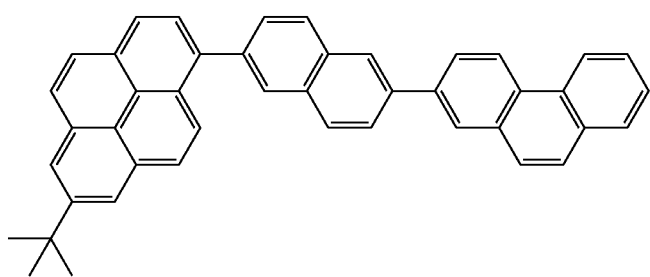 [SMILES: CC(C)(C)c1cc2ccc3ccc(-c4ccc5cc(-c6ccc7c(ccc8ccccc87)c6)ccc5c4)c4ccc(c1)c2c34]
H21

TABLE 7-continued
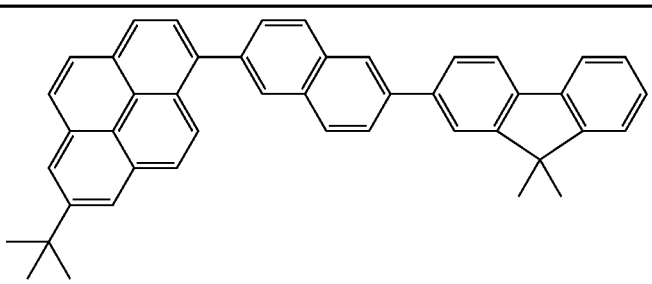
H22
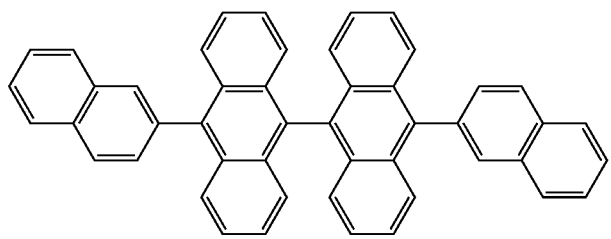 [SMILES: c1ccc2cc(-c3c4ccccc4c(-c4c5ccccc5c(-c5ccc6ccccc6c5)c5ccccc45)c4ccccc34)ccc2c1]
H23
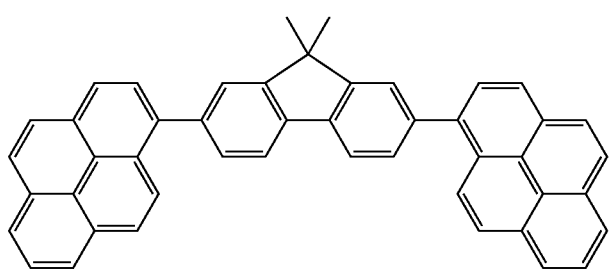 [SMILES: CC1(C)c2cc(-c3ccc4ccc5cccc6ccc3c4c56)ccc2-c2ccc(-c3ccc4ccc5cccc6ccc3c4c56)cc21]
H24
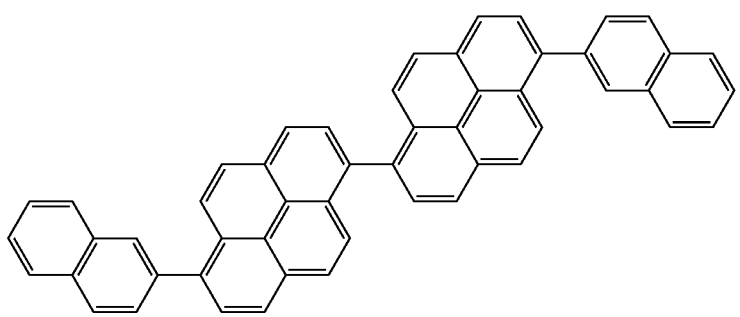 [SMILES: c1ccc2cc(-c3ccc4ccc5c(-c6ccc7ccc8c(-c9ccc%10ccccc%10c9)ccc9ccc6c7c98)ccc6ccc3c4c65)ccc2c1]
H25
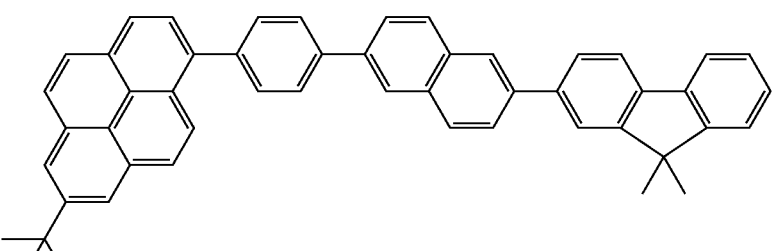
H26
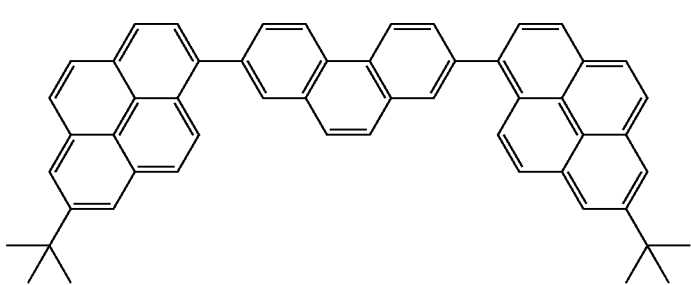 [SMILES: CC(C)(C)c1cc2ccc3ccc(-c4ccc5c(ccc6cc(-c7ccc8ccc9cc(C(C)(C)C)cc%10ccc7c8c9%10)ccc65)c4)c4ccc(c1)c2c34]
H27

TABLE 7-continued

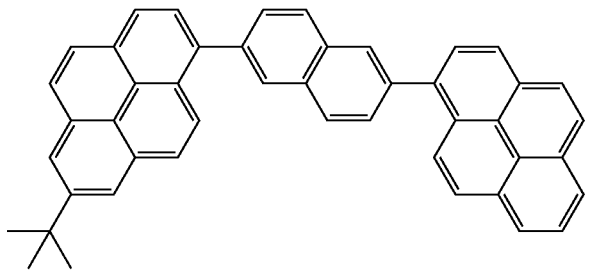 [SMILES: CC(C)(C)c1cc2ccc3ccc(-c4ccc5cc(-c6ccc7ccc8cccc9ccc6c7c89)ccc5c4)c4ccc(c1)c2c34]

H28

The electron injection/transport material can be adequately selected from materials into which electrons are easily injected from the negative electrode and which can transport the injected electrons to the light-emitting layer. The material is selected in consideration of, for example, the balance with the hole mobility of the hole injection/transport material. Examples of the electron injection/transport material include, but are not limited to, oxadiazole derivatives, oxazole derivatives, pyrazine derivatives, triazole derivatives, triazine derivatives, quinoline derivatives, quinoxaline derivatives, phenanthroline derivatives, and organoaluminum complexes.

The material for the positive electrode should have as high a work function as possible. Examples of the material include metal elements such as gold, platinum, silver, copper, nickel, palladium, cobalt, selenium, vanadium, and tungsten; alloys thereof; and metal oxides such as tin oxide, zinc oxide, indium oxide, indium tin oxide (ITO), and indium zinc oxide. Electrically conductive polymers such as polyaniline, polypyrrole, and polythiophene can also be used. These electrode substances may be used alone or in combination of two or more substances. The positive electrode may have a single-layer structure or a multilayer structure.

The material for the negative electrode should have as low a work function as possible. Examples of the material include metal elements such as alkali metals, e.g., lithium; alkaline earth metals, e.g., calcium; aluminum; titanium; manganese; silver; lead; and chromium. Alloys combining these metal elements with each other can also be used. Examples of the alloys include magnesium-silver, aluminum-lithium, and aluminum-magnesium. Metal oxides such as indium tin oxide (ITO) can also be used. These electrode substances may be used alone or in combination of two or more substances. The negative electrode may have a single-layer structure or a multilayer structure.

In order to prevent the produced organic light-emitting device from contacting oxygen, moisture, and the like, a protective layer or a sealing layer can be formed on the device.

In the organic light-emitting device according to this embodiment, a layer containing the organic compound according to this embodiment and layers composed of other organic compounds are formed by the method described below. In general, a thin film is formed by a vacuum deposition method, an ionized vapor deposition method, a sputtering method, a plasma deposition method, or a publicly known coating method that involves dissolving of a compound in an adequate solvent. When such a film is formed by a vacuum deposition method, a solution coating method, or the like, crystallization does not readily occur and thus the resulting film has high stability over time. When a coating method is used to form such a film, an adequate binder resin can be used in combination with the compound.

Examples of the binder resin include, but are not limited to, polyvinylcarbazole resin, polycarbonate resin, polyester resin, ABS resin, acrylic resin, polyimide resin, phenolic resin, epoxy resin, silicone resin, and urea resin. Furthermore, publicly known additives such as a plasticizer, an antioxidant, and an ultraviolet absorber may be optionally added to these binder resins.

An apparatus including the organic light-emitting device according to this embodiment will now be described.

The organic light-emitting device according to this embodiment can be used for a display apparatus and an illuminating device. In addition, the organic light-emitting device according to this embodiment can be used for an exposure light source of an electrophotographic image-forming apparatus and a backlight of a liquid crystal display apparatus.

The display apparatus includes a display unit including the organic light-emitting device according to this embodiment. This display unit includes a plurality of pixels. Each of the pixels includes the organic light-emitting device according to this embodiment and a thin-film transistor (TFT) device, which is an example of a switching device. A positive electrode or a negative electrode of this organic light-emitting device is connected to a drain electrode or a source electrode of the TFT device. The display apparatus can be used as an image display apparatus of a personal computer (PC) or the like. The display apparatus may be an image input apparatus that further includes an image input unit.

The image input apparatus includes an image input unit with which information from an area CCD sensor, a linear CCD sensor, a memory card, or the like is input and a display unit configured to display the input information. If such an image input apparatus further includes an imaging optical system, an image pickup apparatus such as a digital camera is obtained. Such an image pickup apparatus or an ink jet printer may have both a display unit with an image output function of displaying an image on the basis of image information input from the outside and an operation panel with an input function of inputting process information to the image. The display apparatus may be used for a display unit of a multifunction printer.

A display apparatus including the organic light-emitting device according to this embodiment will now be described.

FIG. 1 is a schematic sectional view of a display apparatus including organic light-emitting devices according to this embodiment and TFT devices, which are an example of switching devices configured to switch the emission/non-emission of the organic light-emitting devices or control the light emission luminance. FIG. 1 shows two pairs of an organic light-emitting device and a TFT device. Although not shown in the drawing, the display apparatus may further include a transistor configured to control the light emission luminance. The display apparatus performs display by turning on or turning off the organic light-emitting devices by driving the switching devices in accordance with information, and transmits the information. The detailed structure of the display apparatus will be described below.

The display apparatus shown in FIG. 1 includes a substrate 1 composed of, for example, glass and a moisture-proof film 2 for protecting TFT devices or organic compound layers, the moisture-proof film 2 being disposed on the substrate 1. Reference numeral 3 denotes a metal gate electrode, reference numeral 4 denotes a gate insulating film, and reference numeral 5 denotes a semiconductor layer.

A TFT device 8 includes the semiconductor layer 5, a drain electrode 6, and a source electrode 7. An insulating film 9 is disposed on the upper portion of the TFT device 8. A positive electrode 11 of an organic light-emitting device is connected to the source electrode 7 through a contact hole 10. The structure of the display apparatus is not limited thereto. Either the positive electrode or the negative electrode of the organic light-emitting device needs only to be connected to either the source electrode or the drain electrode of the TFT device.

In FIG. 1, a plurality of organic compound layers are shown as a single organic compound layer 12. A first protective layer 14 and a second protective layer 15 for suppressing the degradation of the organic light-emitting device are disposed on a negative electrode 13.

In the display apparatus according to this embodiment, the switching device is not particularly limited. A single crystal silicon substrate, a metal-insulator-metal (MIM) device, an amorphous silicon (a-Si) device, or the like may be used.

EXAMPLES

Example 1

Synthesis of A110 and A110-2

An isomer of example compound A110 is expressed as "A110-2".

[Chem. 25]

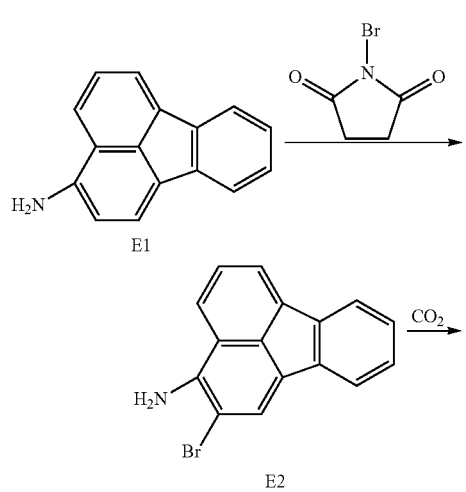

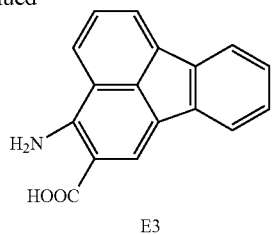

First, 10.5 g (48 mmol) of fluoranthene-3-amine (E1) was added to 300 ml of dimethylformamide at 0° C. Next, 8.2 g (48 mmol) of N-bromosuccinimide was added to the mixture. The temperature was returned to room temperature, and the mixture was stirred for eight hours. The resultant precipitate was filtered in water and then recrystallized with ethanol. The crystal was filtered, washed with heptane, and then dried. Thus, 29 g of brown solid E2 was obtained (yield: 60%). Subsequently, 10 g (34 mmol) of E2 was put in a 500 ml eggplant-type flask, and the air inside the system was replaced with argon. Next, 150 ml of methoxycyclopentane was put in the flask in an argon atmosphere, and the solution was cooled to −75° C. Subsequently, 64 ml of 1.6 M n-butyllithium solution was added dropwise thereto. After the dropwise addition, the temperature was returned to room temperature, and stirring was performed for one hour. Next, the mixture was again cooled to −75° C., and 15 g of finely crushed dry ice was added to the mixture. After the temperature was gradually returned to room temperature, stirring was performed for eight hours, and then 1 M hydrochloric acid was added to the mixture to terminate the reaction. Subsequently, extraction was performed with ethyl acetate and the organic layer was concentrated to obtain a brown liquid. The liquid was purified by column chromatography (ethyl acetate/heptane=1:3) and recrystallized with chloroform/methanol. Thus, 2.5 g of E3, which was a greenish yellow crystal, was obtained (yield: 28%).

[Chem. 26]

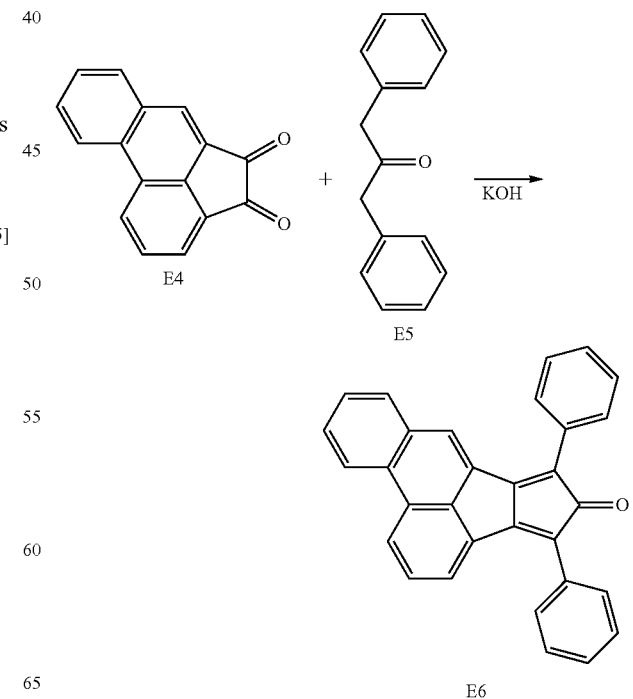

Next, 35 g (150 mmol) of E4 and 31.8 g (150 mmol) of E5 were put in 500 ml of ethanol/toluene solution (10/1), and 52 ml of 6 N potassium hydroxide solution was added dropwise thereto while the mixture was being stirred. After the dropwise addition, the mixture was heated to 50° C., stirred for one hour, and then cooled. The resultant precipitate was filtered and washed with water, ethanol, and isopropyl alcohol in that order. Drying by heating under reduced pressure was performed to obtain 48.2 g of black solid E6 (yield: 78%).

[Chem. 27]

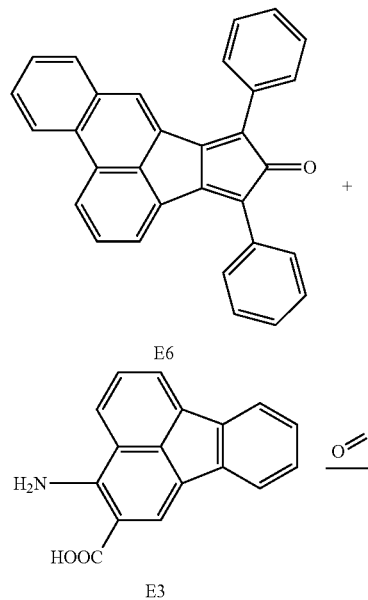

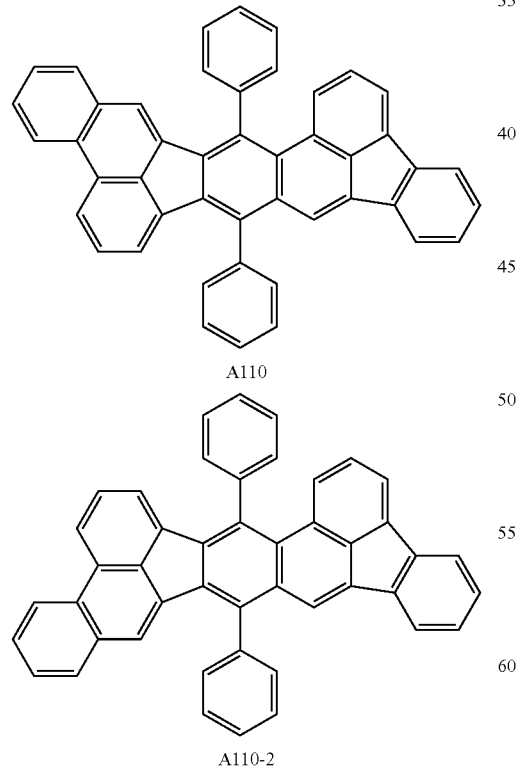

Next, 3.6 g (8.95 mmol) of E6 and 2.6 g (9.74 mmol) of E3 were put in 100 ml of toluene, and the mixture was heated to 80° C. Subsequently, 1.2 ml (10.4 mmol) of isoamyl nitrite was then slowly added dropwise to the mixture. The mixture was then stirred at 110° C. for three hours. The mixture was cooled and then washed with 100 ml of water twice. The resultant organic layer was washed with a saturated saline solution and dried with magnesium sulfate. Subsequently, the resultant solution was filtered, and the filtrate was concentrated to obtain a brown liquid. The liquid was purified by column chromatography (toluene/heptane=3:1) and recrystallized with toluene/ethanol. Thus, 3.17 g of a yellow crystal solid, which was a mixture of isomers, was obtained (yield: 62%).

The structure of the compound was confirmed by NMR spectroscopy.

$^1$H NMR (CDCl$_3$, 400 MHz) σ (ppm): 8.57 (dd, 2H, J=8.24, 4.12 Hz), 8.37 (dd, 2H, J=8.24, 2.29 Hz), 8.21 (d, 2H, J=10.99 Hz), 7.87-7.28 (m, 54H), 6.76 (S, 1H), 6.58 (d, 1H, J=7.33 Hz), 6.51 (s, 1H), 6.36 (d, 1H, J=7.33 Hz)

Photoluminescence spectra of 1×10$^{-5}$ mol/L toluene solutions containing example compounds A110 and A110-2 were measured with F-4500 available from Hitachi Ltd., at an excitation wavelength of 350 nm. Both the spectra had the maximum intensity at 439 nm.

Example 2

Synthesis of Compounds A8 and A8-2

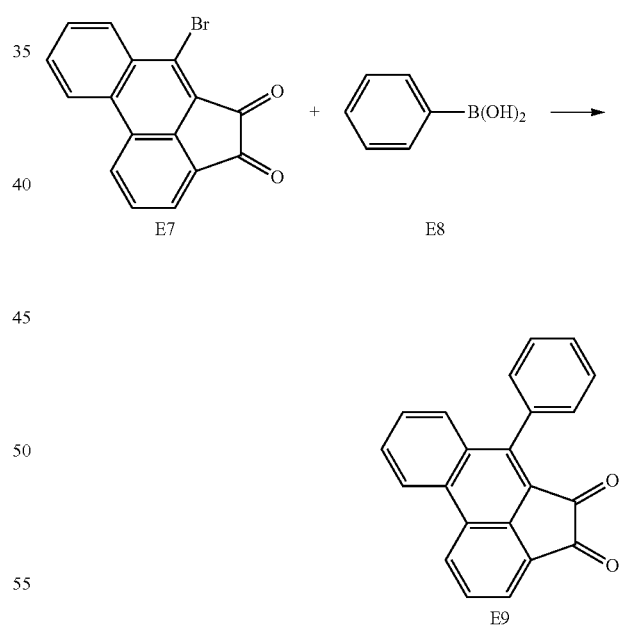

Organic compounds E7 and E8 were added to a mixed solvent of toluene, ethanol, and an aqueous sodium carbonate solution, and a coupling reaction (the temperature of mixed solution: 78° C., reaction time: 10 hours) was performed using tetrakistriphenylphosphine palladium as a catalyst. After the reaction, the organic layer was washed with water and dried. Column separation was performed using a toluene/heptane solvent and recrystallization was then performed in a toluene solvent to obtain a crystal solid E9.

[Chem. 29]

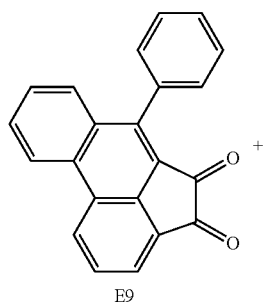

E9

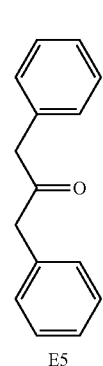

E5

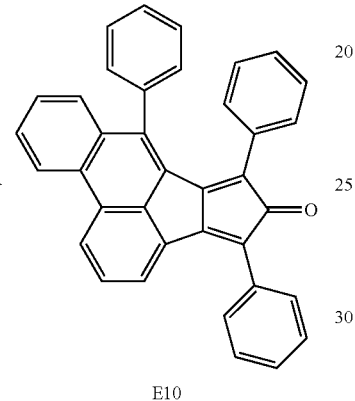

E10

Next, compound E10 was synthesized through the same reaction and purification as those of Example 1, except that the organic compound E4 used in Example 1 was changed to E9.

[Chem. 30]

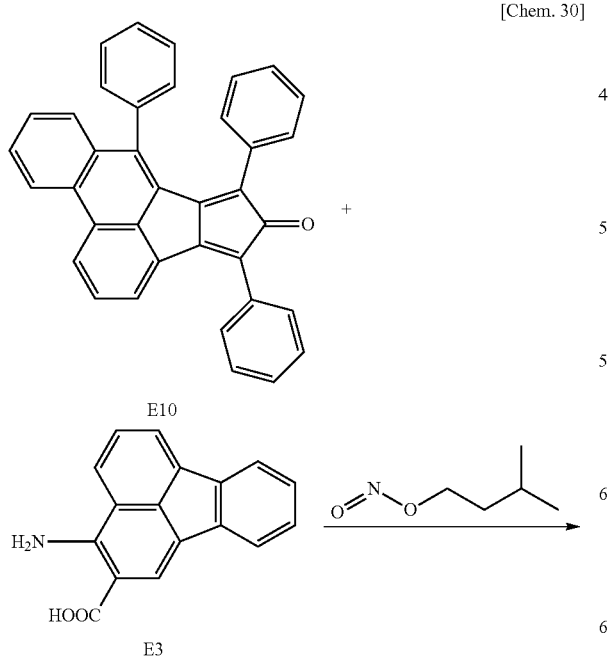

E10

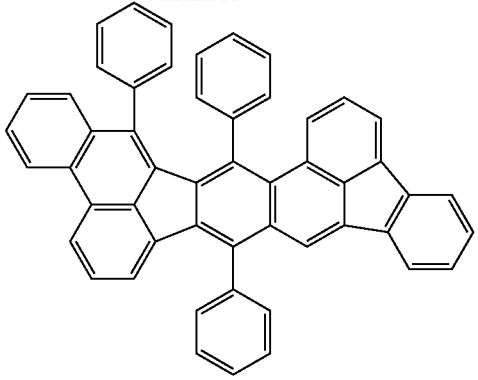

A8

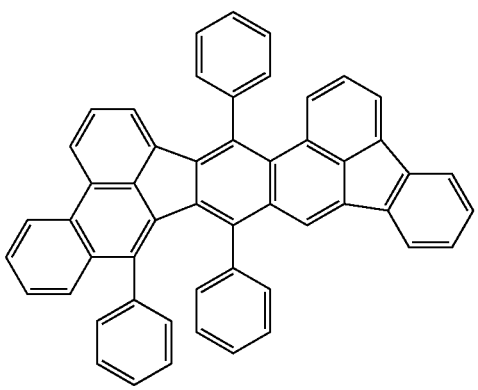

A8-2

A yellow crystal solid, which was a mixture of isomers, was obtained through the same reaction and purification as those of Example 1, except that the organic compound E6 used in Example 1 was changed to E10. Part of the yellow crystal solid was separated into compounds A8 and A8-2 through recrystallization.

Photoluminescence spectra of $1 \times 10^{-5}$ mol/L toluene solutions containing example compounds A8 and A8-2 were measured with F-4500 available from Hitachi Ltd., at an excitation wavelength of 350 nm. Both the spectra had the maximum intensity at 451 nm.

Example 3

Synthesis of A24 and A24-2

The same reaction and purification as those of Example 2 were performed, except that E7 and E8 in Example 2 were changed to E11 and E12, respectively.

[Chem. 31]

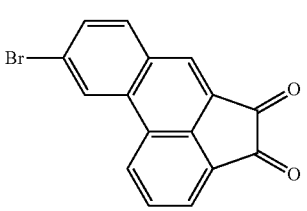

E11

[Chem. 32]

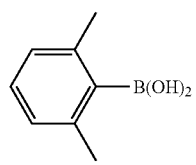

E12

Photoluminescence spectra of 1×10⁻⁵ mol/L toluene solutions containing example compounds A24 and A24-2 were measured with F-4500 available from Hitachi Ltd., at an excitation wavelength of 350 nm. Both the spectra had the maximum intensity at 445 nm.

Example 4

Synthesis of A54 and A54-2

The same reaction and purification as those of Example 2 were performed, except that E7 and E5 in Example 2 were changed to E11 and E13, respectively.

[Chem. 33]

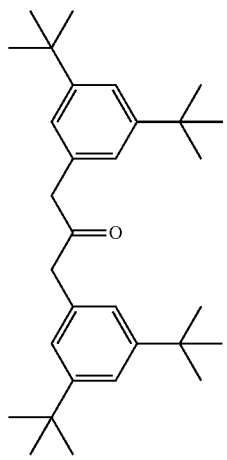

E13

Photoluminescence spectra of 1×10⁻⁵ mol/L toluene solutions containing example compounds A54 and A54-2 were measured with F-4500 available from Hitachi Ltd., at an excitation wavelength of 350 nm. Both the spectra had the maximum intensity at 453 nm.

Example 5

Synthesis of A73 and A73-2

The same reaction and purification as those of Example 2 were performed, except that E4 in Example 2 was changed to E14.

[Chem. 34]

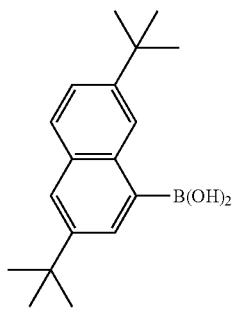

E14

Photoluminescence spectra of 1×10⁻⁵ mol/L toluene solutions containing example compounds A73 and A73-2 were measured with F-4500 available from Hitachi Ltd., at an excitation wavelength of 350 nm. Both the spectra had the maximum intensity at 455 nm.

Example 6

Synthesis of A93 and A93-2

The same reaction and purification as those of Example 2 were performed, except that E8 and E5 in Example 2 were changed to E12 and E16, respectively.

[Chem. 33]

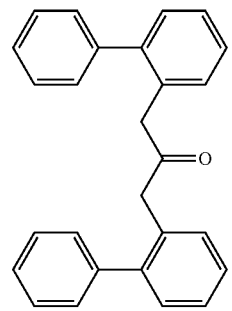

E16

Photoluminescence spectra of 1×10⁻⁵ mol/L toluene solutions containing example compounds A93 and A93-2 were measured with F-4500 available from Hitachi Ltd., at an excitation wavelength of 350 nm. Both the spectra had the maximum intensity at 443 nm.

Examples 7 to 33

In Examples 7 to 33, there were employed multilayer organic light-emitting devices (positive electrode/hole injection layer/hole transport layer/light-emitting layer/hole exciton-blocking layer/electron transport layer/negative electrode). An ITO film having a thickness of 100 nm was patterned on a glass substrate. On the substrate having the ITO film thereon, organic layers and electrode layers described below were successively formed by a resistance-heating vacuum deposition method in a vacuum chamber at a pressure of 10⁻⁵ Pa so that the area of the electrodes facing each other was 3 mm².
Hole transport layer (30 nm) G-1
Light-emitting layer (30 nm) host: G-2, guest: example compound (5% by weight)

Hole exciton-blocking layer (10 nm) G-3
Electron transport layer (30 nm) G-4
Metal electrode layer 1 (1 nm) LiF
Metal electrode layer 2 (100 nm) Al

[Chem. 36]

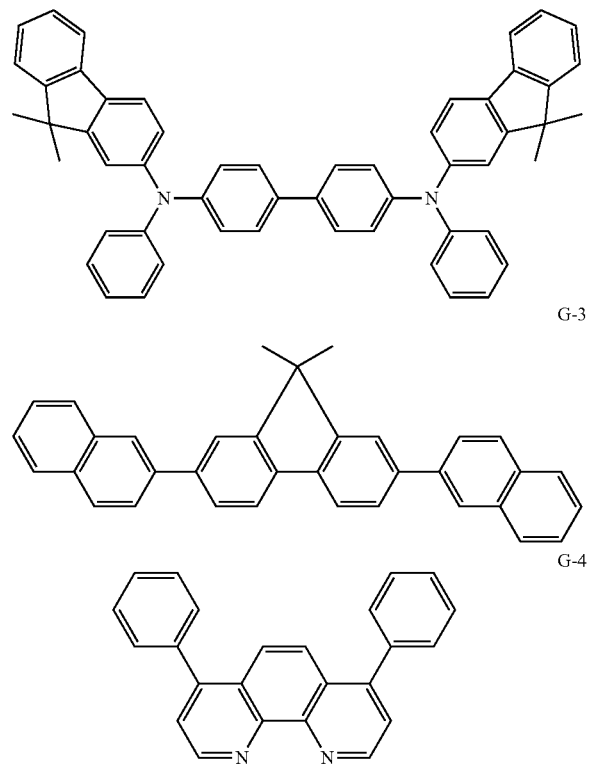

The current-voltage characteristic of each of the organic light-emitting devices was measured with a pA meter 4140B manufactured by Hewlett-Packard Development Company, and the light emission luminance thereof was measured with BM7 manufactured by Topcon Corporation.

Table 8 shows the emission efficiency and voltage of Examples 7 to 33. The guest materials in Table 8 are synthetic compounds in Table 1.

TABLE 8

|  | Synthetic compound | Host (G-2) | Emission efficiency (cd/A) | Voltage (V) |
| --- | --- | --- | --- | --- |
| Example 7 | A1, A1-2 | H12 | 6.3 | 4.5 |
| Example 8 | A8, A8-2 | H10 | 6.1 | 4.7 |
| Example 9 | A20, A20-2 | H8 | 6.4 | 4.2 |
| Example 10 | A26, A26-2 | H21 | 6.5 | 4.2 |
| Example 11 | A35, A35-2 | H10 | 6.3 | 4.4 |
| Example 12 | A36, A36-2 | H21 | 6.3 | 4.4 |
| Example 13 | A44, A44-2, A45, A45-2 | H6 | 6.2 | 4.7 |
| Example 14 | A48, A48-2 | H9 | 6.4 | 4.2 |
| Example 15 | A50, A50-2 | H21 | 6.4 | 4.2 |
| Example 16 | A51, A51-2, A52, A52-2 | H24 | 6.1 | 4.8 |
| Example 17 | A65, A65-2 | H27 | 6.3 | 4.6 |
| Example 18 | A66, A66-2 | H8 | 6.3 | 4.6 |
| Example 19 | A67, A67-2 | H10 | 6.0 | 4.7 |
| Example 20 | A68, A68-2 | H22 | 5.9 | 4.9 |
| Example 21 | A85, A85-2 | H10 | 6.1 | 4.6 |
| Example 22 | A96, A96-2 | H27 | 6.5 | 4.1 |

TABLE 8-continued

|  | Synthetic compound | Host (G-2) | Emission efficiency (cd/A) | Voltage (V) |
| --- | --- | --- | --- | --- |
| Example 23 | A97, A97-2 | H9 | 6.5 | 4.1 |
| Example 24 | A110, A110-2 | H22 | 6.5 | 4.2 |
| Example 25 | A113, A113-2 | H2 | 6.2 | 4.7 |
| Example 26 | A114, A114-2 | H16 | 6.2 | 4.7 |
| Example 27 | A118, A118-2 | H26 | 6.0 | 4.9 |
| Example 28 | B4, B4-2 | H24 | 5.9 | 4.9 |
| Example 29 | B25, B25-2 | H28 | 6.4 | 4.3 |
| Example 30 | C5, C5-2 | H23 | 6.3 | 4.0 |
| Example 31 | C8, C8-2 | H17 | 4.3 | 5.5 |
| Example 32 | C10, C10-2 | H18 | 4.8 | 6.1 |

Examples 34 to 39

In Examples 34 to 39, there were prepared organic light-emitting devices having a structure of positive electrode/hole injection layer/hole transport layer/light-emitting layer/electron transport layer/electron injection layer/negative electrode.

An aluminum alloy (AlNd) serving as a reflective positive electrode was formed on a glass substrate serving as a support by a sputtering method so as to have a thickness of 100 nm. Furthermore, an ITO film serving as a transparent positive electrode was formed by a sputtering method so as to have a thickness of 80 nm. Next, a device isolation film composed of an acrylic resin and having a thickness of 1.5 μm was formed in a peripheral portion of the positive electrode, and an opening with a radius of 3 mm was formed therein. The substrate was washed with ultrasonic waves sequentially using acetone and isopropyl alcohol (IPA). The substrate was then washed with IPA under boiling and dried. Furthermore, UV/ozone cleaning was performed on the surface of the substrate.

Organic layers described below were successively formed by a resistance-heating vacuum deposition method in a vacuum chamber at a pressure of $10^{-5}$ Pa. Subsequently, IZO was deposited by a sputtering method to form a transparent electrode serving as a negative electrode and having a thickness of 30 nm. After the formation, sealing is performed in a nitrogen atmosphere.

Hole injection layer (95 nm) G-11
Hole transport layer (10 nm) G-12
Light-emitting layer (35 nm) host: G-13, guest: example compound (2% by weight)
Electron transport layer (10 nm) G-14
Electron injection layer (70 nm) G15 (80% by weight) and Li (20% by weight)

[Chem. 37]

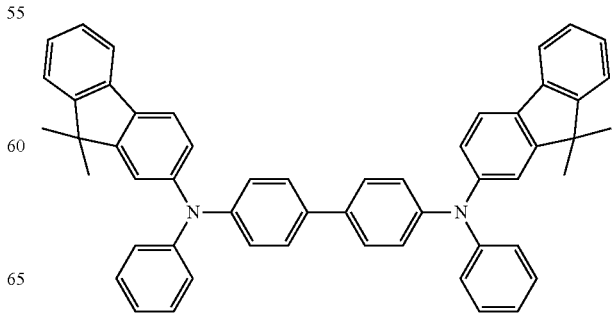

-continued

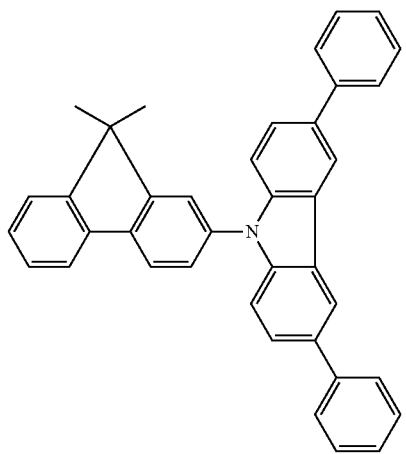

G-12

G-14

G-15

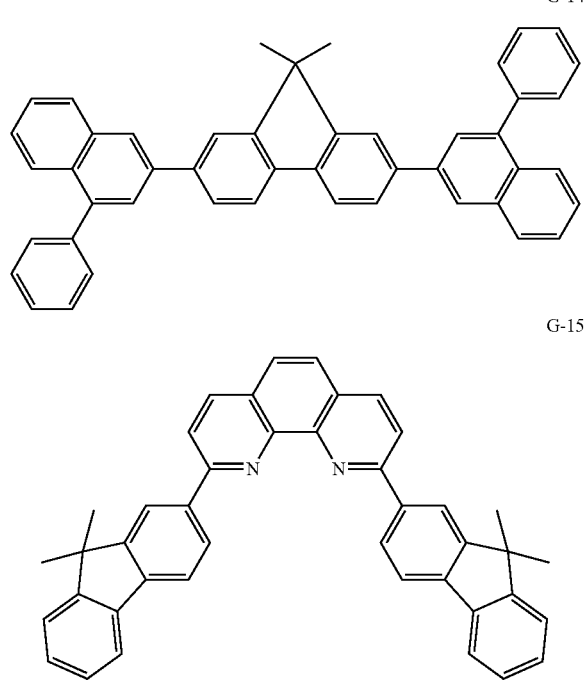

The current-voltage characteristic of each of the organic light-emitting devices was measured with a pA meter 4140B manufactured by Hewlett-Packard Development Company, and the light emission luminance thereof was measured with BM7 manufactured by Topcon Corporation.

Table 9 shows the emission efficiency and voltage of Examples 34 to 39.

TABLE 9

| | Guest | Host (G-13) | Emission efficiency (cd/A) | Voltage (V) |
|---|---|---|---|---|
| Example 34 | A1, A1-2 | H27 | 2.9 | 4.5 |
| Example 35 | A24, A24-2 | H9 | 3.0 | 4.3 |
| Example 36 | A36, A36-2 | H10 | 3.1 | 4.3 |
| Example 37 | A73, A73-2 | H8 | 3.1 | 4.3 |
| Example 38 | A110, A110-2 | H22 | 3.2 | 4.2 |
| Example 39 | A116, A116-2 | H21 | 3.0 | 4.3 |

(Results and Discussion)

The organic compounds according to the present invention are novel compounds that exhibit high quantum yield and are suitable for blue light emission. When the organic compounds are used for organic light-emitting devices, it is possible to make light-emitting devices having satisfactory luminescence characteristics.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-105625, filed Apr. 30, 2010, which is hereby incorporated by reference herein in its entirety.

REFERENCE SIGNS LIST

8 TFT device
11 positive electrode
12 organic compound layer
13 negative electrode

The invention claimed is:

1. An organic compound represented by general formula (1) below:

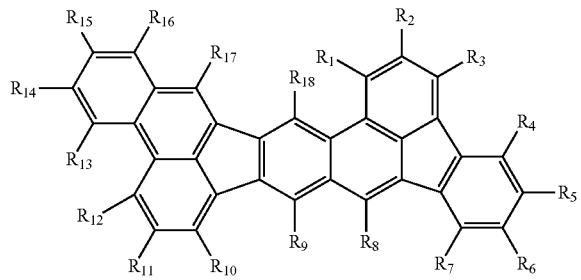

(1)

wherein, in the general formula (I), $R_1$ to $R_{18}$ are each independently selected from a hydrogen atom, a halogen atom, an alkyl group, an alkoxy group, an amino group, an aryl group, and a heterocyclic group.

2. The organic compound according to claim 1, wherein at least one of the $R_1$ to $R_8$ and the $R_{10}$ to $R_{17}$ is selected from the alkyl group and the aryl group and the other of the $R_1$ to $R_8$ and the $R_{10}$ to $R_{17}$ are hydrogen atoms.

3. An organic compound represented by general formula (3) below:

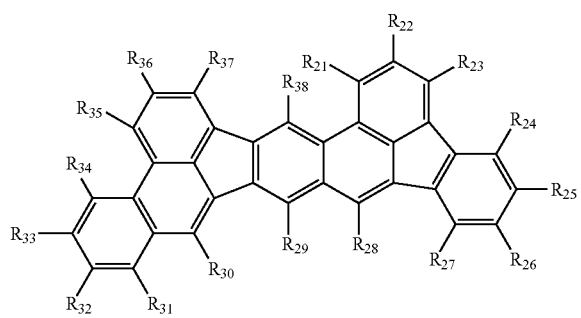

(3)

wherein, in the general formula (3), $R_{21}$ to $R_{38}$ are each independently selected from a hydrogen atom, an aryl group, and an alkyl group.

4. An organic light-emitting device comprising:
a pair of electrodes; and
an organic compound layer disposed between the pair of electrodes,
wherein the organic compound layer comprises the organic compound according to claim 1.

5. An organic light-emitting device comprising:
a pair of electrodes; and
an organic compound layer disposed between the pair of electrodes,
wherein the organic compound layer comprises the organic compound according to claim 3.

6. The organic light-emitting device according to claim 4, wherein the organic compound layer is a light-emitting layer.

7. A display apparatus comprising:
a plurality of pixels that each include the organic light-emitting device according to claim 4 and a switching device connected to the organic light-emitting device.

8. An image input apparatus comprising:
an image input unit with which an image is input; and
a display unit configured to display the image,
wherein the display unit includes a plurality of pixels that each include the organic light-emitting device according to claim 4 and a switching device connected to the organic light-emitting device.

9. A display apparatus comprising:
a plurality of pixels that each include the organic light-emitting device according to claim 5 and a switching device connected to the organic light-emitting device.

10. An image input apparatus comprising:
an image input unit with which an image is input; and
a display unit configured to display the image,
wherein the display unit includes a plurality of pixels that each include the organic light-emitting device according to claim 5 and a switching device connected to the organic light-emitting device.

11. An illuminating device comprising the organic light-emitting device according to claim 4.

12. An electrophotographic image-forming apparatus comprising an exposure light source,
the exposure light source comprising the organic light-emitting device according to claim 4.

* * * * *